US012247050B2

(12) United States Patent
Daggett et al.

(10) Patent No.: US 12,247,050 B2
(45) Date of Patent: Mar. 11, 2025

(54) α-SHEET POLYPEPTIDES AND THEIR USE

(71) Applicant: University of Washington, Seattle, WA (US)

(72) Inventors: Valerie Daggett, Seattle, WA (US); Dylan Shea, Seattle, WA (US); Alissa Bleem, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 174 days.

(21) Appl. No.: 17/749,969

(22) Filed: May 20, 2022

(65) Prior Publication Data

US 2023/0048960 A1    Feb. 16, 2023

Related U.S. Application Data

(60) Provisional application No. 63/224,815, filed on Jul. 22, 2021.

(51) Int. Cl.
| | |
|---|---|
| *C07K 14/00* | (2006.01) |
| *A61K 9/70* | (2006.01) |
| *A61K 38/17* | (2006.01) |
| *A61P 25/28* | (2006.01) |
| *C07K 7/06* | (2006.01) |
| *C07K 7/08* | (2006.01) |

(52) U.S. Cl.
CPC .......... *C07K 14/001* (2013.01); *A61K 9/7007* (2013.01); *A61K 38/1787* (2013.01); *A61P 25/28* (2018.01); *C07K 7/06* (2013.01); *C07K 7/08* (2013.01)

(58) Field of Classification Search
CPC ........ A61L 31/16; A61L 31/10; A61L 29/085; A61L 2300/252; A61L 27/56; A61L 2300/606; A61L 2420/08; A61L 27/52; A61L 2420/00; A61L 24/001; A61L 2430/12; A61P 41/00; B82Y 40/00; B82Y 30/00; B82Y 5/00; A61K 31/704; A61K 9/0024; A61K 9/5094; A61K 9/0092; A61B 5/412; B01D 2323/38; B01D 2325/48

See application file for complete search history.

(56) References Cited

U.S. PATENT DOCUMENTS

| | | | | |
|---|---|---|---|---|
| 8,242,241 | B2 * | 8/2012 | Daggett ................. | G16B 15/30 530/326 |
| 9,896,487 | B2 * | 2/2018 | Daggett ................. | A61K 38/03 |
| 11,033,604 | B2 * | 6/2021 | Daggett ................. | A61L 29/16 |
| 11,826,398 | B2 * | 11/2023 | Daggett ................. | A61L 27/34 |
| 2024/0050517 | A1 * | 2/2024 | Daggett ................. | A61K 38/02 |

FOREIGN PATENT DOCUMENTS

WO    WO2014159941 A1 * 10/2014 ............. G01N 33/68

OTHER PUBLICATIONS

Paranjapye et al. De novo designed alpha-sheet peptides inhibit functional amyloid formation of Streptococcus mutans biofilms. J Mol Biol. Oct. 12, 2018; 430(20): 3764-3773. (Year: 2018).*
Noriega-Luna et al. Applications of Dendrimers in Drug Delivery Agents, Diagnosis, Therapy, and Detection. Journal of Nanomaterials vol. 2014, Article ID 507273, 19 pages. (Year: 2014).*
Luo et al. Improved immobilization of biomolecules to quinone-rich polydopamine for efficient surface functionalization. Colloids and Surfaces B: Biointerfaces 106 (2013) 66-73. (Year: 2013).*
Leuzy, et al. (2018) In vivo detection of Alzheimer's disease. Yale J. of Biol. and Med. 91, 291-300.
Li, et al. A mechanistic hypothesis for the impairment of synaptic plasticity by soluble Abeta oligomers from Alzheimer's brain. J. Neurochem. 154, 583-597, 2020.
Li, et al. Cross-sectional and longitudinal relationships between cerebrospinal fluid biomarkers and cognitive function in subjects without cognitive impairment from across the adult life span. JAMA Neural. 2014; 71(6):742-51.
Lim, et al. Dimethyl sulfoxide and ethanol elicit increased amyloid biogenesis and amyloid-integrated biofilm formation in *Escherichia coli*. Appl. Environ. Microbiol. 78, 3369-3378 (2012).
Lim, K. et al. Development of a catheter functionalized by a polydopamine peptide coating with antimicrobial and antibiofilm properties. Acta Biomater. 15, 127-138 (2015).
Link, et al. (2003) Gene expression analysis in a transgenic Caenorhabditis elegans Alzheimer's disease model. Neurobiol Aging 24:397-413.
Linse (2017) Monomer-dependent secondary nucleation in amyloid formation. Biophys Rev 9:329-338.
Lu & Collins. Dispersing biofilms with engineered enzymatic bacteriophage. Proc. Natl. Acad. Sci. 104, 11197-11202 (2007).
Lührs, et al. (2005) 3D structure of Alzheimer's amyloid-β(1-42) fibrils. Proc Natl Acad Sci USA 102:17342-17347.
Luo, et al.(2014) Alzheimer peptides aggregate into transient nanoglobules that nucleate fibrils. Biochemistry 53:6302-6308.
Luo, et al. (2018) A self-destructive nanosweeper that captures and clears amyloid β-peptides. Nat Commun 9:1802-1806.
Madiona, et al. Determining the limit of detection of surface bound antibody. Biointerphases, 12, 031007 (2017).
Maris, et al (2018) Chemical and physical variability in structural isomers of an L/D α-sheet peptide designed to inhibit amyloidogenesis. Biochemistry 57:507-510.
Masters, et al. (1985) Amyloid plaque core protein in Alzheimer disease and Down syndrome. Proc Natl Acad Sci USA 82:4245-4249.
Masters, et al. (20 15) Alzheimer's disease. Nat. Rev. Disease Primers 1, 15056.

(Continued)

*Primary Examiner* — Aradhana Sasan
*Assistant Examiner* — Jia-Hai Lee
(74) *Attorney, Agent, or Firm* — MCDONNELL BOEHNEN HULBERT & BERGHOFF LLP

(57) ABSTRACT

Alpha-sheet polypeptide multimers, and polypeptides for making multimers, compositions and medical devices including them, and their use for treating and diagnosing amyloid diseases or amyloid-associated diseases are disclosed.

25 Claims, 12 Drawing Sheets

Specification includes a Sequence Listing.

(56) References Cited

OTHER PUBLICATIONS

Mattson, et al., The Alzheimer's Association external quality control program for cerebrospinal fluid biomarkers. Alz Dement 7(4), 386-395, 2011.
May, et al. An engineered micropattern to reduce bacterial colonization, platelet adhesion and fibrin sheath formation for improved biocompatibility of central venous catheters. Clin. Transl. Med. 4, (2015).
Mcgregor. Discovering and improving novel peptide therapeutics. Curr. Opin. Pharmacol. 8, 616-619 (2008).
Mckhann, et al. Clinical diagnosis of Alzheimer's disease: report of the NINCDS-ADRDA Work Group under the auspices of Department of Health and Human Services Task Force on Alzheimer's Disease. Neurology 14(7):939-944, 1984.
McLean, et al. (1999) Soluble pool of Abeta amyloid as a determinant of severity of neurodegeneration in Alzheimer's disease. Ann Neurol 46:860-866.
Mehta, et al. Plasma and cerebrospinal fluid levels of amyloid beta proteins 1-40 and 1-42 in Alzheimer Disease. Arch. Neurol. 57, 100-105, 2000.
Miller, et al. (2010) Polymorphism in Alzheimer Abeta amyloid organization reflects conformation selection in a rugged energy landscape. Chem. Rev. J 10, 4820-4838.
Milojevic, et al. Stoichiometry and affinity of the human serum albumin Alzheimer's Abeta peptide interactions. Biophys. J. 100, 183-192 (2011).
Mirra, et al. The Consortium to Establish a Registry for Alzheimer's Disease (CERAO). Part II. Standardization of the heuropathologic assessment of Alzheimer's disease. Neurology, 41, 479-486, 1991.
Morley, et al. (2010) A physiological role for amyloid-β protein: Enhancement of learning and memory. J Alzheimers Dis 19:441-449.
Mucke, et al. (2000) High-level neuronal expression of Abeta(I-42) in wild-type human amyloid protein precursor transgenic mice: Synaptotoxicity without plaque formation. J Neurosci. 20, 4050-4058.
Mullan, et al. (1992) A pathogenic mutation for probable Alzheimer's disease in the APP gene at the N-terminus of beta-amyloid. Nat Genet 1:345-347.
Musiek, et al. (2015) Three dimensions of the amyloid hypothesis: time, space and 'wingmen'. Nature Neurosci. 18, 800-806.
Nabers, et al. Abeta and tau structure-based biomarkers for a blood- and CSF-based two-step recruitment strategy to dentify patients with dementia due to Alzheimer's disease. Alz & Dem: Diag., Assess. & Dis Mon., 11, 257-263, 2019.
Nabers, et al. Amyloid blood biomarker detects Alzheimer's disease. EMBO Mol. Med. 10, e8763, 2018.
Nakamura, et al. High performance plasma amyloid-13 biomarkers for Alzheimer's disease. Nature 554, 249-254.
Noel-Storr, et al. Systematic review of the body of evidence for the use of biomarkers in the diagnosis of dementia. Alzheimer's Dement 2013;9:e96-e105.
Oddo, et al. Triple-transgenic model of Alzheimer's disease with plaques and tangles: intracellular Abeta and synaptic dysfunction. Neuron 39, 409-421, 2003.
Olsson, et al. CSF and blood biomarkers for the diagnosis of Alzheimer's disease: a systematic review and meta-analysis. Lancet Neurol 2016; 15:673-84.
Ono, et al. (2009) Structure-neurotoxicity relationships of amyloid beta-protein oligomers. Proc. Natl. Acad. Sci. USA, 106, 14745-14750.
Orishchin, et al. Rapid Deposition of Uniform Polydopamine Coatings on Nanoparticle Surfaces with Controllable Thickness. Langmuir 33, 6046-6053 (2017).
Palmqvist, et al., Discriminative accuracy of plasma phosphor-tau217 for Alzheimer Disease vs other neurodegenerative disorders. J. Am. Med. Assoc., 324, 772-781, 2020.

Paranjapye, et al. De Novo Designed α-Sheet Peptides Inhibit Functional Amyloid Formation of *Streptococcus* mutans Biofilms. J. Mol. Biol. 430, 3764-3773 (2018).
Percival, et al. Healthcare-associated infections, medical devices and biofilms: risk, tolerance and control. J. Med. Microbiol. 64, 323-334 (2015).
Perni, et al. (2017) Delivery of native proteins into C. elegans using a transduction protocol based on lipid vesicles. Sci Rep 7:15045.
Petersen, et al. Mild cognitive impairment: Clinical characterization and outcome, Arch Neurol 56(3), 303-308, 1999.
Portelius, et al. (2010) Distinct cerebrospinal fluid amyloid beta peptide signatures in sporadic and PSENI A431E-associated familial Alzheimer's disease. Mol. Neurodegener. 5, 2.
Price, et al. Tangles and plaques in nondemented aging and "preclinical" Alzheimer's disease. Ann. Neurol. 1999;45:358-368.
Pujol-Pina, et al. (2015) SDS-PAGE analysis of Aβ oligomers is disserving research into Alzheimer's disease: Appealing for ESI-IM-MS. Sci. Rep. 5, 14809.
Qin, et al. In vitro and in vivo anti-biofilm effects of silver nanoparticles immobilized on titanium. Biomaterials 35, 9114-9125 (2014).
Quadros, et al. (2003) Increased TNFalpha production and Cox-2 activity in organotypic brain slice cultures from APPsw transgenic mice. Neurosci Lett 353:66-68.
Quist, et al. (2005) Amyloid ion channels: A common structural link for protein misfolding disease. Proc. Natl. Acad Sci. USA 102, 10427-10432.
Reyes Barcelo, et al. Soluble aggregates by serum albumin to enhance amyloid-beta activation of endothelial cells. J. Biol. Eng. 3, 5-12 (2009).
Ritchie, et al. Plasma and cerebrospinal fluid amyloid beta for the diagnosis of Alzheimer's disease dementia and other dementias in people with mild cognitive impairment (MCI). Cochrane Database Syst Rev 2014;6:CD008782.
Roychaudhuri, et al. (2009) Amyloid beta protein assembly and Alzheimer disease. J. Biol. hem. 284, 4749-4753.
Sabbagh, et al. Increasing Precision of Clinical Diagnosis of Alzheimer's Disease Using a Combined Algorithm Incorporating Clinical and Novel Biomarker Data. Neurol. Therapy 6, S83-S95, 2017.
Sadler, et al., Tam, "Peptide dendrimers: Applications and synthesis," Rev. Mol. Biotechnol., vol. 90, No. 3-4, pp. 195-229, 2002.
Sakono, et al.(2010) Amyloid oligomers: Formation and toxicity of Abeta olig-omers. FEBS J 277:1348-1358.
Sato, et al. Therapeutic peptides: technological advances driving peptides into development. Curr. Opin. Biotechnol. 17, 638-642 (2006).
Schindler, et al., High-precision plasma beta-amyloid 42/40 predicts current and future brain amyloidosis. Neural., 93, e1645-e1659, 2019.
Selkoe, et al.(2001) Alzheimer's disease: Genes, proteins, and therapy. Physiol Rev 81: 741-766.
Selkoe, et al. The amyloid hypothesis of Alzheimer's disease at 25 years. EMBO Mo/. Med. 8, 595-608, 2016.
Shankar, et al. (2008) Amyloid-beta protein dimers isolated directly from Alzheimer's brains impair synaptic plasticity and memory. Nat. Med. 14, 837-842.
Shaw et al., Cerebrospinal Fluid Biomarker Signature in Alzheimer's Disease Neuroimaging Initiative Subjects. Ann. Neural. 65, 403-413, 2009.
Shea, et al., (2019) "α-Sheet secondary structure in amyloid B-peptide drives aggregation and toxicity in Alzheimer's disease." PNAS, 116(18): 8895-8900.
Silver, et al. Silver as biocides in burn and wound dressings and bacterial resistance to silver compounds. J. Ind. Microbiol. Biotechnol. 33, 627-634 (2006).
Steward, et al. Different disease-causing mutations in transthyretin trigger the same conformational conversion. Protein Eng. Des. Sel. 21, 187-195 (2008).
Sun, et al. A hydrogel biosensor for high selective and sensitive detection of amyloid-beta oligomers. Int J of Nanomed 2018;13:843-56.
Swati, et al. In vivo assessment of retinal biomarkers by hyperspectral imaging: early detection of Alzheimer's disease. ACS Chem Neuro 2019.

(56) References Cited

OTHER PUBLICATIONS

Taglialegna, et al. Amyloid Structures as Biofilm Matrix Scaffolds. J. Bacteriol. 198, 2579-2588 (2016).
Tam, et al. Disulfide bond formation in peptides by dimethyl sulfoxide. Scope and applications. J. Am. Chem. Soc. 113, 6657-6662 (1991).
Thijssen, et al. Diagnostic value of plasma phosphorylated tau181 in Alzheimer's disease and frontotemporal lobar degeneration. Nature Med. 26, 387-397, 2020.
Toledo, et al. (2013) Longitudinal change in CSF Tau and Abeta biomarkers for up to 48 months in ADNT. Acta Neuropathol. 126, 659-670.
Tomic, et al. 2009. Soluble fibrillar oligomer levels are elevated in Alzheimer's disease brain and correlate with cognitive dysfunction. Neurobio. Dis. 35,352-358, 2009.
Torii, et al (2008) Amide I infrared spectral features characteristic of some untypical conformations appearing in the structures suggested for amyloids. J Phys Chem B 112: 8737-8743.
Townsend, et al. (2006) Effects of secreted oligomers of amyloid beta-protein on hippocampal synaptic plasticity: A potent role for trimers. J. Physiol. 572, 477-492.
Tycko (2004) Progress towards a molecular-level structural understanding of amyloid fibrils. Curr Opin Struct Biol 14:96-103.
Van Rossum, et al. Biomarkers as predictors for conversion from mild cognitive impairment to Alzheimer-type dementia: implications for trial design. J Alzheimers Dis 2010;20:881-91.
Vanderstichele, et al. Standardization of measurement of beta-amyloid (1-42) in cerebrospinal fluid and plasma. Amyloid: Int. J. Exp. Clin. Invest., 1, 245-258, 2000.
Waite, et al. Polyphosphoprotein from the Adhesive Pads of Mytilus edulis †. Biochemistry 40, 2887-2893 (2001).
Walsh, et al. (2002) Naturally secreted oligomers of amyloid beta protein potently inhibit hippocampal long-term potentiation in vivo. Nature 416, 535-539.
Wang, et al.(1999) The levels of soluble versus insoluble brain Abeta distinguish Alzheimer's disease from normal and pathologic aging. Exp Neurol 158:328-337.
Wang, et al. (2002) Soluble oligomers of beta amyloid (1-42) inhibit long-term potentiation but not long-term depression in rat dentate gyrus. Brain Res. 924, 133-140.
Whitson, et al.(1989) Amyloid β protein enhances the survival of hippocampal neurons in vitro. Science 243:1488-1490.
Xu, et al. Dopamine-Induced Reduction and Functionalization of Graphene Oxide Nanosheets. Macromolecules 43, 8336 8339 (2010).
Yang, et al.(2017) Large soluble oligomers of amyloid β-protein from Alzheimer brain are far less neuroactive than the smaller oligomers to which they dissociate. J Neurosci 37:152-163.
Yang, K. et al. Polydopamine-mediated surface modification of scaffold materials for human neural stem cell engineering. Biomaterials 33, 6952-6964 (2012).
Youn, et al. Blood amyloid-beta oligomerization associated with neurodegeneration of Alzheimer's disease. Alz. Res. Ther. 11, 40, 2019.
Zahs, et al.(2013) β-Amyloid oligomers in aging and Alzheimer's disease. Front Aging Neurosci 5:28.
Zandomeneghi, et al.(2004) FTIR reveals structural differences between native B-sheet proteins and amyloid fibrils. Protein Sci 13: 3314-3321.
Zempel, et al. Abeta oligomers cause localized Ca2+ elevation, mis-sorting of endogenous tau into dendrites, tau phosphorylation, and destruction of microtubules and spines. J. Neurosci. 30, 11938-11950, 2010.
Zeng, et al. Non-proteinaceous bacterial adhesins challenge the antifouling properties of polymer brush coatings. Acta Biomater. 24, 64-73 (2015).
Zhang, et al. Predicting detection limits of enzyme linked immunosorbent assay (ELISA) and bioanalytical techniques in general. Analyst 139, 439-445 (2014).
Jiang, L. et al. Surface characteristics of mussel-inspired polydopamine coating on titanium substrates. J. Wuhan Univ. Technol.—Mater Sci Ed 29, 197-200 (2014).
Ahmed, et al. (2010) Structural conversion of neurotoxic amyloid-β(1-42) oligomers to fibrils. Nat Struct Mol Biol 17:561-567.
Alzheimer's Association. (2019). Alzheimer's disease facts and figures. [Ebook]. Chicago. Retrieved from https://www.alz.org/alzheimers-dementia/facts-figures.
Amar, et al. Amyloid-beta oligomer AW56 induces specific alterations of tau phosphorylation and neuronal signaling. Sci. Signal. 10, eaal 2021,2017.
Armen, et al.(2004) Anatomy of an amyloidogenic intermediate: Conversion of β-sheet to α-sheet structure in transthyretin at acidic pH. Structure 12: 1847-1863.
Armen, et al.(2004) Pauling and Corey's a-pleated sheet structure may define the prefibrillar amyloidogenic intermediate in amyloid disease. Proc Natl Acad Sci USA 101:11622-11627.
Armen, et al. Characterization of a possible amyloidogenic precursor in glutamine—repeat neurodegenerative diseases. Proc. Natl. Acad. Sci. U. S. A. 102, 13433-13438 (2005).
Ashe (2020) The biogenesis and biology of amyloid beta oligomers in the brain. Aiz. Demen. 16, 1561-1567.
Asker, et al. Non-eluting, surface bound enzymes disrupt surface attachment of bacteria by continuous biofilm polysaccharide degradation. Biomaterials 167, 168-176 (2018).
Balbach, et al. (2002) Supramolecular structure in full-length Alzheimer's β-amyloid fibrils: Evidence for a parallel β-sheet organization from solid-state nuclear magnetic resonance. Biophys J 83:1205-1216.
Baldeiras, et al., Addition of the Abeta42/40 ratio to the cerebrospinal fluid biomarker profile increases the predictive value for underlying Alzheimer's disease dementia in mild cognitive impairment. Alz. Res. Ther. 10, 33, 2018.
Banerjee, et al. Antifouling Coatings: Recent Developments in the Design of Surfaces That Prevent Fouling by Proteins, Bacteria, and Marine Organisms. Adv. Mater. 23, 690-718 (2011).
Barthelemy, et al. Blood plasma phosphortylated-tau isoforms track CNS change in Alzheimer's disease. J. Exp. Med. 217, e20200861, 2020.
Bernstein, et al. (2009) Amyloid-beta protein oligomerization and the importance of tetramers and dodecarners in the aetiology of Alzheimer's disease. Nat. Chem. 1, 326-331.
Bishop, et al (2004) Physiological roles of amyloid-B and implications for its removal in Alzheimer's disease. Drugs Aging 21:621-630.
Bitan, et al (2005) Neurotoxic protein oligomers: What you see is not always what you get. Amyloid 12:88-95.
Bitan, et al. (2003) Amyloid beta-protein (Abeta) assembly: Abeta 40 and Abeta 42 oligomerize through distinct pathways. Proc Natl Acad Sci USA 100:330-335.
Bleem, et al. Structural and functional diversity among amyloid proteins: Agents of disease, building blocks of biology, and implications for molecular engineering. Biotechnol. Bioeng. 114, 7-20 (2017).
Bleem, Francisco R, Bryers JD, Daggett V (2017) Designed α-sheet peptides suppress amyloid formation in Staphylococcus aureus biofilms. NPJ Biofilms Microbiomes 3:16.
Blennow. A review of fluid biomarkers for Alzheimer's Disease: Moving from CSF to blood. Neurol. Ther. 6, S15-S24, 2017.
Braak, et al. Neuropathological staging of Alzheimer-related changes. Acta Neuropath. 82, 239-259, 1991.
Breydo, et al. (2016) Structural differences between amyloid beta oligomers. Biochem Biophys Res Commun 477:700-705.
Brody, et al. Non-canonical soluble amyloid-beta aggregates and plaque buffering: controversies and future directions for target discovery in Alzheimer's disease. Alz. Res. Ther. 9, 62, 2017.
Bryers. Medical Biofilms. Biotechnol. Bioeng. 100, 1-18 (2008).
Buchhave, et al. (2012) Cerebrospinal fluid levels of beta-amyloid 1-42, but not of tau, are fully changed already 5 to 10 years before the onset of Alzheimer dementia. Arch. Gen. Psychiatry 69, 98-106.
Burchiel, et al. Accuracy of deep brain stimulation electrode placement using intraoperative computed tomography without microelectrode recording. J Neurosurg, 119, 2, 2013.

(56) References Cited

OTHER PUBLICATIONS

Busche, et al. (2020) Synergy between amyloid-beta and tau in Alzheimer's disease. Nature Neurosci. 23, 1183-1193.
Campoccia, et al. Antibiotic-loaded biomaterials and the risks for the spread of antibiotic resistance following their prophylactic and therapeutic clinical use. Biomaterials 31, 6363-6377 (2010).
Chiti, et al. (2006) Protein misfolding, functional amyloid, and human disease. Annu. Rev. Biochem. 75, 333-366.
Cline, et al. The Amyloid-beta Oligomer Hypothesis: Beginning of the Third Decade. J. Alz. Dis., 64, S567-S610, 2018.
Consensus recommendations for the postmortem diagnosis of Alzheimer's disease. The National Institute on Aging, and Reagan Institute Working Group on Diagnostic Criteria for the Neuropathological Assessment of Alzheimer's Disease. Neurobiol. Aging 18, S1-2, 1997.
Counts, et al. Biomarkers for the early detection and progression of Alzheimer's Disease. Neurother. 14, 35-53, 2017.
Daggett (2006) α-sheet: The toxic conformer in amyloid diseases? Acc Chem Res 39: 594-602.
De Strooper, (2010) Proteases and proteolysis in Alzheimer disease: a multifactorial view on the disease process. Physiol. Rev. 90, 465-494.
Defelice, et al. Alzheimer's disease—type neuronal tau hyperphosphorylation induced by Abeta oligomers. Neurobio. Aging, 29, 1334-1347, 2008.
DePas & Chapman. Microbial manipulation of the amyloid fold. Res. Microbiol. 163, 592-606 (2012).
Ding, et al. Mussel-inspired polydopamine for bio-surface functionalization. Biosurface Biotribology 2, 121-136 (2016).
Diniz, et al. Do CSF total tau, phosphorylated tau, and beta-amyloid 42 help to predict progression of mild cognitive impairment to Alzheimer's disease? A systematic review and meta-analysis of the literature. World J Biol Psychiatry 2008;9:172-82.
Drake, et al (2003) Oxidative stress precedes fibrillar deposition of Alzheimer's disease amyloid beta-peptide (1-42) in a transgenic Caenorhabditis elegans model. Neurobiol Aging 24:415-420.
Dubois, et al. Advancing research diagnostic criteria for Alzheimer's disease: the IWG-2 criteria. Lancet Neurol, 13, 614-629, 2014.
Economou, et al. (2016) Amyloid beta-protein assembly and Alzheimer's disease: Dodecamers of Abeta42, but not of Abeta40, seed fibril formation. J. Am. Chem. Soc 138, 1772-1775.
Ehrnhoefer, et al. (2008) EGCG redirects amyloidogenic polypeptides into unstructured, off-pathway oligomers. Nat. Struct. Mol. Biol. 15, 558-566.
Eshaghi, et al. Brighter Fluorescent Derivatives of UTI89 Utilizing a Monomeric vGFP. Pathogens 5, 3 (2016).
Falde, et al. Superhydrophobic materials for biomedical applications. Biomaterials 104, 87-103 (2016).
Ferreira, et al. Improving CSF biomarkers' performance for predicting progression from mild cognitive impairment to Alzheimer's disease by considering different confounding factors: a meta-analysis. Front Aging Neurosci 2014;6:287.
Ferreira, et al. Rate of cognitive decline in relation to sex after 60 years-of-age: a systematic review. Geratr Gerontol Int 2014;14:23-31.
Flores-Mireles, et al. EbpA vaccine antibodies block binding of Enterococcus faecalis to fibrinogen to prevent catheter—associated bladder infection in mice. Sci. Transl. Med. 6, 254ra127-254ra127 (2014).
Forier, et al. Lipid and polymer nanoparticles for drug delivery to bacterial biofilms. J. Controlled Release 190, 607-623 (2014).
Forlenza, et al. (2015) Cerebrospinal fluid biomarkers in Alzheimer's disease: Diagnostic accuracy and prediction of dementia Alz. & Dem.: Diagnosis, Assessment & Dis. Monitoring J, 455-463.
Frydman-Marom, et al. (2009) Cognitive-performance recovery of Alzheimer's disease model mice by modulation of early soluble amyloidal assemblies. Angew Chem Int Ed Engl 48:1981-1986.
Gilabert-Porres, et al. Design of a Nanostructured Active Surface against Gram Positive and Gram-Negative Bacteria through Plasma Activation and in Situ Silver Reduction. ACS Appl. Mater. Interfaces 8, 64-73 (2016).
Giuffrida, et al. (2010) The monomer state of β-amyloid: Where the Alzheimer's disease protein meets physiology. Rev Neurosci 21:83-93.
Glabe, (2008) Structural classification of toxic amyloid oligomers. J Biol. Chem. 283, 29639-29643.
Glenner, et al.(1984) The amyloid deposits in Alzheimer's disease: Their nature and pathogenesis. Appl Pathol 2:357-369.
Goddard, et al. Polymer surface modification for the attachment of bioactive compounds. Prog. Polym. Sci. 32, 698-725 (2007).
Greenberg, et al. Diagnosis of cerebral amyloid angiopathy. Sensitivity and specificity of cortical biopsy. Stroke 28, 1418-1422, 1997.
Gruenheid, et al. Resistance to antimicrobial peptides in Gram-negative bacteria. FEMS Microbiol. Lett. 330, 81-89 (2012).
Haass, et al. (2007) Soluble protein oligomers in neurodegeneration: Lessons from the Alzheimer's amyloid β-peptide. Nat Rev Mol Cell Biol 8:101-112.
Hansson, et al. Advantages and disadvantages of the use of the CSF amyloid beta 42/40 ratio in the diagnosis of Alzheimer's Disease. Alz. Res. & Ther. 11, 34, 2019.
Hardy, et al. (1992) Alzheimer's disease: the amyloid cascade hypothesis. Science 256, 184-185.
Hassan, et al (2015) Identifying Aβ-specific pathogenic mechanisms using a nematode model of Alzheimer's disease. Neurobiol Aging 36:857-866.
Herigstad, et al. How to optimize the drop plate method for enumerating bacteria. J. Microbiol. Methods 44, 121-129 (2001).
Herukka, et al. Recommendations for cerebrospinal fluid Alzheimer's disease biomarkers in the diagnostic evaluation of mild cognitive impairment. Alz & Dem 2017;13:285-95.
Hilaire, et al (2018) Possible existence of a-sheets in the amyloid fibrils formed by a TTR105-115 mutant. J Am Chem Soc 140:629-635.
Hiltunen, et al (2009) Functional roles of amyloid-beta protein precursor and amyloid-beta peptides: Evidence from experimental studies. J Alzheimers Dis 18:401-412.
Tixson et al. Restriction isotyping of human apolipoprotein E by gene amplification and cleavage with Hhal. J Lipid Res. 1990;31 (3): 545-548.
Hong et al., Diffusible, highly bioactive oligomers represent a critical minority of soluble Aβ in Alzheimer's disease brain. Acta. Neuropath. 136, 19-40, 2018.
Hopping, et al. (2014) Designed α-sheet peptides inhibit amyloid formation by targeting toxic oligomers. eLife 3: e01681.
Hisia, et al. Plaque-independent disruption of neural circuits in Alzheimer's disease mouse models. Proc. Natl. Acad. Sci. USA 96, 3228-3233, 1999.
Hu, et al. A peptide probe for detection of various beta-amyloid oligomers. Mol Biosyst 2012;8:2741-52.
Huang, et al. (2000) Structural studies of soluble oligomers of the Alzheimer etaamyloid peptide. J Mol Biol 297:73-87.
Jack Jr., et al. Tracking pathophysiological processes in Alzheimer's disease: An updated hypothetical model of dynamic biomarkers. Neurology 12, 207-216, 2013.
Janelidze, et al. Cerebrospinal fluid p-tau217 performs better than p-tau181 as a biomarker of Alzheimer's disease. Nature Commun. 11, 1683, 2020.
Janelidze, et al., Plasma beta-amyloid in Alzheimer's disease and vascular disease. Sci. Rep. 6, 26801,2016.
Janelidze, et al., Plasma P-tau181 in Alzheimer's disease: Relationship to other biomarkers, differential diagnosis. neuropathology and longitudinal progression to Alzheimer's dementia. Nat Med. 26. 379-386, 2020.
Jarrett, et al. (1993) The carboxy terminus of the beta amyloid protein is critical for the seeding of amyloid formation: Implications for the pathogenesis of Alzheimer's disease. Biochemistry 32, 4693-4697.
Jaunmuktane, et al. (2015) Evidence for human transmission of amyloid-β pathology and cerebral amyloid angiopathy Nature 525, 247-250.

(56) References Cited

OTHER PUBLICATIONS

Lesne, et al. (2013) Brain amyloid-β oligomers in ageing and Alzheimer's disease. Brain 136:1383-1398.

Kang, et al. One-Step Modification of Superhydrophobic Surfaces by a Mussel Inspired Polymer Coating. Angew. Chem. Int. Ed. 49, 9401-9404 (2010).

Kayed, et al. (2003) Common structure of soluble amyloid oligomers implies common mechanism of pathogenesis. Science 300:486-489.

Kellock, Hopping G, Caughey B, Daggett V (2016) Peptides composed of alternating L- and D-amino acids inhibit amyloidogenesis in three distinct amyloid systems independent of sequence. J Mol Biol 428:2317-2328.

Khatoon, et al. Bacterial biofilm formation on implantable devices and approaches to its treatment and prevention. Heliyon 4, e01067 (2018).

Kim, et al. Clinically accurate diagnosis of Alzheimer's disease via multiplexed sensing of core biomarkers in human plasma. Nat Commun 11, 119, 2020.

Kim, et al., Human Lilr82 is a beta-amyloid receptor and its murine homolog PirB regulates synaptic plasticity in an Alzheimer's model. Science, 341, 1399-1404, 2013.

Kinoshita, et al. (2003) Demonstration by FRET of BACE interaction with the amyloid precursor protein at the cell surface and in early endosomes. J Cell Sci. 116, 3339-3346.

Kirschner, et al (1986) X-ray diffraction from intraneuronal paired helical filaments and extraneuronal amyloid fibers in Alzheimer disease indicates cross-B conformation. Proc Natl Acad Sci USA 83:503-507.

Klein, et al (2001) Targeting small Abeta oligomers: The solution to an Alzheimer's disease conundrum? Trends Neurosci 24:219-224.

Koo, et al. Targeting microbial biofilms: current and prospective therapeutic strategies. Nat. Rev. Microbiol. 15, 740-755 (2017).

Koudinov, et al (2004) Alzheimer's amyloid-β (A β) is an essential synaptic protein, not neurotoxic junk. Acta Neurobiol Exp (Warsz) 64:71-79.

Kumar, et al. (2011) Extracellular phosphorylation of the amyloid beta-peptide promotes formation of toxic aggregates during the pathogenesis of Alzheimer's disease. EMBO J. 30, 2255-2265.

Kuo, et al. (2000) Elevated A B and apolipoprotein E in A betaPP transgenic mice and its relationship to amyloid accumulation in Alzheimer's disease. Mol Med 6:430-439.

Adiwala, et al. (2011) Aromatic small molecules remodel toxic soluble oligomers of amyloid beta through three independent pathways. J Biol. Chem. 286, 3209-3218.

Lambert, et al. (1998) Diffusible, nonfibrillar ligands derived from Abeta1-42 are potent central nervous system neurotoxins. Proc Natl Acad Sci USA 95:6448-6453.

Ambert, et al. (2001) Vaccination with soluble Abeta oligomers generates toxicity-neutralizing antibodies. J Neurochem 79:595-605.

Laske, et al. Innovative diagnostic tools for early detection of Alzheimer's disease. Alz & Dement 2015;11:561-78.

Lee, et al. (2011) Amyloid-beta forms fibrils by nucleated conformational conversion of oligomers. Nat. hem. Biol. 7, 602-609.

Lee, et al. Mussel-Inspired Surface Chemistry for Multifunctional Coatings. Science 318, 426-430 (2007).

Lee, et al. Polydopamine—mediated immobilization of multiple bioactive molecules for the development of functional vascular graft materials. Biomaterials 33, 8343-8352 (2012).

Lesné, et al.(2008) Plaque-bearing mice with reduced levels of oligomeric amyloid-beta assemblies have intact memory function. Neuroscience 151: 745-749.

Lesné, et al. (2006) A specific amyloid-beta protein assembly in the brain impairs memory. Nature 440:352-357.

\* cited by examiner

SEQUENCE LISTING

<160> NUMBER OF SEQ ID NOS: 67

<210> SEQ ID NO 1
<211> LENGTH: 23
<212> TYPE: PRT
<213> ORGANISM: Artificial Sequence
<220> FEATURE:
<223> OTHER INFORMATION: Synthetic

<400> SEQUENCE: 1

Arg Gly Asn Trp Asn Glu Ser Lys Met Asn Glu Tyr Ser Gly Trp Met

```
                1               5                   10                  15

Leu Met Cys Thr Met Gly Arg
            20

<210> SEQ ID NO 2
<211> LENGTH: 23
<212> TYPE: PRT
<213> ORGANISM: Artificial Sequence
<220> FEATURE:
<223> OTHER INFORMATION: Synthetic

<400> SEQUENCE: 2

Arg Gly Asn Trp Asn Glu Ser Lys Met Asn Glu Tyr Tyr Gly Trp Met
1               5                   10                  15

Leu Met Cys Thr Met Gly Arg
            20

<210> SEQ ID NO 3
<211> LENGTH: 23
<212> TYPE: PRT
<213> ORGANISM: Artificial Sequence
<220> FEATURE:
<223> OTHER INFORMATION: Synthetic

<400> SEQUENCE: 3

Arg Gly Asn Trp Asn Glu Ser Lys Met Asn Glu Tyr Tyr Gly Trp Met
1               5                   10                  15

Leu Met Cys Thr Met Gly Arg
            20

<210> SEQ ID NO 4
<211> LENGTH: 23
<212> TYPE: PRT
<213> ORGANISM: Artificial Sequence
<220> FEATURE:
<223> OTHER INFORMATION: Synthetic

<400> SEQUENCE: 4

Arg Gly Asn Trp Asn Glu Ser Lys Met Asn Glu Tyr Tyr Gly Trp Met
1               5                   10                  15

Leu Met Thr Cys Met Gly Arg
            20

<210> SEQ ID NO 5
<211> LENGTH: 23
<212> TYPE: PRT
<213> ORGANISM: Artificial Sequence
<220> FEATURE:
<223> OTHER INFORMATION: Synthetic

<400> SEQUENCE: 5

Arg Gly Asn Cys Asn Glu Ser Lys Met Asn Glu Tyr Tyr Gly Trp Met
1               5                   10                  15

Leu Met Leu Thr Met Gly Arg
            20

<210> SEQ ID NO 6
<211> LENGTH: 23
<212> TYPE: PRT
<213> ORGANISM: Artificial Sequence
<220> FEATURE:
<223> OTHER INFORMATION: Synthetic

<400> SEQUENCE: 6
```

Arg Gly Asn Trp Cys Glu Ser Lys Met Asn Glu Tyr Tyr Gly Trp Met
1               5                   10                  15

Leu Met Leu Thr Met Gly Arg
            20

<210> SEQ ID NO 7
<211> LENGTH: 23
<212> TYPE: PRT
<213> ORGANISM: Artificial Sequence
<220> FEATURE:
<223> OTHER INFORMATION: Synthetic

<400> SEQUENCE: 7

Arg Gly Asn Trp Asn Glu Ser Lys Met Asn Glu Tyr Tyr Gly Trp Met
1               5                   10                  15

Leu Met Cys Thr Met Gly Arg
            20

<210> SEQ ID NO 8
<211> LENGTH: 23
<212> TYPE: PRT
<213> ORGANISM: Artificial Sequence
<220> FEATURE:
<223> OTHER INFORMATION: Synthetic

<400> SEQUENCE: 8

Arg Gly Glu Met Asn Tyr Phe Trp Met Asn Glu Tyr Tyr Gly Trp Thr
1               5                   10                  15

Met Asn Cys Lys Met Gly Arg
            20

<210> SEQ ID NO 9
<211> LENGTH: 23
<212> TYPE: PRT
<213> ORGANISM: Artificial Sequence
<220> FEATURE:
<223> OTHER INFORMATION: Synthetic

<400> SEQUENCE: 9

Arg Gly Glu Met Asn Tyr Phe Trp Met Asn Glu Tyr Tyr Gly Trp Thr
1               5                   10                  15

Met Asn Cys Lys Met Gly Arg
            20

<210> SEQ ID NO 10
<211> LENGTH: 23
<212> TYPE: PRT
<213> ORGANISM: Artificial Sequence
<220> FEATURE:
<223> OTHER INFORMATION: Synthetic

<400> SEQUENCE: 10

Arg Gly Glu Met Asn Leu Ser Trp Met Asn Glu Tyr Ser Gly Trp Thr
1               5                   10                  15

Met Asn Cys Lys Met Gly Arg
            20

<210> SEQ ID NO 11
<211> LENGTH: 23
<212> TYPE: PRT
<213> ORGANISM: Artificial Sequence
<220> FEATURE:
<223> OTHER INFORMATION: Synthetic

<400> SEQUENCE: 11

Arg Gly Glu Cys Asn Leu Ser Trp Met Asn Glu Tyr Ser Gly Trp Thr
1               5                   10                  15

Met Asn Met Lys Met Gly Arg
            20

<210> SEQ ID NO 12
<211> LENGTH: 23
<212> TYPE: PRT
<213> ORGANISM: Artificial Sequence
<220> FEATURE:
<223> OTHER INFORMATION: Synthetic

<400> SEQUENCE: 12

Arg Gly Glu Cys Asn Leu Ser Trp Met Asn Glu Tyr Tyr Gly Trp Thr
1               5                   10                  15

Met Asn Met Lys Met Gly Arg
            20

<210> SEQ ID NO 13
<211> LENGTH: 23
<212> TYPE: PRT
<213> ORGANISM: Artificial Sequence
<220> FEATURE:
<223> OTHER INFORMATION: Synthetic

<400> SEQUENCE: 13

Arg Gly Glu Cys Asn Leu Ser Trp Met Asn Glu Tyr Tyr Gly Trp Thr
1               5                   10                  15

Met Asn Met Lys Met Gly Arg
            20

<210> SEQ ID NO 14
<211> LENGTH: 23
<212> TYPE: PRT
<213> ORGANISM: Artificial Sequence
<220> FEATURE:
<223> OTHER INFORMATION: Synthetic

<400> SEQUENCE: 14

Arg Cys Glu Met Asn Leu Ser Trp Met Asn Glu Tyr Tyr Gly Trp Thr
1               5                   10                  15

Met Asn Met Lys Met Gly Arg
            20

<210> SEQ ID NO 15
<211> LENGTH: 23
<212> TYPE: PRT
<213> ORGANISM: Artificial Sequence
<220> FEATURE:
<223> OTHER INFORMATION: Synthetic

<400> SEQUENCE: 15

Arg Gly Glu Met Asn Leu Ser Trp Met Asn Glu Tyr Tyr Gly Trp Thr
1               5                   10                  15

Met Asn Met Lys Cys Gly Arg
            20

<210> SEQ ID NO 16
<211> LENGTH: 23
<212> TYPE: PRT
<213> ORGANISM: Artificial Sequence
<220> FEATURE:
<223> OTHER INFORMATION: Synthetic

```
<400> SEQUENCE: 16

Arg Gly Glu Cys Asn Tyr Phe Trp Met Asn Glu Tyr Tyr Gly Trp Thr
1               5                   10                  15

Met Asn Met Arg Met Gly Lys
            20

<210> SEQ ID NO 17
<211> LENGTH: 23
<212> TYPE: PRT
<213> ORGANISM: Artificial Sequence
<220> FEATURE:
<223> OTHER INFORMATION: Synthetic

<400> SEQUENCE: 17

Arg Gly Glu Cys Asn Tyr Phe Trp Met Asn Glu Tyr Tyr Gly Trp Thr
1               5                   10                  15

Met Asn Met Arg Asx Gly Lys
            20

<210> SEQ ID NO 18
<211> LENGTH: 23
<212> TYPE: PRT
<213> ORGANISM: Artificial Sequence
<220> FEATURE:
<223> OTHER INFORMATION: Synthetic

<400> SEQUENCE: 18

Arg Gly Glu Met Cys Tyr Phe Trp Met Asn Glu Tyr Tyr Gly Trp Thr
1               5                   10                  15

Met Asn Met Arg Asx Gly Lys
            20

<210> SEQ ID NO 19
<211> LENGTH: 23
<212> TYPE: PRT
<213> ORGANISM: Artificial Sequence
<220> FEATURE:
<223> OTHER INFORMATION: Synthetic

<400> SEQUENCE: 19

Arg Gly Glu Asx Asn Tyr Phe Trp Met Asn Glu Tyr Tyr Gly Trp Thr
1               5                   10                  15

Met Asn Met Arg Cys Gly Lys
            20

<210> SEQ ID NO 20
<211> LENGTH: 23
<212> TYPE: PRT
<213> ORGANISM: Artificial Sequence
<220> FEATURE:
<223> OTHER INFORMATION: Synthetic

<400> SEQUENCE: 20

Arg Gly Glu Asx Asn Tyr Phe Trp Met Asn Glu Tyr Tyr Gly Trp Thr
1               5                   10                  15

Met Asn Met Cys Arg Gly Lys
            20

<210> SEQ ID NO 21
<211> LENGTH: 23
<212> TYPE: PRT
<213> ORGANISM: Artificial Sequence
<220> FEATURE:
<223> OTHER INFORMATION: Synthetic
```

```
<400> SEQUENCE: 21

Arg Gly Glu Tyr Asn Cys Phe Trp Met Asn Glu Tyr Tyr Gly Trp Thr
1               5                   10                  15

Met Asn Met Arg Met Gly Lys
            20

<210> SEQ ID NO 22
<211> LENGTH: 23
<212> TYPE: PRT
<213> ORGANISM: Artificial Sequence
<220> FEATURE:
<223> OTHER INFORMATION: Synthetic

<400> SEQUENCE: 22

Arg Gly Glu Leu Asn Tyr Phe Trp Met Asn Glu Tyr Tyr Gly Trp Thr
1               5                   10                  15

Cys Asn Met Arg Met Gly Lys
            20

<210> SEQ ID NO 23
<211> LENGTH: 23
<212> TYPE: PRT
<213> ORGANISM: Artificial Sequence
<220> FEATURE:
<223> OTHER INFORMATION: Synthetic

<400> SEQUENCE: 23

Arg Gly Glu Leu Asn Tyr Phe Trp Met Asn Glu Cys Tyr Gly Trp Thr
1               5                   10                  15

Met Asn Met Arg Met Gly Lys
            20

<210> SEQ ID NO 24
<211> LENGTH: 23
<212> TYPE: PRT
<213> ORGANISM: Artificial Sequence
<220> FEATURE:
<223> OTHER INFORMATION: Synthetic

<400> SEQUENCE: 24

Arg Gly Glu Met Asn Leu Ser Trp Met Asn Glu Tyr Ser Gly Trp Thr
1               5                   10                  15

Met Asn Cys Lys Met Gly Arg
            20

<210> SEQ ID NO 25
<211> LENGTH: 23
<212> TYPE: PRT
<213> ORGANISM: Artificial Sequence
<220> FEATURE:
<223> OTHER INFORMATION: Synthetic

<400> SEQUENCE: 25

Arg Gly Glu Met Asn Leu Ser Trp Met Asn Glu Tyr Tyr Gly Trp Thr
1               5                   10                  15

Met Asn Met Lys Cys Gly Arg
            20

<210> SEQ ID NO 26
<211> LENGTH: 23
<212> TYPE: PRT
<213> ORGANISM: Artificial Sequence
<220> FEATURE:
```

<223> OTHER INFORMATION: Synthetic

<400> SEQUENCE: 26

Arg Gly Glu Met Asn Tyr Phe Trp Met Asn Glu Tyr Tyr Gly Trp Thr
1               5                   10                  15
Met Asn Cys Lys Ala Gly Arg
            20

<210> SEQ ID NO 27
<211> LENGTH: 23
<212> TYPE: PRT
<213> ORGANISM: Artificial Sequence
<220> FEATURE:
<223> OTHER INFORMATION: Synthetic

<400> SEQUENCE: 27

Arg Gly Glu Met Asn Tyr Phe Trp Met Asn Glu Tyr Tyr Gly Trp Thr
1               5                   10                  15
Ala Asn Cys Lys Ala Gly Arg
            20

<210> SEQ ID NO 28
<211> LENGTH: 23
<212> TYPE: PRT
<213> ORGANISM: Artificial Sequence
<220> FEATURE:
<223> OTHER INFORMATION: Synthetic

<400> SEQUENCE: 28

Arg Gly Glu Met Asn Tyr Phe Trp Met Asn Glu Tyr Tyr Gly Trp Thr
1               5                   10                  15
Ala Asn Cys Lys Met Gly Arg
            20

<210> SEQ ID NO 29
<211> LENGTH: 23
<212> TYPE: PRT
<213> ORGANISM: Artificial Sequence
<220> FEATURE:
<223> OTHER INFORMATION: Synthetic

<400> SEQUENCE: 29

Arg Gly Glu Met Asn Tyr Phe Trp Met Asn Glu Tyr Tyr Gly Trp Thr
1               5                   10                  15
Leu Asn Cys Lys Val Gly Arg
            20

<210> SEQ ID NO 30
<211> LENGTH: 23
<212> TYPE: PRT
<213> ORGANISM: Artificial Sequence
<220> FEATURE:
<223> OTHER INFORMATION: Synthetic

<400> SEQUENCE: 30

Arg Gly Glu Met Asn Tyr Phe Trp Met Asn Glu Tyr Tyr Gly Trp Thr
1               5                   10                  15
Val Asn Cys Lys Leu Gly Arg
            20

<210> SEQ ID NO 31
<211> LENGTH: 23
<212> TYPE: PRT
<213> ORGANISM: Artificial Sequence

```
<220> FEATURE:
<223> OTHER INFORMATION: Synthetic

<400> SEQUENCE: 31

Arg Gly Glu Met Asn Leu Ser Trp Met Asn Glu Tyr Ser Gly Trp Thr
1               5                   10                  15
Met Asn Leu Lys Met Gly Arg
            20

<210> SEQ ID NO 32
<211> LENGTH: 23
<212> TYPE: PRT
<213> ORGANISM: Artificial Sequence
<220> FEATURE:
<223> OTHER INFORMATION: Synthetic

<400> SEQUENCE: 32

Arg Gly Asn Trp Asn Glu Ser Lys Met Asn Glu Tyr Ser Gly Trp Met
1               5                   10                  15
Leu Met Cys Thr Met Gly Arg
            20

<210> SEQ ID NO 33
<211> LENGTH: 23
<212> TYPE: PRT
<213> ORGANISM: Artificial Sequence
<220> FEATURE:
<223> OTHER INFORMATION: Synthetic

<400> SEQUENCE: 33

Arg Gly Asn Trp Asn Glu Ser Lys Met Asn Glu Tyr Tyr Gly Trp Met
1               5                   10                  15
Leu Met Cys Thr Met Gly Arg
            20

<210> SEQ ID NO 34
<211> LENGTH: 23
<212> TYPE: PRT
<213> ORGANISM: Artificial Sequence
<220> FEATURE:
<223> OTHER INFORMATION: Synthetic

<400> SEQUENCE: 34

Arg Gly Asn Trp Asn Glu Ser Lys Met Asn Glu Tyr Tyr Gly Trp Met
1               5                   10                  15
Leu Met Cys Thr Met Gly Arg
            20

<210> SEQ ID NO 35
<211> LENGTH: 23
<212> TYPE: PRT
<213> ORGANISM: Artificial Sequence
<220> FEATURE:
<223> OTHER INFORMATION: Synthetic

<400> SEQUENCE: 35

Arg Gly Asn Trp Asn Glu Ser Lys Met Asn Glu Tyr Tyr Gly Trp Met
1               5                   10                  15
Leu Met Thr Cys Met Gly Arg
            20

<210> SEQ ID NO 36
<211> LENGTH: 23
<212> TYPE: PRT
```

```
<213> ORGANISM: Artificial Sequence
<220> FEATURE:
<223> OTHER INFORMATION: Synthetic

<400> SEQUENCE: 36

Arg Gly Asn Cys Asn Glu Ser Lys Met Asn Glu Tyr Tyr Gly Trp Met
1               5                   10                  15

Leu Met Leu Thr Met Gly Arg
            20

<210> SEQ ID NO 37
<211> LENGTH: 23
<212> TYPE: PRT
<213> ORGANISM: Artificial Sequence
<220> FEATURE:
<223> OTHER INFORMATION: Synthetic

<400> SEQUENCE: 37

Arg Gly Asn Trp Cys Glu Ser Lys Met Asn Glu Tyr Tyr Gly Trp Met
1               5                   10                  15

Leu Met Leu Thr Met Gly Arg
            20

<210> SEQ ID NO 38
<211> LENGTH: 23
<212> TYPE: PRT
<213> ORGANISM: Artificial Sequence
<220> FEATURE:
<223> OTHER INFORMATION: Synthetic

<400> SEQUENCE: 38

Arg Gly Asn Trp Asn Glu Ser Lys Met Asn Glu Tyr Tyr Gly Trp Met
1               5                   10                  15

Leu Met Cys Thr Met Gly Arg
            20

<210> SEQ ID NO 39
<211> LENGTH: 23
<212> TYPE: PRT
<213> ORGANISM: Artificial Sequence
<220> FEATURE:
<223> OTHER INFORMATION: Synthetic

<400> SEQUENCE: 39

Arg Gly Glu Met Asn Tyr Phe Trp Met Asn Glu Tyr Tyr Gly Trp Thr
1               5                   10                  15

Met Asn Cys Lys Met Gly Arg
            20

<210> SEQ ID NO 40
<211> LENGTH: 23
<212> TYPE: PRT
<213> ORGANISM: Artificial Sequence
<220> FEATURE:
<223> OTHER INFORMATION: Synthetic

<400> SEQUENCE: 40

Arg Gly Glu Met Asn Tyr Phe Trp Met Asn Glu Tyr Tyr Gly Trp Thr
1               5                   10                  15

Met Asn Cys Lys Met Gly Arg
            20

<210> SEQ ID NO 41
<211> LENGTH: 23
```

```
<212> TYPE: PRT
<213> ORGANISM: Artificial Sequence
<220> FEATURE:
<223> OTHER INFORMATION: Synthetic

<400> SEQUENCE: 41

Arg Gly Glu Met Asn Leu Ser Trp Met Asn Glu Tyr Ser Gly Trp Thr
1               5                   10                  15

Met Asn Cys Lys Met Gly Arg
            20

<210> SEQ ID NO 42
<211> LENGTH: 23
<212> TYPE: PRT
<213> ORGANISM: Artificial Sequence
<220> FEATURE:
<223> OTHER INFORMATION: Synthetic

<400> SEQUENCE: 42

Arg Gly Glu Cys Asn Leu Ser Trp Met Asn Glu Tyr Ser Gly Trp Thr
1               5                   10                  15

Met Asn Met Lys Met Gly Arg
            20

<210> SEQ ID NO 43
<211> LENGTH: 23
<212> TYPE: PRT
<213> ORGANISM: Artificial Sequence
<220> FEATURE:
<223> OTHER INFORMATION: Synthetic

<400> SEQUENCE: 43

Arg Gly Glu Cys Asn Leu Ser Trp Met Asn Glu Tyr Tyr Gly Trp Thr
1               5                   10                  15

Met Asn Met Lys Met Gly Arg
            20

<210> SEQ ID NO 44
<211> LENGTH: 23
<212> TYPE: PRT
<213> ORGANISM: Artificial Sequence
<220> FEATURE:
<223> OTHER INFORMATION: Synthetic

<400> SEQUENCE: 44

Arg Gly Glu Cys Asn Leu Ser Trp Met Asn Glu Tyr Tyr Gly Trp Thr
1               5                   10                  15

Met Asn Met Lys Met Gly Arg
            20

<210> SEQ ID NO 45
<211> LENGTH: 23
<212> TYPE: PRT
<213> ORGANISM: Artificial Sequence
<220> FEATURE:
<223> OTHER INFORMATION: Synthetic

<400> SEQUENCE: 45

Arg Cys Glu Met Asn Leu Ser Trp Met Asn Glu Tyr Tyr Gly Trp Thr
1               5                   10                  15

Met Asn Met Lys Met Gly Arg
            20

<210> SEQ ID NO 46
```

```
<211> LENGTH: 23
<212> TYPE: PRT
<213> ORGANISM: Artificial Sequence
<220> FEATURE:
<223> OTHER INFORMATION: Synthetic

<400> SEQUENCE: 46

Arg Gly Glu Met Asn Leu Ser Trp Met Asn Glu Tyr Tyr Gly Trp Thr
1               5                   10                  15

Met Asn Met Lys Cys Gly Arg
            20

<210> SEQ ID NO 47
<211> LENGTH: 23
<212> TYPE: PRT
<213> ORGANISM: Artificial Sequence
<220> FEATURE:
<223> OTHER INFORMATION: Synthetic

<400> SEQUENCE: 47

Arg Gly Glu Met Asn Leu Ser Trp Met Asn Glu Tyr Ser Gly Trp Thr
1               5                   10                  15

Met Asn Cys Lys Met Gly Arg
            20

<210> SEQ ID NO 48
<211> LENGTH: 23
<212> TYPE: PRT
<213> ORGANISM: Artificial Sequence
<220> FEATURE:
<223> OTHER INFORMATION: Synthetic

<400> SEQUENCE: 48

Arg Gly Glu Met Asn Leu Ser Trp Met Asn Glu Tyr Tyr Gly Trp Thr
1               5                   10                  15

Met Asn Met Lys Cys Gly Arg
            20

<210> SEQ ID NO 49
<211> LENGTH: 23
<212> TYPE: PRT
<213> ORGANISM: Artificial Sequence
<220> FEATURE:
<223> OTHER INFORMATION: Synthetic

<400> SEQUENCE: 49

Arg Gly Glu Cys Asn Tyr Phe Trp Met Asn Glu Tyr Tyr Gly Trp Thr
1               5                   10                  15

Met Asn Met Arg Met Gly Lys
            20

<210> SEQ ID NO 50
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: Xaa can be any naturally occurring amino acid

<400> SEQUENCE: 50

Arg Gly Glu Cys Asn Tyr Phe Trp Met Asn Glu Tyr Tyr Gly Trp Thr
1               5                   10                  15
```

```
Met Asn Met Arg Xaa Gly Lys
            20

<210> SEQ ID NO 51
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: Xaa can be any naturally occurring amino acid

<400> SEQUENCE: 51

Arg Gly Glu Met Cys Tyr Phe Trp Met Asn Glu Tyr Tyr Gly Trp Thr
1               5                   10                  15

Met Asn Met Arg Xaa Gly Lys
            20

<210> SEQ ID NO 52
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa can be any naturally occurring amino acid

<400> SEQUENCE: 52

Arg Gly Glu Xaa Asn Tyr Phe Trp Met Asn Glu Tyr Tyr Gly Trp Thr
1               5                   10                  15

Met Asn Met Arg Cys Gly Lys
            20

<210> SEQ ID NO 53
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa can be any naturally occurring amino acid

<400> SEQUENCE: 53

Arg Gly Glu Xaa Asn Tyr Phe Trp Met Asn Glu Tyr Tyr Gly Trp Thr
1               5                   10                  15

Met Asn Met Cys Arg Gly Lys
            20

<210> SEQ ID NO 54
<211> LENGTH: 23
<212> TYPE: PRT
<213> ORGANISM: Artificial Sequence
<220> FEATURE:
<223> OTHER INFORMATION: Synthetic

<400> SEQUENCE: 54

Arg Gly Glu Tyr Asn Cys Phe Trp Met Asn Glu Tyr Tyr Gly Trp Thr
1               5                   10                  15

Met Asn Met Arg Met Gly Lys
            20
```

```
<210> SEQ ID NO 55
<211> LENGTH: 23
<212> TYPE: PRT
<213> ORGANISM: Artificial Sequence
<220> FEATURE:
<223> OTHER INFORMATION: Synthetic

<400> SEQUENCE: 55

Arg Gly Glu Leu Asn Tyr Phe Trp Met Asn Glu Tyr Tyr Gly Trp Thr
1               5                   10                  15

Cys Asn Met Arg Met Gly Lys
            20

<210> SEQ ID NO 56
<211> LENGTH: 23
<212> TYPE: PRT
<213> ORGANISM: Artificial Sequence
<220> FEATURE:
<223> OTHER INFORMATION: Synthetic

<400> SEQUENCE: 56

Arg Gly Glu Leu Asn Tyr Phe Trp Met Asn Glu Cys Tyr Gly Trp Thr
1               5                   10                  15

Met Asn Met Arg Met Gly Lys
            20

<210> SEQ ID NO 57
<211> LENGTH: 23
<212> TYPE: PRT
<213> ORGANISM: Artificial Sequence
<220> FEATURE:
<223> OTHER INFORMATION: Synthetic

<400> SEQUENCE: 57

Arg Gly Glu Met Asn Tyr Phe Trp Met Asn Glu Tyr Tyr Gly Trp Thr
1               5                   10                  15

Met Asn Cys Lys Ala Gly Arg
            20

<210> SEQ ID NO 58
<211> LENGTH: 23
<212> TYPE: PRT
<213> ORGANISM: Artificial Sequence
<220> FEATURE:
<223> OTHER INFORMATION: Synthetic

<400> SEQUENCE: 58

Arg Gly Glu Met Asn Tyr Phe Trp Met Asn Glu Tyr Tyr Gly Trp Thr
1               5                   10                  15

Ala Asn Cys Lys Ala Gly Arg
            20

<210> SEQ ID NO 59
<211> LENGTH: 23
<212> TYPE: PRT
<213> ORGANISM: Artificial Sequence
<220> FEATURE:
<223> OTHER INFORMATION: Synthetic

<400> SEQUENCE: 59

Arg Gly Glu Met Asn Tyr Phe Trp Met Asn Glu Tyr Tyr Gly Trp Thr
1               5                   10                  15

Ala Asn Cys Lys Met Gly Arg
            20
```

```
<210> SEQ ID NO 60
<211> LENGTH: 23
<212> TYPE: PRT
<213> ORGANISM: Artificial Sequence
<220> FEATURE:
<223> OTHER INFORMATION: Synthetic

<400> SEQUENCE: 60

Arg Gly Glu Met Asn Tyr Phe Trp Met Asn Glu Tyr Tyr Gly Trp Thr
1               5                   10                  15

Leu Asn Cys Lys Val Gly Arg
            20

<210> SEQ ID NO 61
<211> LENGTH: 23
<212> TYPE: PRT
<213> ORGANISM: Artificial Sequence
<220> FEATURE:
<223> OTHER INFORMATION: Synthetic

<400> SEQUENCE: 61

Arg Gly Glu Met Asn Tyr Phe Trp Met Asn Glu Tyr Tyr Gly Trp Thr
1               5                   10                  15

Val Asn Cys Lys Leu Gly Arg
            20

<210> SEQ ID NO 62
<211> LENGTH: 7
<212> TYPE: PRT
<213> ORGANISM: Artificial Sequence
<220> FEATURE:
<223> OTHER INFORMATION: Synthetic

<400> SEQUENCE: 62

Asn Trp Asn Glu Ser Lys Met
1               5

<210> SEQ ID NO 63
<211> LENGTH: 5
<212> TYPE: PRT
<213> ORGANISM: Artificial Sequence
<220> FEATURE:
<223> OTHER INFORMATION: Synthetic

<400> SEQUENCE: 63

Asn Glu Tyr Ser Gly
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic

<400> SEQUENCE: 64

Trp Met Leu Met Cys Thr Met
1               5

<210> SEQ ID NO 65
<211> LENGTH: 23
<212> TYPE: PRT
<213> ORGANISM: Artificial Sequence
<220> FEATURE:
<223> OTHER INFORMATION: Synthetic
```

```
<400> SEQUENCE: 65

Arg Gly Asn Trp Asn Glu Ser Lys Met Asn Glu Tyr Tyr Gly Trp Met
1               5                   10                  15

Leu Met Cys Thr Met Gly Arg
            20

<210> SEQ ID NO 66
<211> LENGTH: 9
<212> TYPE: PRT
<213> ORGANISM: Artificial Sequence
<220> FEATURE:
<223> OTHER INFORMATION: Synthetic

<400> SEQUENCE: 66

Arg Gly Asn Trp Asn Glu Ser Lys Met
1               5

<210> SEQ ID NO 67
<211> LENGTH: 11
<212> TYPE: PRT
<213> ORGANISM: Artificial Sequence
<220> FEATURE:
<223> OTHER INFORMATION: Synthetic

<400> SEQUENCE: 67

Tyr Gly Trp Met Leu Met Cys Thr Met Gly Arg
1               5                   10
```

α-SHEET POLYPEPTIDES AND THEIR USE

CROSS REFERENCE

This application claims priority to U.S. Provisional Application Ser. No. 63/224,815 filed Jul. 22, 2021, incorporated by reference herein in its entirety.

FEDERAL FUNDING STATEMENT

This invention was made with government support under Grant Nos. R01 GM095808 and R01 AG067476, awarded by the National Institutes of Health, and Grant No. W81XWH-19-1-0050, awarded by the US Army Medical Research Acquisition Activity. The government has certain rights in the invention.

SEQUENCE LISTING STATEMENT

A computer readable form of the Sequence Listing is filed with this application by electronic submission and is incorporated into this application by reference in its entirety. The Sequence Listing is contained in the file created on May 9, 2022 having the file name "21-0646-US-SeqList_ST25.txt" and is 20 kb in size.

BACKGROUND

Amyloid diseases affect over a billion people worldwide. One of the best known is Alzheimer's Disease (AD), a fatal neurodegenerative disorder clinically characterized by the progressive deterioration of memory and cognitive functions. AD is the sixth leading cause of death in the US and the leading cause of dementia worldwide, affecting more than 50 million people. The primary pathological indicators of AD are extracellular amyloid-D (AD) plaques and intraneuronal neurofibrillary tangles of the tau protein. The cascade of plaque deposition and tangle formation follows a pattern: starting in the entorhinal/perirhinal cortex, spreading through limbic structures and the hippocampus, and eventually reaching the frontal, temporal, and parietal cortex[4]. The process begins with the misfolding of the Aβ peptide, which is clipped from the amyloid precursor protein (APP) by α-, ⊕-, and γ-secretase enzymes. In its monomeric form, Aβ is associated with a variety of biological functions, but it can misfold into an aggregation competent state, leading to a heterogeneous distribution of low- to high-molecular-weight oligomers that eventually form the characteristic amyloid plaques. Importantly, disease progression is not correlated with amyloid plaque burden nor tau tangle formation, but rather with the presence of low molecular weight (LMW) soluble oligomers that act as the primary toxic agents. In fact, in the absence of fibrils, these LMW soluble oligomers induce toxicity and neuronal death, as demonstrated in mouse models of AD and familial cases of AD that do not produce plaques.

SUMMARY

In a first aspect, the disclosure provides α-sheet polypeptide multimers, comprising two or more monomeric α-sheet polypeptides that are covalently linked. In various embodiments, the multimer comprises a dimer, trimer, tetramer, pentamer, or hexamer, or wherein the multimer comprises a dimer. In various other embodiments, the two or more monomeric α-sheet polypeptides are covalently linked by 1 or more (1, 2, 3, or more):

(a) disulfide bonds;
(b) other covalent bonding between cysteine residues present in two monomers;
(c) thioether bridges between two monomers;
(d) covalent bonding between tyrosine residues present in two monomers;
(e) 1,2,3-triazole bridges between two monomers;
(f) amide bonds between two monomers;
(g) covalent bonding between histidine residues present in two monomers;
(h) conjugation to a core structure that covalently links multiple monomeric α-sheet polypeptides, including but not limited to poly-lysine, poly-ornithine, polyethylene glycol (PEG), Poly(amidoamine) (PAMAM), other polymers, and nanoparticle core structures;
(i) covalent bonding between norbrorene moieties present in two monomers;
(j) covalent bonding between a maleimide motif present in one monomer and the sulfur atom on a cysteine residue another monomer; and/or
(k) covalent linkage of two monomers by a linking moiety including but not limited to Bis(maleimido)ethane (BMOE); 1,1'-(2,2'-oxybis(ethane-2,1-dioyl))bis(1H-pyrrole-2,5-dione) (MalPEG1); and

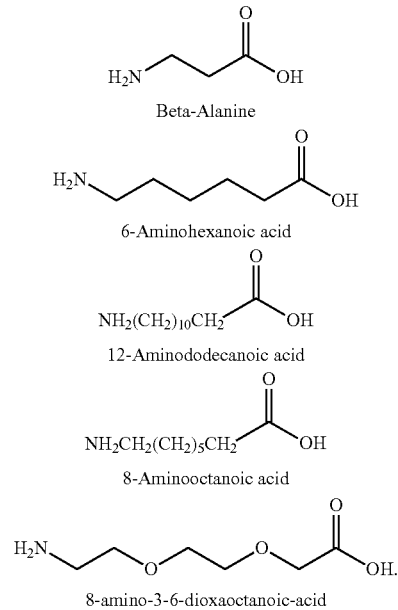

In other embodiments, each monomeric α-sheet polypeptide is at least 12-23 amino acids in length and comprises at least one cysteine residue.

In some embodiments, the two or more monomeric α-sheet polypeptides are covalently linked by conjugation to a core structure, including but not limited to poly-lysine, poly-ornithine, polyethylene glycol (PEG), Poly(amidoamine) (PAMAM), other polymers, and nanoparticle core structures.

In various embodiments, each monomeric α-sheet polypeptide comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence selected from SEQ ID NO:1-30 or its reverse chiral counterpart, as shown in Table 1, wherein:

(a) each monomeric α-sheet polypeptide includes at least one cysteine residue; and
(b) residues in lower-case are D amino acids, residues in upper case are L amino acids, and G residues are achiral.

In some embodiments, each monomeric α-sheet polypeptide is identical; in other embodiments, the multimer comprises monomeric α-sheet polypeptide that differ from each other. In various further embodiments, one or more monomeric α-sheet polypeptide comprises an additional functional domain.

In another aspect, the disclosure provides α-sheet polypeptides comprising an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence selected from SEQ ID NO:1-30 or its reverse chiral counterpart, as shown in Table 1, wherein residues in lower-case are D amino acids, residues in upper case are L amino acids, and G residues are achiral.

The disclosure also provides pharmaceutical compositions, comprising:
(a) the α-sheet polypeptide or multimer of any embodiment or combination of embodiments herein; and
(b) a pharmaceutically acceptable carrier.

The disclosure further provides compositions, comprising:
(a) a polymer coating on a surface; and
(b) α-sheet polypeptides covalently linked to the polymer coating.

In one embodiment, the polymer comprises a catecholamine polymer; optionally, wherein the polymer comprises polydopamine, poly-L-DOPA, polyepinephrine, polynoradrenaline, and any synthetic product which contains a di-hydroxyl phenol and a branched chain of any length that terminates with a primary amine, and combinations thereof. In various embodiments, the polymer coating may be between about 25 nm and about 250 nm in thickness, or between about 50 nm and about 200 nm in thickness, or between about 60 nm and about 150 nm in thickness, or between about 60 nm and about 100 nm in thickness, or between about 70 nm and about 90 nm in thickness, or between about 75 nm and 85 nm in thickness, or about 80 nm in thickness. In other embodiments, the surface may include but is not limited to assay plates (including but not limited to microwell plates), glass, ceramic, microfluidic channels and devices, membranes, plastic, polysaccharides, titanium, silicone, nylon, nitrocellulose, teflon beads, gauze, surgical thread, bandages, and medical devices. In various further embodiments, the α-sheet polypeptides may comprise multimers or polypeptides of any embodiment disclosed herein, one or more α-sheet polypeptides disclosed in U.S. Pat. No. 9,896,487, or comprise 12-23 contiguous amino acids according to the general formula X1-X2-X3-X4-X5, wherein X1 is 0-7 contiguous amino acid residues that do not alternate between L and D residues;
X2 is 5-9 contiguous amino acid residues alternating between D amino acids and L amino acids;
X3 is 0-5 contiguous amino acid residues that do not alternate between L and D residues;
X4 is 4-12 contiguous amino acid residues alternating between D amino acids and L amino acids; and
X5 is 0-4 contiguous amino acid residues that do not alternate between L and D residues.

In another aspect, the disclosure provides methods for treating or limiting development of an amyloid disease or amyloid-associated disease, comprising administering to a subject with an amyloid disease or amyloid-associated disease an amount effective of the α-sheet polypeptide multimer or the polypeptide of any embodiment disclosed herein, to treat or limit development of the disease.

In a further aspect, the disclosure provides methods for treating or limiting development of a disorder selected from the group consisting of Creutzfeldt-Jakob disease, spongiform encephalopathy, light chain amyloidosis, Huntington's disease, amyotrophic lateral sclerosis (ALS), senile systemic amyloidosis, familial amyloid polyneuropathy, Kennedy disease, Machado-Joseph disease, Alzheimer's disease, bovine spongiform encephalopathy, scrapie, type 2 diabetes, amyloidosis caused by transthyretin (ATTR), Parkinson's disease, Lewy body disease, traumatic brain injury, atherosclerosis, rheumatoid arthritis, aortic medial amyloid, prolactinomas, dialysis-related amyloidosis, cerebral amyloid angiopathy, Finnish amyloidosis, lattice corneal dystrophy, multiple myeloma, and diseases associated with amyloid-biofilm bacterial infections, wherein the method comprises administering to a subject in need thereof an amount effective of the α-sheet polypeptide multimer or the polypeptide of any embodiment disclosed herein, to treat or limit development of the disorder.

In one aspect, the disclosure provides methods for diagnosing, prognosing, or monitoring an amyloid disease or amyloid-associated disease, comprising
(a) contacting a tissue sample from a subject at risk of having an amyloid disease or amyloid-associated disease with the α-sheet polypeptide multimer or the polypeptide of any embodiment disclosed herein, under conditions suitable for binding of the α-sheet polypeptide multimer or polypeptide with an amyloid intermediate, if present in the tissue sample, to produce a binding complex
(b) detecting binding complexes in the tissue samples; and
(c) diagnosing or prognosing an amyloid disease or amyloid-associated disease based on the detecting.

In another aspect, the disclosure provides methods for diagnosing or prognosing an amyloid disease or amyloid-associated disease, comprising
(a) contacting a tissue sample from a subject at risk of having an amyloid disease or amyloid-associated disease with the composition of any embodiment disclosed herein, under conditions suitable for binding of the α-sheet polypeptide multimer or polypeptide with an amyloid intermediate, if present in the tissue sample, to produce a binding complex
(b) detecting binding complexes in the tissue sample; and
(c) diagnosing or prognosing an amyloid disease or amyloid-associated disease based on the detecting.

In one aspect, the disclosure provides medical devices comprising the α-sheet polypeptide multimer or the polypeptide of any embodiment disclosed herein, coated on a surface of the medical device. In some embodiments, the medical device comprises a polymer coating, including but not limited to a polydopamine (PDA) coating, on a surface of the device, and the α-sheet polypeptide multimer or the α-sheet polypeptide is covalently linked to the polymer coating. In other embodiments, the medical device may be selected from the group consisting of prosthetic heart valves, cardiac pacemakers, cerebrospinal fluid shunts, urinary catheters, intravascular catheters, ocular prostheses, prosthetic joints, orthopedic implants, titanium-containing implants, polystyrene-containing implants, surgical mesh implants, breast implants, dental implants, and intrauterine contraceptive devices.

Figure 13:
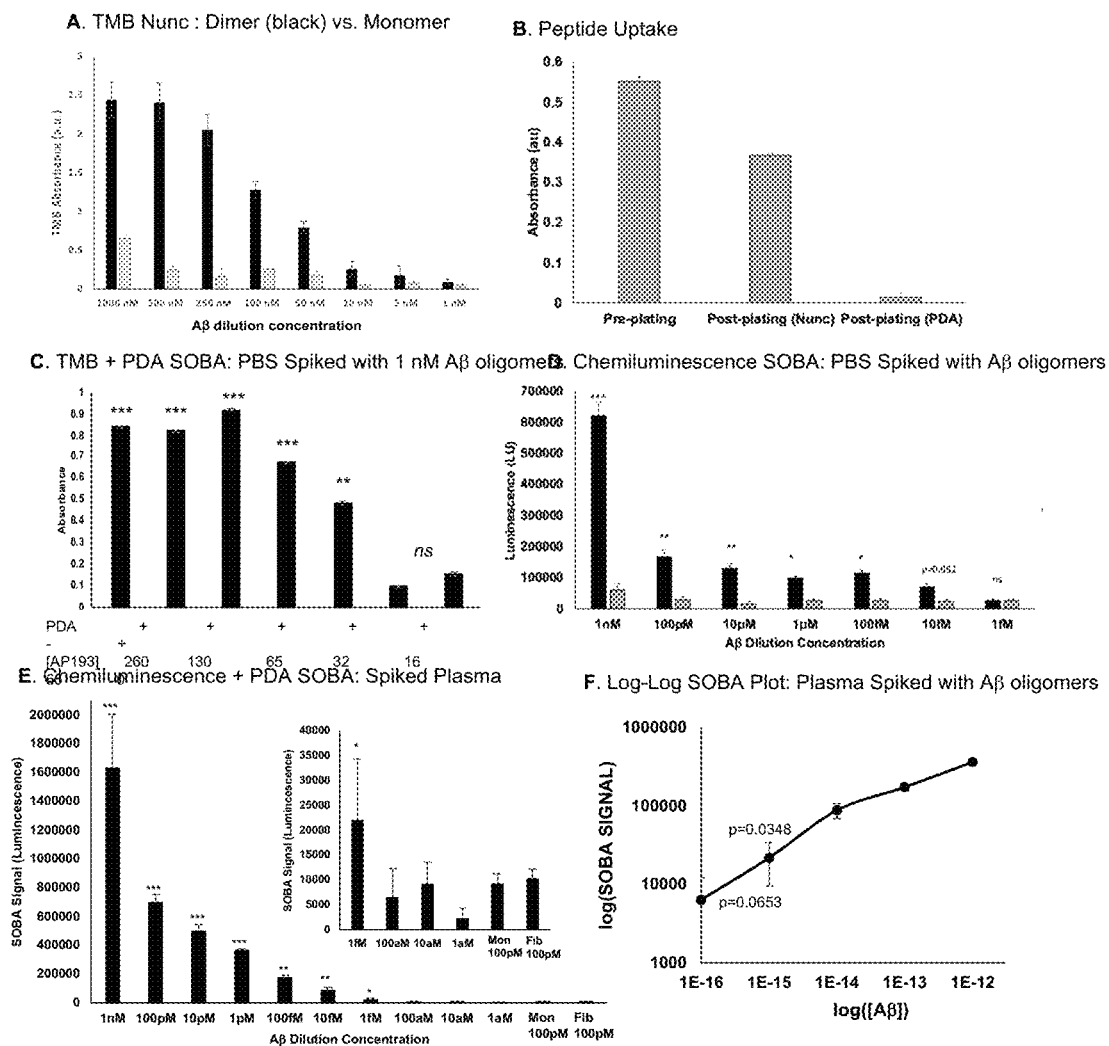

FIG. 13. Development of the SOBA assay and limit of detection (LOD). (A) Comparison of AP193 dimer (black) vs AP193 monomer (grey) using a Nunc plate and the TMB protocol. Pre-incubated, toxic Abeta42 was serially diluted and applied to the plate. The dimer provides more than a 2×effect on the SOBA signal and the monomer signal dies off faster at lower concentrations. Coupling of AP193 monomer to the PDA coating is also minimal compared with the dimer. (B) Absorbance at 280 nm reflects the extent of peptide not coupled to the surface. The PDA coating improved display of the AP193 dimer capture peptide for amplification of the signal relative to the Nunc plates. (C) PDA leads to increased signal at previously undetectable levels using the TMB protocol. Clear polystyrene plates were coated with PDA and serial dilutions of AP510 were applied starting from 260 uM and extending to 16 uM AP510. Then, pre-incubated, toxic Abeta42 was added at 1 nM to all wells, including a set of wells that did not have AP193 dimer coupled but was fully quenched to quantify background signal. We saw an increase in signal for all conditions relative to the 'original' protocol from panel (B), with maximum signal reached at 65 uM and plateauing for higher concentrations of AP193 dimer coupled to the plate. (D) LOD calibration with chemiluminescence protocol using a Nunc plate. Nunc amino linker plates were used to compare chemiluminescence directly to the colorimetric sensitivity quantified in panel (B). We saw significant detection down to 100 fM with this minor change, compared with 10 nM for the colorimetric assay. (E) LOD calibration with PDA-functionalized plate using chemiluminescence protocol for pooled human plasma spiked with pre-incubated Aβ42 toxic oligomers, Monomer (Mon 100 pM), or Protofibril (Fib 100 pM). Notice the large difference in the signal for 100 μM toxic oligomer versus the same concentration of monomeric and protofibrillar forms of Aβ42. The inset is a blow-up of the lower concentrations and other conformer samples. We used 65 μM AP510d coupled to a white polystyrene plate coated with PDA. Significance was observed at 1 fM. (F) Log-log plot of plasma SOBA results from panel e. The LOD is 1 fM and corresponds to a SOBA signal of 21,943, such that below that the results are not statistically significant and cannot be distinguished from blanks. All p-values are relative to the blanks for that sample. * p-value<0.05,  p-value<0.01,  p-value<0.001, *** p-value<0.0001.

Figure 14:
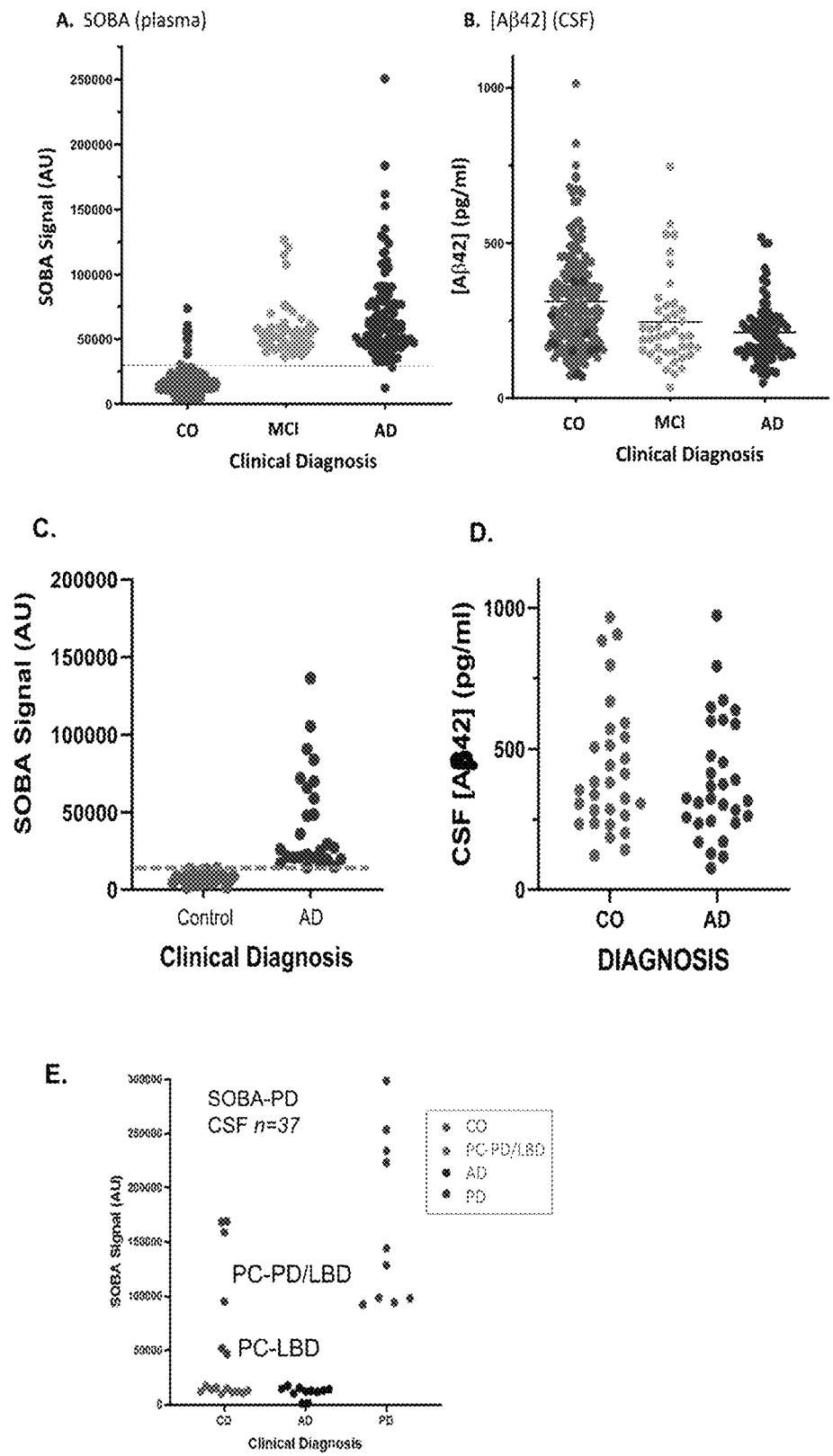

FIG. 14. SOBA results for detection of toxic oligomers associated with Alzheimer's disease and Parkinson's disease. (A) Raw luminescence values for SOBA detection of Abeta oligomers in human plasma samples using the original two antibody method with dimeric capture agent AP193 dimer and polymer coating of the wells to amplify the signal. (B) Corresponding CSF total Abeta42 concentration for the subjects in panel (A). (C) Raw luminescence values using from commercial control and AD plasma samples using the Next-Gen version of SOBA with dimeric capture peptides, including AP530d, PDA coating and single antibody detection. (D) Corresponding total Abeta42 concentration in CSF for the subjects in panel (C). (E) Detection of alpha-synuclein oligomers associated with PD and Lewy Body Dementia in CSF of patient samples.

Figure 15:
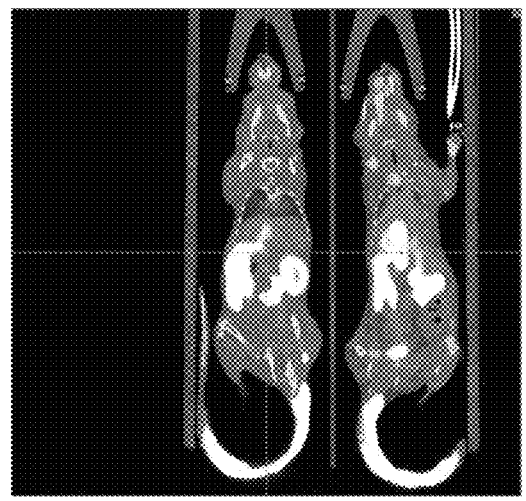

FIG. 15. PET imaging of WT (left) and transgenic AD mouse using $F^{18}$ labeled alpha-sheet peptide.

Figure 16:
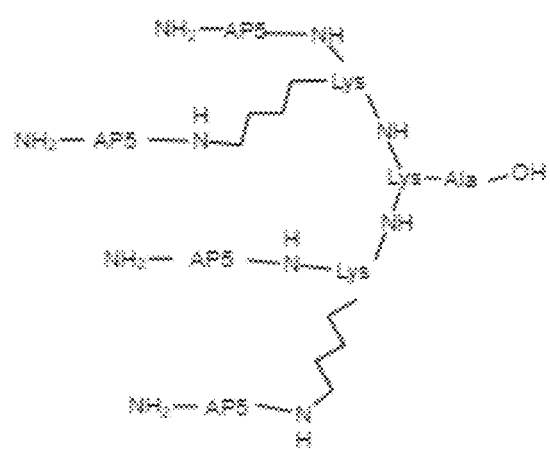

FIG. 16. The AP5 dendrimer uses a poly-lysine core to produce multiple branches onto which AP5 monomers are attached. The dendrimer can be synthesized by simultaneous deprotection of Fmoc protecting groups on the N-terminus and side chain of the lysine residues to expose two primary amines for coupling of the subsequent amino acid. We started with a tetra-valent construct.

Figure 17:
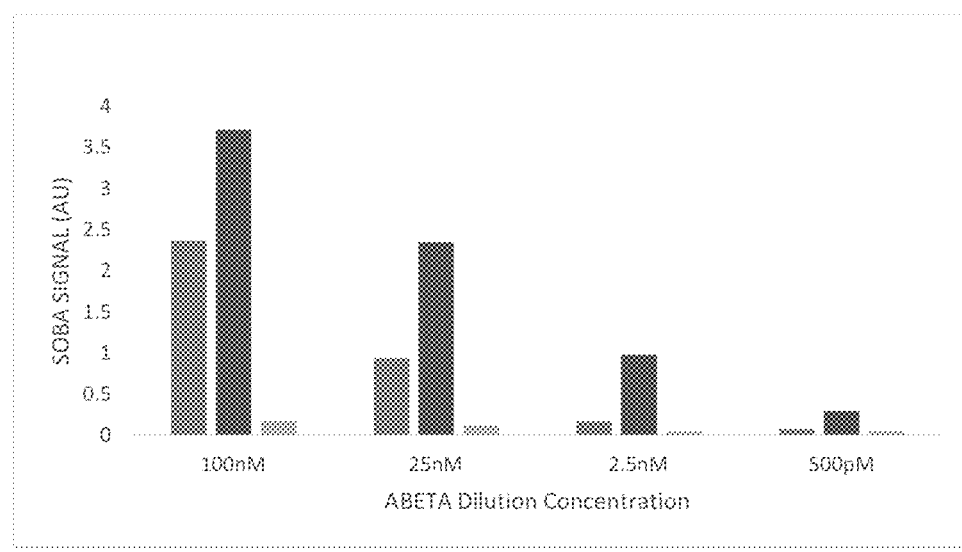

FIG. 17. Different concentrations of Abeta42 toxic oligomers were applied to Nunc SOBA plate. For each concentration of Abeta42, the grey bar on the left is the AP510 dimer, the AP5 dendrimer is the charcoal-colored bar in the middle and the bar on the right is the blank. The dendrimer provides a stronger signal, which, in particular, is very significant at the lowest concentrations, where the effect is >4-fold.

Figure 18:
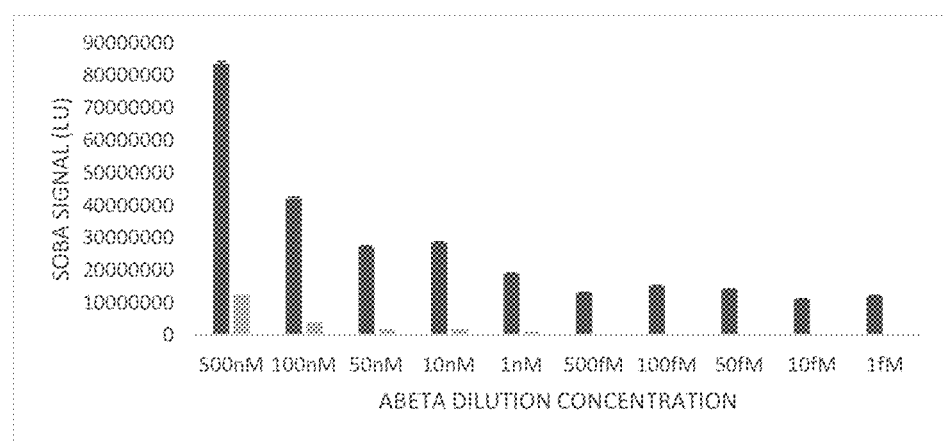

FIG. 18. Employing chemiluminescence and PDA with the dendrimer attached to the Nunc plate provides very high signals (black) versus the blank (grey).

DETAILED DESCRIPTION

All references cited are herein incorporated by reference in their entirety. Within this application, unless otherwise stated, the techniques utilized may be found in any of several well-known references such as: Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, CA), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, CA), Culture of Animal Cells: A Manual of Basic Technique, 2nd Ed. (R. I. Freshney. 1987. Liss, Inc. New York, NY), Gene Transfer and Expression Protocols, pp. 109-128, ed. E. J. Murray, The Humana Press Inc., Clifton, N.J.), and the Ambion 1998 Catalog (Ambion, Austin, TX).

As used herein, the singular forms "a", "an" and "the" include plural referents unless the context clearly dictates otherwise.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), valine (Val; V), and norleucine (Nle, B).

In the various polypeptide sequences disclosed herein, lower case letters denote D-amino acids, while upper case letters represent L amino acids, while "G" (glycine) is achiral.

All embodiments of any aspect of the invention can be used in combination, unless the context clearly dictates otherwise.

In a first aspect, the disclosure provides α-sheet polypeptide multimers, comprising two or more monomeric α-sheet polypeptides that are covalently linked.

The inventors have previously demonstrated that monomeric polypeptides that adopt an α-sheet structure, regardless of the primary amino acid sequence and thus can be used, for example, in therapeutic and diagnostic methods (see U.S. Pat. No. 9,896,487, incorporated by reference herein in its entirety). As demonstrated therein, the primary amino acid sequence of the polypeptides does not per se dictate the polypeptide activity. Instead it is the ability of the polypeptides to adopt a stable α-sheet structure that is operative, and that is achieved through the recited polypeptide generic structure and the recited arrangement of alternating D/L amino acids. As demonstrated therein, random primary sequences of amino acids are active in the polypeptides of the invention. These same primary sequences are not active if the polypeptide is composed entirely of L-amino acids or if the L/D amino acids are randomly distributed within the polypeptide such that they do not include alternating L/D positions.

The inventors herein disclose that multimers of two or more monomeric α-sheet polypeptides that are covalently linked have dramatic and surprising improvement in inhibitory potency relative to monomer α-sheet polypeptides.

As used herein, "α-sheet polypeptides" are polypeptides that comprise templated alternation of neighboring amino acids in their L- and D-forms in α-strands, producing the characteristic secondary structure capable of forming an α-sheet. An α-sheet resembles a β-sheet except that the carbonyl oxygens are aligned on one face of a strand and the NH groups on the other instead of alternating, which gives rise to different physical properties.

The multimer may comprise 2, 3, 4, 5, 6, 7, 8, 9, 10, or more monomeric α-sheet polypeptides that are covalently linked, as deemed appropriate for an intended use. As will be understood by those of skill in the art in light of the teachings herein, any suitable number of monomeric α-sheet polypeptides may be covalently linked to form the multimers of the disclosure. In a specific embodiment, the multimer comprises 2 α-sheet polypeptides that are covalently linked (i.e.: a dimer). In other embodiments, the multimer comprises 3 α-sheet polypeptides that are covalently linked (i.e., a trimer). In other embodiments, the multimer comprises 4 α-sheet polypeptides that are covalently linked (i.e., a tetramer). In other embodiments, the multimer comprises 5 α-sheet polypeptides that are covalently linked (i.e., a pentamer). In other embodiments, the multimer comprises 6 α-sheet polypeptides that are covalently linked (i.e., a hexamer).

The multimer may comprise any suitable covalent linkage between the two or more monomeric α-sheet polypeptides. In one embodiment, the two or more monomeric α-sheet polypeptides are provided in a fusion protein, as a protein insertion, or optionally separated by an amino acid linker of any suitable length and amino acid composition.

In one specific embodiment, the two or more monomeric α-sheet polypeptides are covalently linked by one or more disulfide bond. In one specific embodiment, two monomeric α-sheet polypeptides are covalently linked by at least one disulfide bond. In a further specific embodiment two monomeric α-sheet polypeptides are covalently linked by one disulfide bond.

In various other embodiments, the two or more monomeric α-sheet polypeptides may be covalently linked by one or more of the following:

A. Cysteine multimerization. Cys maleimide utilizes a malemide thiol reaction to coordinate two peptides and form a dimer or other multimer. One monomer contains the maleimide motif (no Cys residue in this monomer) and the other contains a Cysteine residue (no maleimide in this monomer). The double bonded side of the maleimide ring displaces the hydrogen on the thiol of the Cys residue and covalently bonds to the sulfur atom to form a dimer. Maleimide has been shown to operate as an amino acid side chain modification, but it can also operate entirely alone in the sequence as a pseudo amino acid or cap to the peptide. Similar to Cys, many units throughout the peptide could facilitate multimers rather than just dimers B. Thioether dimerization. One monomer unit A contains an alkyl halogenated (including but not limited to brominated) amino acid and no cysteine, while monomer B contains a single Cysteine amino acid, which readily reacts via alkylation of the thiol to form a thioether bridge coordinating the dimers. Any amino acid in monomer A can be alkyl halogenated (including but not limited to brominated).

C. Dityrosine multimerization. Utilizing the Miyaura-Suzuki reaction (or the less efficient peroxidase-catalyzed reaction), dityrosine bonds can be formed between two monomers that each contain a single tyrosine residue. The mechanism involves oxidation of tyrosine to produce a readily reactive side chain to form dityrosine dimers. The use of 2 or more Tyr residues per monomer facilitates multimers, while a single Tyr per monomer generates a dimer.

D. Dityrosine multimerization. Photo-induced dityrosine crosslinking achieved utilizing Ru(bpy)3 2+ reaction in response to UV exposure rapidly crosslinks tyrosine residues in each monomer to form dimers. The use of 2 or more Tyr residues per monomer facilitates multimers, while a single Tyr per monomer generates a dimer.

E. Click chemistry. Utilizing monomer A with an R1-alkyne group (conjugated to monomer A via amino acid modification or to the end of the monomer A sequence, where R1=monomer A) and one monomer B with an R2-azide group (conjugated to monomer B via amino acid modification or to the end of the monomer sequence, where R2=monomer B), and copper chelation, a dimer is readily formed with a 1,2,3-triazole bridge between the two or more monomer units for multimerization.

F. Amide bond linked multimers. Amide bond-linked monomers are produced by the incorporation of a lysine residue for C-terminal dimerization or glutamate residue for N-terminal dimerization. The first approach uses the alpha and epsilon amino groups of a lysine residue to produce amide bonds with the alpha amine groups of the first residue of the two-monomers. Fmoc-Lys(Fmoc)-OH can be used for this purpose by attaching it to the resin, and after alpha and epsilon-Fmoc group deprotection, the two monomer chains are simultaneously elongated. The second approach requires, before the cleavage from resin, the use of Fmoc-Glu-OH with its alpha and delta carboxylic group without the protection group, to link two or more elongated monomer chains. These can be expanded into multimers if the first addition to the two monomer chains is another Fmoc-Lys (Fmoc)-OH, as tree-branches spread out in this manner.

G. ROMP dimerization. Ring opening metathesis polymerization (ROMP), can polymerize monomers to form multimers of various sizes depending on reaction conditions. ROMP utilizes a ruthenium complex to initiate polymerization at a norbornene motif by minimizing energy through reducing ring strain in the norbornene ring. Norbornene added in the peptide sequence as a stand-in amino acid surrogate can allow for this rapid polymerization to form dimers as well as multimers of desired sizes.

H. Decafluorobiphenyl (DFBP) to link cysteine residues or histidine residues present on the each monomeric α-sheet polypeptide.

I. Multimers can be generated via conjugation of the two or more monomeric α-sheet polypeptides to a variety of core structures that serve to covalently link multiple monomeric α-sheet polypeptides to form dimers and higher order structures (i.e.: trimers and above). Non-limiting and exemplary such core structures include poly-lysine, poly-ornithine, polyethylene glycol (PEG), Poly(amidoamine) (PAMAM), any other polymers as appropriate, nanoparticles, etc. In this embodiment, multimers can be constructed with varying sizes (MW) and coordination numbers (number of conjugated peptides) using standard methods. These materials can be functionalized to react readily with primary amines and thiols in monomer sequences (Lys and C-term for amines, and Cys for thiols).

J Some other moieties that can be used to covalently link the two or more monomeric α-sheet polypeptides: Bis(maleimido)ethane (BMOE); 1,1'-(2,2'-oxybis(ethane-2,1-dioyl))bis(1H-pyrrole-2,5-dione) (MalPEG1); and

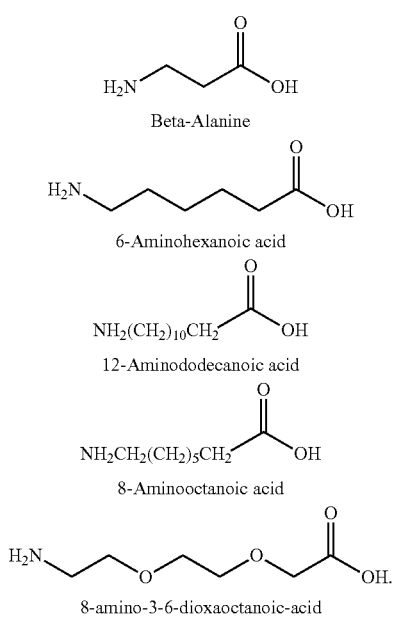

Beta-Alanine

6-Aminohexanoic acid

12-Aminododecanoic acid

8-Aminooctanoic acid 8-amino-3-6-dioxaoctanoic-acid

Thus, in various embodiments:

Each monomeric α-sheet polypeptide in the multimer comprises at least one cysteine residue, or each monomeric α-sheet polypeptide in the multimer comprises a single cysteine residue, and the monomeric α-sheet polypeptides are covalently linked via the cysteine residues. In one embodiment, each monomeric α-sheet polypeptide in the multimer comprises a single cysteine residue, and the multimer comprises a dimer.

Each monomeric α-sheet polypeptide in the multimer comprises at least one histidine residue, or each monomeric α-sheet polypeptide in the multimer comprises a single histidine residue, and the monomeric α-sheet polypeptides are covalently linked via the histidine residues. In one embodiment, each monomeric α-sheet polypeptide in the multimer comprises a single histidine residue, and the multimer comprises a dimer.

Each monomeric α-sheet polypeptide in the multimer comprises at least one tyrosine residue, or each monomeric α-sheet polypeptide in the multimer comprises a single tyrosine residue, and the monomeric α-sheet polypeptides are covalently linked via the tyrosine residues. In one embodiment, each monomeric α-sheet polypeptide in the multimer comprises a single tyrosine residue, and the multimer comprises a dimer.

Each monomeric α-sheet polypeptide in the multimer comprises at least one norbornene moiety as an amino acid surrogate, or each monomeric α-sheet polypeptide in the multimer comprises a single norbornene moiety as an amino acid surrogate, and the monomeric α-sheet polypeptides are covalently linked via the norbornene moieties. In one embodiment, each monomeric α-sheet polypeptide in the multimer comprises a single norbornene moiety residue, and the multimer comprises a dimer, trimer, tetramer, pentamer, hexamer, or higher order multimer. In one non-limiting embodiment, the multimers are formed by ROMP dimerization, which can polymerize monomers to form multimers of various sizes depending on reaction conditions. ROMP utilizes a ruthenium complex to initiate polymerization at a norbornene motif by minimizing energy through reducing ring strain in the norbornene ring. Norbornene added in the monomers as a stand-in amino acid surrogate can allow for this rapid polymerization to form dimers as well as multimers of desired sizes.

One monomeric α-sheet polypeptide in the multimer (monomer A) has no cysteine residues, and the other monomeric α-sheet polypeptide in the multimer (monomer B) comprises least one cysteine residue, or monomer B comprises a single cysteine residue, and monomer A and B are covalently linked via a covalent bond between any amino acid residue on monomer A and the sulfur atom on the cysteine residue in monomer B. In one embodiment, the multimer comprises a dimer. By way of non-limiting example, in one embodiment (monomer A) comprises a maleimide motif (on any residue in monomer A or as a stand-alone residue in the monomer A sequence) and no cysteines, and monomer B comprises least one cysteine residue, or monomer B comprises a single cysteine residue, and monomer A and B are covalently linked via a covalently bond between the maleimide motif on monomer A and the sulfur atom on the cysteine residue in monomer B. In one embodiment, the multimer comprises a dimer.

One monomeric α-sheet polypeptide in the multimer (monomer A) has no cysteine residues, and the other monomeric α-sheet polypeptide in the multimer (monomer B) comprises least one cysteine residue, or monomer B comprises a single cysteine residue, and monomer A and B are covalently linked via a thioether bridge between any amino acid residue on monomer A and the sulfur atom on the cysteine residue in monomer B. In one embodiment, the multimer comprises a dimer. By way of non-limiting example, in one embodiment A comprises an alkyl halogenated (including but not limited to brominated) amino acid (any AA in the monomer may be an alkyl halogenated (including but not limited to brominated)) and no cysteines, and monomer B comprises least one cysteine residue, or monomer B comprises a single cysteine residue, and monomer A and B are covalently linked via a thioether bridge between the previously an alkyl halogenated (including but not limited to brominated) residue on monomer A (alkyl halogen displaced by the new S-bond upon covalent binding of the monomers) and the sulfur atom on the cysteine residue in monomer B.

The two or more monomeric α-sheet polypeptide in the multimer are covalently linked via a 1,2,3-triazole bridge between the monomer units. In one embodiment, the multimer comprises a dimer. By way of non-limiting example, in one embodiment, one monomeric α-sheet polypeptide in the multimer (monomer A) comprises an alkyne group conjugated to any residue in monomer A or added to the end of monomer A, and the other monomeric α-sheet polypeptide in the multimer (monomer B) comprises an azide group conjugated to any residue in monomer B or added to the end of monomer B, and monomer A and B are covalently linked after copper chelation, via a 1,2,3-triazole bridge between the two monomer units.

The two or more monomeric α-sheet polypeptide in the multimer are covalently linked via an amide bind between the monomer units. In one embodiment, the multimer comprises a dimer. By way of non-limiting example, in various embodiments, (a) each monomeric α-sheet polypeptide comprises a lysine residue at the C-terminus for C-terminal multimerization (such as dimerization), or (b) each monomeric α-sheet polypeptide comprises a glutamate residue at the N-terminus for N-terminal multimerization (such as dimerization). The first approach uses the alpha and epsilon amino groups of a lysine residue to produce amide bonds with the alpha amine groups of the first residue of the two-monomers. Fmoc-Lys(Fmoc)-OH can be used for this purpose by attaching it to the resin, and after alpha and epsilon-Fmoc group deprotection, the two monomer chains are simultaneously elongated. The second approach requires, before the cleavage from resin, the use of Fmoc-Glu-OH with its alpha and delta carboxylic group without the protection group, to link elongated monomer chains.

The multimers comprise 2, 3, 4, 5, 6, 7, 8, 9, 10, or more monomeric α-sheet polypeptides covalently linked to a suitable core structure, which may include but is not limited to poly-lysine, poly-ornithine, polyethylene glycol (PEG), Poly(amidoamine) (PAMAM), any other polymers as appropriate, and nanoparticles.

The multimers comprise two or more monomeric α-sheet polypeptides covalently linked via one or more linker selected from: Bis(maleimido)ethane (BMOE); 1,1'-(2,2'-oxybis(ethane-2,1-dioyl))bis(1H-pyrrole-2,5-dione) (MalPEG1); and

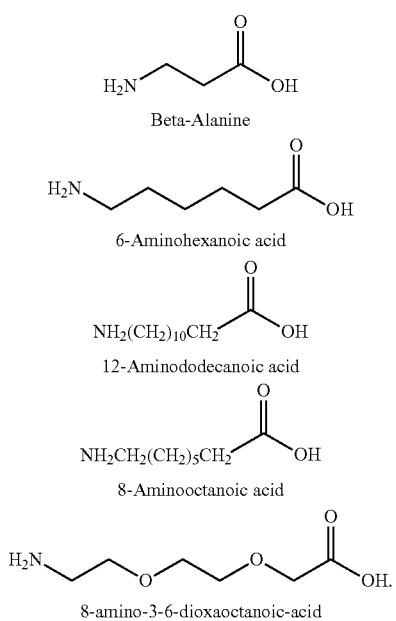

Beta-Alanine

6-Aminohexanoic acid

12-Aminododecanoic acid

8-Aminooctanoic acid 8-amino-3-6-dioxaoctanoic-acid

In one embodiment, each monomeric α-sheet polypeptide in the multimer is at least 12-23 amino acids in length, not including additional functional domains and other residues, such as additional residues that may be added for monomer linking purposes.

In one embodiment, each monomeric α-sheet polypeptide in the multimer comprises at least one cysteine residue in L or D form. In one embodiment, each monomeric α-sheet polypeptide in the multimer is at least 12-23 amino acids in length and comprises a single cysteine residue in L or D form.

In another embodiment, each monomeric α-sheet polypeptide in the multimer comprises at least one (1, 2, 3, or more) histidine residue in L or D form. In one embodiment, each monomeric α-sheet polypeptide in the multimer is at least 12-23 amino acids in length and comprises a single histidine residue in L or D form.

In one embodiment, each monomeric α-sheet polypeptide in the multimer comprises at least one (1, 2, 3, or more) tyrosine residue in L or D form. In one embodiment, each monomeric α-sheet polypeptide in the multimer is at least 12-23 amino acids in length and comprises a single tyrosine residue in L or D form.

In a further embodiment, each monomeric α-sheet polypeptide in the multimer comprises at least one (1, 2, 3, or more) norbornene moiety. In one embodiment, each monomeric α-sheet polypeptide in the multimer is at least 12-23 amino acids in length and comprises a single norbornene moiety.

In another embodiment, one monomeric α-sheet polypeptide (the B monomer) in a dimer comprises at least one (1, 2, 3, or more) cysteine residue in L or D form, and the other monomeric α-sheet polypeptide (the A monomer) does not include any cysteine residues. In one embodiment, each monomeric α-sheet polypeptide in the dimer is at least 12-23 amino acids in length and the A monomer comprises a single cysteine residue in L or D form.

In another embodiment, each monomeric α-sheet polypeptide comprises 12-23 contiguous amino acids according to the general formula X1-X2-X3-X4-X5, wherein
  X1 is 0-7 contiguous amino acid residues that do not alternate between L and D residues;
  X2 is 5-12 contiguous amino acid residues alternating between D amino acids and L amino acids;
  X3 is 0-7 contiguous amino acid residues that do not alternate between L and D residues;
  X4 is 4-12 contiguous amino acid residues alternating between D amino acids and L amino acids; and
  X5 is 0-4 contiguous amino acid residues that do not alternate between L and D residues.

As used herein, "alternating" means a stretch of at least 3 amino acids that alternative between L isomers and D isomers (i.e., L-D-L; D-L-D; etc.)

As used herein, "do not alternate between L and D residues" means that the region does not include a stretch of at least 3 amino acids that alternate between L isomers and D isomers. Such regions (X1, X3, and X5) may thus include both D and L residues. For example, the polypeptide RGNwNeSkMNEYSGWmLmCtMGR (AP500; SEQ ID NO: 1) (amino acid residues in uppercase are L amino acids, while amino acid residues in lowercase are D amino acids) has the following subunit structure as defined herein:
  X1 is 2 contiguous amino acid residues that do not alternate between L amino acids and D amino acids (RG);
  X2 is 7 contiguous amino acid residues alternating between D amino acids and L amino acids (NwNeSkM) (SEQ ID NO: 62);

X3 is 5 contiguous amino acid residues that do not alternate between L amino acids and D amino acids (NEYSG) (SEQ ID NO: 63);

X4 is 7 contiguous amino acid residues alternating between D amino acids and L amino acids (WmLmCtM) (SEQ ID NO: 64); and X5 is 2 amino acid residue that does not alternate between L amino acids and D amino acids (GR).

In another example, the polypeptide rGnWnEsKm-neyyGwMlMcTmGr (SEQ ID NO: 65)(AP506) has the following subunit structure as defined herein:

X1 is 0 contiguous amino acid residues that do not alternate between L amino acids and D amino acids;

X2 is 9 contiguous amino acid residues alternating between D amino acids and L amino acids (rGnWnEsKm) (SEQ ID NO: 66);

X3 is 3 contiguous amino acid residues that do not alternate between L amino acids and D amino acids (ney);

X4 is 11 contiguous amino acid residues alternating between D amino acids and L amino acids (yGwMlMcTmGr) (SEQ ID NO: 67); and X5 is 0 amino acid residue that does not alternate between L amino acids and D amino acids.

Those of skill in the art will recognize how other polypeptides sequences fit within the various general formulae described herein. The polypeptides described herein may be chemically synthesized using standard techniques.

The at least one (1, 2, 3, or more) cysteine, histidine, tyrosine, norbornene moiety, or other moieties to promote linking (including but not limited to those disclosed herein) (collectively referred to as "linking moiety") may be placed at any location in each monomeric α-sheet polypeptide. In a further embodiment, the at least one linking moiety in each monomeric α-sheet polypeptide is independently present in domain X1, X2, X3, or X4. In another embodiment, the at least one cysteine residue in each monomeric α-sheet polypeptide is independently present in domain X2, X3, or X4.

In one embodiment, for each monomeric α-sheet polypeptide, X1 is independently 0-2, 0 or 2 contiguous amino acid residues that do not alternate between L and D residues. In one embodiment, for each monomeric α-sheet polypeptide, all X1 amino acid residues (when present) are L amino acids. In another embodiment, for each monomeric α-sheet polypeptide, all X1 amino acid residues are D amino acids.

In one embodiment, for each monomeric α-sheet polypeptide, X2 is independently 6-10, 7-10, 7-9, 7, 8, 9, or 10 contiguous amino acid residues alternating between D amino acids and L amino acids.

In another embodiment, for each monomeric α-sheet polypeptide, X3 is independently 1-5, 2-5, 3-5, 3, 4, or 5 contiguous amino acid residues that do not alternate between L and D residues. In one embodiment, for each monomeric α-sheet polypeptide, all X3 amino acids are independently L amino acids or glycine. In another embodiment, for each monomeric α-sheet polypeptide, all X3 amino acids are independently D amino acids or glycine.

In one embodiment, for each monomeric α-sheet polypeptide, X4 is independently 6-12, 7-11, 7, 8, 9, 10, or 11 contiguous amino acid residues alternating between D amino acids and L amino acids.

In another embodiment, for each monomeric α-sheet polypeptide, X5 is independently 0-3, 0-2, 0, or 2 contiguous amino acid residues that do not alternate between L and D residues. In one embodiment, for each monomeric α-sheet polypeptide, all X5 amino acids (when present) are independently L amino acids.

In one embodiment, for one or more monomeric α-sheet polypeptide in the multimer:
X1 is 0-2 contiguous amino acid residues that do not alternate between L and D residues;
X2 is 7-10 or 7-8 contiguous amino acid residues alternating between D amino acids and L amino acids;
X3 is 3-5 or 4-5 contiguous amino acid residues that do not alternate between L and D residues;
X4 is 7-11 contiguous amino acid residues alternating between D amino acids and L amino acids; and
X5 is 0-2 contiguous amino acid residues that do not alternate between L and D residues. In one embodiment, all polypeptides in the multimer comprise this general formula.

In one specific embodiment, for one or more monomeric α-sheet polypeptide in the multimer:
X1 is 2 contiguous amino acid residues that do not alternate between L and D residues;
X2 is 7 contiguous amino acid residues alternating between D amino acids and L amino acids;
X3 is 5 contiguous amino acid residues that do not alternate between L and D residues;
X4 is 7 contiguous amino acid residues alternating between D amino acids and L amino acids; and
X5 is 2 contiguous amino acid residues that do not alternate between L and D residues.

In one embodiment, all polypeptides in the multimer comprise this general formula.

In another specific embodiment, for one or more monomeric α-sheet polypeptide in the multimer:
X1 is 2 contiguous amino acid residues that do not alternate between L and D residues;
X2 is 8 contiguous amino acid residues alternating between D amino acids and L amino acids;
X3 is 4 contiguous amino acid residues that do not alternate between L and D residues;
X4 is 7 contiguous amino acid residues alternating between D amino acids and L amino acids; and
X5 is 2 contiguous amino acid residues that do not alternate between L and D residues. In one embodiment, all polypeptides in the multimer comprise this general formula.

In a further specific embodiment, for one or more monomeric α-sheet polypeptide in the multimer:
X1 is 0 contiguous amino acid residues that do not alternate between L and D residues;
X2 is 9 contiguous amino acid residues alternating between D amino acids and L amino acids;
X3 is 3 contiguous amino acid residues that do not alternate between L and D residues;
X4 is 11 contiguous amino acid residues alternating between D amino acids and L amino acids; and
X5 is 0 contiguous amino acid residues that do not alternate between L and D residues. In one embodiment, all polypeptides in the multimer comprise this general formula.

In another specific embodiment, for one or more monomeric α-sheet polypeptide in the multimer:
X1 is 0 contiguous amino acid residues that do not alternate between L and D residues;
X2 is 10 contiguous amino acid residues alternating between D amino acids and L amino acids;
X3 is 4 contiguous amino acid residues that do not alternate between L and D residues;

X4 is 7 contiguous amino acid residues alternating between D amino acids and L amino acids; and X5 is 2 contiguous amino acid residues that do not alternate between L and D residues. In one embodiment, all polypeptides in the multimer comprise this general formula.

In one embodiment, X1 and X5 are the same length in a given monomeric α-sheet polypeptide (i.e.: the same length in at least one of the monomeric α-sheet polypeptides in the multimer). In another embodiment, X1 and X5 are the same length in each monomeric α-sheet polypeptide.

In another embodiment, X2 and X4 are the same length in a given monomeric α-sheet polypeptide, or in each monomeric α-sheet polypeptide.

In a further embodiment, each monomeric α-sheet polypeptide is at least 14-23, 17-23, 21-23, or 23 amino acids in length.

In one embodiment, each monomeric α-sheet polypeptide comprises an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence selected from SEQ ID NO:1-30, or its reverse chiral counterpart, as shown in Table 1 wherein:

(a) each monomeric α-sheet polypeptide includes at least one cysteine residue; and (b) residues in lower-case are D amino acids, residues in upper case are L amino acids, and G residues are achiral (always depicted in the upper case 'G').

TABLE 1

| | | | |
|---|---|---|---|
| AP500 | 2823.25 g/mol | 5646.50 g/mol | RGNwNeSkMNEYSGWmLmCtMGR (SEQ ID NO: 1) |
| AP501 | 2899.34 g/mol | 5798.68 g/mol | RGNwNeSkMNEYYGWmLmCtMGR (SEQ ID NO: 2) |
| AP502 | 2899.34 g/mol | 5798.68 g/mol | RGNwNeSkMneyyGWmLmCtMGR (SEQ ID NO: 3) |
| AP503 | 2899.34 g/mol | 5798.68 g/mol | RGNwNeSkMNEYYGWmLmTcMGR (SEQ ID NO: 4) |
| AP504 | 2826.29 g/mol | 5652.58 g/mol | RGNcNe SkMNEYYGWmLmLtMGR (SEQ ID NO: 5) |
| AP505 | 2898.40 g/mol | 5796.80 g/mol | RGNwCeSkMNEYYGWmLmLtMGR (SEQ ID NO: 6) |
| AP506 | 2899.34 g/mol | 5798.68 g/mol | rGnWnEsKmneyyGwMlMcTmGr (SEQ ID NO: 7) |
| AP510 (AP193) | 3009.46 g/mol | 6018.92 g/mol | RGEmNyFwMNEYYGWtMnCkMGR (SEQ ID NO: 8) |
| AP516 | 3009.46 g/mol | 6018.92 g/mol | rGeMnYfWmneyyGwTmNcKmGr (SEQ ID NO: 9) |
| AP520 | 2823.25 g/mol | 5646.50 g/mol | RGEmNlSwMNEYSGWtMnCkMGR (SEQ ID NO: 10) |
| AP521 | 2823.25 g/mol | 5646.50 g/mol | RGEcNlSwMNEYSGWtMnMkMGR (SEQ ID NO: 11) |
| AP522 | 2899.35 g/mol | 5798.70 g/mol | RGEcNlSwMNEYYGWtMnMkMGR (SEQ ID NO: 12) |
| AP523 | 2899.35 g/mol | 5798.70 g/mol | RGEcNlSwMneyyGWtMnMkMGR (SEQ ID NO: 13) |
| AP524 | 2973.49 g/mol | 5946.98 g/mol | RCEmNlSwMneyyGWtMnMkMGR (SEQ ID NO: 14) |
| AP525 | 2899.35 g/mol | 5798.70 g/mol | RGEmNlSwMneyyGWtMnMkCGR (SEQ ID NO: 15) |
| AP530 | 3009.46 g/mol | 6018.92 g/mol | RGEcNyFwMNEYYGWtMnMrMGK (SEQ ID NO: 16) |
| AP531 | 2991.42 g/mol | 5982.84 g/mol | RGEcNyFwMNEYYGWtMnMrBGK (SEQ ID NO: 17) |
| AP532 | 3008.51 g/mol | 6017.02 g/mol | RGEmCyFwMNEYYGWtMnMrBGK (SEQ ID NO: 18) |
| AP533 | 2991.42 g/mol | 5982.84 g/mol | RGExNyFwMNEYYGWtMnMrCGK (SEQ ID NO: 19); x is norleucine |
| AP534 | 2991.42 g/mol | 5982.84 g/mol | RGExNyFwMNEYYGWtMnMcRGK (SEQ ID NO: 20); x is norleucine |
| AP535 | 3009.46 g/mol | 6018.92 g/mol | RGEyNcFwMNEYYGWtMnMrMGK (SEQ ID NO: 21) |

TABLE 1-continued

| | | | | |
|---|---|---|---|---|
| AP536 | 2991.42 g/mol | 5982.84 g/mol | | RGElNyFwMNEYYGWtCnMrMGK (SEQ ID NO: 22) |
| AP537 | 2959.44 g/mol | 5918.88 g/mol | | RGElNyFwMNECYGWtMnMrMGK (SEQ ID NO: 23) |
| AP526 | 2823.25 g/mol | 5646.50 g/mol | rGeMnLsWmneysGwTmNcKmGr | Flipped APF520 (SEQ ID NO: 24) |
| AP527 | 2899.35 g/mol | 5798.70 g/mol | rGeMnLsWmneyyGwTmNmKcGr | Full Flip AP525 (SEQ ID NO: 25) |
| AP550 | 2949.34 g/mol | 5898.68 g/mol | RGEmNyFwMNEYYGWtMnCkAGR | SEQ ID NO: 26 |
| AP560 | 2889.22 g/mol | 2778.44 g/mol | RGEmNyFwMNEYYGWtAnCkAGR | SEQ ID NO: 27 |
| AP570 | 2949.34 g/mol | 5898.68 g/mol | RGEmNyFwMNEYYGWtAnCkMGR | SEQ ID NO: 28 |
| AP580 | 2959.35 g/mol | 5918.70 g/mol | RGEmNyFwMNEYYGWtLnCkVGR | SEQ ID NO: 29 |
| AP590 | 2959.35 g/mol | 5918.70 g/mol | RGEmNyFwMNEYYGWtVnCkLGR- | SEQ ID NO: 30 |

The multimer comprises two or more monomeric α-sheet polypeptides, where each monomer may comprise the identical amino acid sequence or may comprise different amino acid sequences. In one embodiment, all monomers in the multimer have the same amino acid sequence. In other embodiments, the monomers in a given multimer may include monomers having different amino acid sequences.

The monomeric α-sheet polypeptides or multimers may comprise additional residues at their N- and or C-termini. In a non-limiting embodiment the additional residues may comprise an additional functional domain. In some embodiments, one or more additional residue or moiety is added to facilitate covalent linking of the monomers; non-limiting such "linking moieties" are described above. In other non-limiting embodiments, an added functional domain may comprise a therapeutic moiety, a diagnostic moiety, a detectable moiety, a moiety to target the multimer to a specific in vivo location.

The monomers may comprise any amino acids, including non-natural amino acids or otherwise functionalized canonical amino acids with modalities used for multimerization, including but not limited to norleucine, maleimide, norbornene, and others described herein.

In another embodiment, the polypeptides or multimers are conjugated to a polymer, including but not limited to polydopamine (PDA), as described in more detail below.

In a second aspect, the disclosure provides α-sheet polypeptides comprising an amino acid sequence at least 50%, 55%, 60%, 65%, 70%, 75%, 80%, 85%, 90%, 91%, 92%, 93%, 94%, 95%, 96%, 97%, 98%, 99%, or 100% identical to the amino acid sequence selected from SEQ ID NO:1-30 or its reverse chiral counterpart, wherein residues in lowercase are D amino acids, residues in upper case are L amino acids, and G residues are achiral.

The polypeptides of this second aspect of the disclosure can be used, for example, to prepare the multimers of the first aspect, for uses of the multimers as described herein, as well as for other therapeutic and diagnostic uses disclosed herein.

All embodiments described for monomers in the first aspect of the disclosure can be used with the monomers of this second aspect. Thus, for example, the monomers may comprise any embodiment of one or more (1, 2, 3, or more) linking moieties as described in the first aspect.

In some embodiments of the first and second aspects, any amino acid substitutions relative to an L or D amino acid in the reference polypeptide amino acid sequence maintain chirality (i.e.: L amino acid substituted with L amino acid; D amino acid substituted with D amino acid).

In all embodiments of the first and second aspect of the disclosure, the α-sheet polypeptides may be capped or uncapped, as most appropriate for any given use. In various embodiments, one or both of the N-terminus or the C-terminus of the polypeptide is acetylated or amidated. In other embodiments, neither the N-terminus nor the C-terminus is capped.

In one embodiment, the polypeptides or multimers disclosed herein may be linked to other compounds to promote an increased half-life in vivo, such as by PEGylation, HESylation, PASylation, or glycosylation. Such linkage can be covalent or non-covalent.

In another embodiment, the disclosure provides pharmaceutical composition, comprising:
(a) the α-sheet polypeptide or multimer of any embodiment or combination of embodiments of the first and second aspects of the disclosure; and
(b) a pharmaceutically acceptable carrier.

The pharmaceutical compositions of the invention can be used, for example, in the methods disclosed herein. The pharmaceutical composition may comprise in addition to the peptide(s) (a) a lyoprotectant; (b) a surfactant; (c) a bulking agent; (d) a tonicity adjusting agent; (e) a stabilizer; (f) a preservative and/or (g) a buffer. In some embodiments, the buffer in the pharmaceutical composition is a Tris buffer, a histidine buffer, a phosphate buffer, a citrate buffer or an acetate buffer. The pharmaceutical composition may also include a lyoprotectant, e.g. sucrose, sorbitol or trehalose. In certain embodiments, the pharmaceutical composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the pharmaceutical composition includes a bulking agent, like glycine. In yet other embodiments, the pharmaceutical composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The pharmaceutical composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The pharmaceutical compositions described herein are substantially free of non-pharmaceutically acceptable components, i.e., contain amounts of non-pharmaceutically acceptable components lower than permitted by US regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.)

The composition may be formulated for any type of delivery, including but not limited to oral, parenteral, intravenous, sub-cutaneous, pulmonary, and nasal delivery.

The α-sheet polypeptide or multimer may be the sole active agent administered in the pharmaceutical composition, or the composition may comprise one or more other active agents suitable for an intended use. In various non-limiting embodiments, the composition may further comprise a peptidase inhibitor.

In a third aspect, the disclosure provides compositions, comprising:
  (a) a polymer coating on a surface; and
  (b) α-sheet polypeptides covalently linked to the polymer coating.

As disclosed in the examples herein, α-sheet polypeptides bind covalently to polymer-coated surfaces, exemplified by polydopamine (PDA) coated surfaces. Non-limiting, exemplary techniques for generating the compositions of the disclosure are provided in the examples, and thus the disclosure further provides methods for preparing the compositions of this third aspect comprising the steps as disclosed herein.

The inventors have demonstrated that the compositions of the disclosure can be used, for example, for very high sensitivity detection of α-sheet-containing toxic protein species in a biological sample obtained from a subject. The α-sheet polypeptides covalently linked to the polymer coating are used as a capture agent for the α-sheet-containing toxic protein species in the biological sample.

The polymer may be any self-assembling polymer, including but not limited to catecholamines. In some embodiments, the polymer may comprise polydopamine, poly-L-DOPA, polyepinephrine, polynoradrenaline, or any synthetic product that contains a di-hydroxyl phenol and a branched chain of any length that terminates with a primary amine (constituting a catecholamine), and combinations thereof. In one non-limiting embodiment, the polymer coating comprises polydopamine (PDA), The polymer coating may be of any thickness as suitable for an intended purpose. In non-limiting embodiments, the polymer coating is between about 25 nm and about 250 nm in thickness, or between about 50 nm and about 200 nm in thickness, or between about 60 nm and about 150 nm in thickness, or between about 60 nm and about 100 nm in thickness, or between about 70 nm and about 90 nm in thickness, or between about 75 nm and 85 nm in thickness, or about 80 nm in thickness. As used herein, "about" means+/−5% of the recited parameter.

The polymer coating may be over the entire surface, or a portion of the surface. The surface may be any surface suitable for an intended use, including but not limited to assay plates (including but not limited to microwell plates), glass, ceramic, microfluidic channels and devices, membranes, plastic, polysaccharides, titanium, silicone, nylon, nitrocellulose, teflon beads, gauze, surgical thread, bandages, medical devices, etc. The surface may be of any size and shape suitable for an intended use.

Any suitable α-sheet polypeptide can be used in the compositions of the disclosure. In one embodiment, the α-sheet polypeptide may comprise one or more α-sheet polypeptides disclosed in U.S. Pat. No. 9,896,487, incorporated by reference herein in its entirety. In one such embodiment, the α-sheet polypeptides comprise 12-23 contiguous amino acids according to the general formula X1-X2-X3-X4-X5, wherein
  X1 is 0-7 contiguous amino acid residues that do not alternate between L and D residues;
  X2 is 5-9 contiguous amino acid residues alternating between D amino acids and L amino acids;
  X3 is 0-5 contiguous amino acid residues that do not alternate between L and D residues;
  X4 is 4-12 contiguous amino acid residues alternating between D amino acids and L amino acids; and
  X5 is 0-4 contiguous amino acid residues that do not alternate between L and D residues.

In another embodiment, the α-sheet polypeptides comprise an α-sheet polypeptide or α-sheet polypeptide or multimer according to any embodiment or combination of embodiments of the first and second aspects of the disclosure.

In a fourth aspect, the disclosure provides medical device comprising the α-sheet polypeptide multimer or the α-sheet polypeptide of any embodiment or combination of embodiments disclosed herein, coated on a surface of the medical device. In one embodiment, the medical device comprises polydopamine (PDA) coating on a surface of the device, and the α-sheet polypeptide multimer or the α-sheet polypeptide is covalently linked to the PDA coating.

The medical devices can be used, for example, for placement in subjects in need thereof to reduce the risk of bacterial infection/biofilm formation on the medical device. Any suitable medical device can be used, including but not limited to prosthetic heart valves, cardiac pacemakers, cerebrospinal fluid shunts, urinary catheters, intravascular catheters, ocular prostheses, prosthetic joints, orthopedic implants, titanium-containing implants, polystyrene-containing implants, surgical mesh implants, breast implants, dental implants, and intrauterine contraceptive devices.

In a fifth aspect, the disclosure provides methods for treating or limiting development of an amyloid disease or amyloid-associated disease, comprising administering to a subject with an amyloid disease or amyloid-associated disease an amount effective of the α-sheet polypeptide multimer or the α-sheet polypeptide of any embodiment or combination of embodiments disclosed herein, to treat or limit development of the disease.

In one embodiment, the amyloid disease or amyloid-associated disease is selected from, but not limited to, the group consisting of Creutzfeldt-Jakob disease, spongiform encephalopathy, light chain amyloidosis, Huntington's disease, amyotrophic lateral sclerosis (ALS), senile systemic amyloidosis, familial amyloid polyneuropathy, Kennedy disease, Machado-Joseph disease, Alzheimer's disease, bovine spongiform encephalopathy, scrapie, type 2 diabetes, amyloidosis caused by transthyretin (ATTR), Parkinson's disease, Lewy body disease, traumatic brain injury, atherosclerosis, rheumatoid arthritis, aortic medial amyloid, prolactinomas, dialysis-related amyloidosis, cerebral amyloid angiopathy, Finnish amyloidosis, lattice corneal dystrophy, multiple myeloma, and diseases associated with amyloid-biofilm bacterial infections.

In another embodiment, the disclosure provides methods for treating or limiting development of a disorder selected from the group including but not limited to Creutzfeldt-Jakob disease, spongiform encephalopathy, light chain amyloidosis, Huntington's disease, amyotrophic lateral sclerosis (ALS), senile systemic amyloidosis, familial amyloid polyneuropathy, Kennedy disease, Machado-Joseph disease, Alzheimer's disease, bovine spongiform encephalopathy, scrapie, type 2 diabetes, amyloidosis caused by transthyretin (ATTR), Parkinson's disease, Lewy body disease, traumatic brain injury, atherosclerosis, rheumatoid arthritis, aortic medial amyloid, prolactinomas, dialysis-related amyloidosis, cerebral amyloid angiopathy, Finnish amyloidosis, lattice corneal dystrophy, multiple myeloma, and diseases associated with amyloid-biofilm bacterial infections, wherein the method comprises administering to a subject in need thereof an amount effective of the α-sheet polypeptide multimer or the α-sheet polypeptide of any embodiment or combination of embodiments disclosed herein, to treat or limit development of the disorder.

As used herein, "treating an amyloid disease/amyloid-associated disease" means accomplishing one or more of the following: (a) reducing the severity of the disease; (b) limiting or preventing development of symptoms characteristic of the disease(s) being treated; (c) inhibiting worsening of symptoms characteristic of the disease(s) being treated; (d) limiting or preventing recurrence of the disease(s) in patients that have previously had the disorder(s); (e) limiting or preventing recurrence of symptoms in patients that were previously symptomatic for the disease(s); and (f) limiting development of the disease in a subject at risk of developing the disease, or not yet showing the clinical effects of the disease.

As used herein, an "amount effective" refers to an amount of the polypeptide or multimer that is effective for treating and/or limiting amyloid disease or amyloid-associated disease. The polypeptides or multimers are typically formulated as a pharmaceutical composition, such as those disclosed above, and can be administered via any suitable route, including orally, parentally, by inhalation spray, nasally, rectally, or topically in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques or intraperitoneally. In one embodiment, administration is nasally.

Dosage regimens can be adjusted to provide the optimum desired response (e.g., a therapeutic or prophylactic response). A suitable dosage range may, for instance, be 0.1 fg/kg-100 mg/kg body weight; alternatively, it may be 0.5 fg/kg to 50 mg/kg; 1 fg/kg to 25 mg/kg, or 5 fg/kg to 10 mg/kg body weight. The polypeptides or multimers can be delivered in a single bolus, or may be administered more than once (e.g., 2, 3, 4, 5, or more times) as determined by an attending physician.

In a sixth aspect, the disclosure provides methods for diagnosing, prognosing, or monitoring an amyloid disease or amyloid-associated disease, comprising
   (a) contacting a tissue sample from a subject at risk of having an amyloid disease or amyloid-associated disease with the α-sheet polypeptide multimer or the α-sheet polypeptide of any embodiment or combination of embodiments disclosed herein, under conditions suitable for binding of the α-sheet polypeptide multimer or polypeptide with an amyloid intermediate, if present in the tissue sample, to produce a binding complex;
   (b) detecting binding complexes in the tissue sample; and
   (c) diagnosing, prognosing, or monitoring an amyloid disease or amyloid-associated disease based on the detecting.

The methods of this aspect can be used to more accurately diagnose, prognose, or monitor a course of treatment for patients that may be suffering from an amyloid disease or amyloid-associated disease and to thus provide more informed determination of treatment options by an attending caregiver. Individuals at risk of an amyloid disease or amyloid-associated disease are those exhibiting one or more signs, symptoms, or risk factors for an amyloid disease or amyloid-associated disease, including but not limited to Creutzfeldt-Jakob disease, spongiform encephalopathy, light chain amyloidosis, Huntington's disease, amyotrophic lateral sclerosis (ALS), senile systemic amyloidosis, familial amyloid polyneuropathy, Kennedy disease, Machado-Joseph disease, Alzheimer's disease, bovine spongiform encephalopathy, scrapie, type 2 diabetes, amyloidosis caused by transthyretin (ATTR), Parkinson's disease, Lewy body disease, traumatic brain injury, atherosclerosis, rheumatoid arthritis, aortic medial amyloid, prolactinomas, dialysis-related amyloidosis, cerebral amyloid angiopathy, Finnish amyloidosis, lattice corneal dystrophy, multiple myeloma, and diseases associated with amyloid-biofilm bacterial infections.

The tissue sample may be any suitable tissue sample including, but not limited to blood, serum, cerebral spinal fluid, nasal secretions, urine or other biological material from a subject at risk of an amyloid disease or amyloid-associated disease.

Conditions suitable for binding the polypeptides or multimers with an amyloid intermediate, if present in the tissue sample, to produce a binding complex will depend on specifics of the polypeptide(s) being used, the tissue sample, and the technique employed. Determining such suitable conditions are within the level of skill in the art based on the teachings herein.

The formation of such complexes, if any, indicating the presence of amyloid intermediates in the sample, is then detected and measured by suitable means. Such methods include, but are not limited to homogeneous and heterogeneous binding immunoassays, such as radioimmunoassays (RIA), ELISA, immunofluorescence, immunohistochemistry, FACS, BIACORE and Western blot analyses. In one specific embodiment, the methods comprise use of the SOBA assay as detailed herein.

The polypeptides and multimers for use in this aspect may comprise a conjugate as disclosed above, to provide a tag useful for any detection technique suitable for a given assay. The tag used will depend on the specific detection/analysis/diagnosis techniques and/or methods used. The methods may be carried in solution, or the polypeptide(s) of the invention may be bound or attached to a carrier or substrate, e.g., SOBA plates as described herein, microtiter plates (ex: for ELISA), membranes and beads, etc. Carriers or substrates may be made of glass, plastic (e.g., polystyrene), polysaccharides, nylon, nitrocellulose, or teflon, etc. The surface of such supports may be solid or porous and of any convenient shape.

In a seventh aspect, the disclosure provides method for diagnosing, prognosing, or monitoring an amyloid disease or amyloid-associated disease, comprising
  (a) contacting a tissue sample from a subject at risk of having an amyloid disease or amyloid-associated disease with a composition of the third aspect of the disclosure, under conditions suitable for binding of the α-sheet polypeptide multimer or polypeptide with an amyloid intermediate, if present in the tissue sample, to produce a binding complex
  (b) detecting binding complexes in the tissue sample; and
  (c) diagnosing, prognosing, or monitoring an amyloid disease or amyloid-associated disease based on the detecting.

The methods of this aspect can be used to more accurately diagnose, prognose, or monitor a course of treatment for patients that may be suffering from an amyloid disease or amyloid-associated disease and to thus provide more informed determination of treatment options by an attending caregiver. Individuals at risk of an amyloid disease or amyloid-associated disease are those exhibiting one or more signs, symptoms, or risk factors for an amyloid disease or amyloid-associated disease, including but not limited to Creutzfeldt-Jakob disease, spongiform encephalopathy, light chain amyloidosis, Huntington's disease, amyotrophic lateral sclerosis (ALS), senile systemic amyloidosis, familial amyloid polyneuropathy, Kennedy disease, Machado-Joseph disease, Alzheimer's disease, bovine spongiform encephalopathy, scrapie, type 2 diabetes, amyloidosis caused by transthyretin (ATTR), Parkinson's disease, Lewy body disease, traumatic brain injury, atherosclerosis, rheumatoid arthritis, aortic medial amyloid, prolactinomas, dialysis-related amyloidosis, cerebral amyloid angiopathy, Finnish amyloidosis, lattice corneal dystrophy, multiple myeloma, and diseases associated with amyloid-biofilm bacterial infections.

The tissue sample may be any suitable tissue sample including, but not limited to blood, serum, cerebral spinal fluid, nasal secretions, urine or other biological material from a subject at risk of an amyloid disease or amyloid-associated disease.

Conditions suitable for binding the polypeptides or multimers with an amyloid intermediate, if present in the tissue sample, to produce a binding complex will depend on specifics of the polypeptide(s) being used, the tissue sample, and the technique employed. Determining such suitable conditions are within the level of skill in the art based on the teachings herein.

In one embodiment of the diagnostic and prognostic methods disclosed herein, an amount of binding complexes higher than the LOD/LOQ/Cutoff for control samples serves to diagnose the subject as having an amyloid disease or amyloid-associated disease. In another embodiment, an amount of binding complexes higher than a control serves to prognose the subject as likely to develop an amyloid disease or amyloid-associated disease. In a further embodiment, an increased amount of binding complexes in a sample from a subject compared to an earlier sample from the subject indicates that a progression of an amyloid disease or amyloid-associated disease in the subject, or indicates that treatment the subject is receiving for an amyloid disease or amyloid-associated disease may need to be modified (i.e.: an alternative treatment substituted for the current treatment, an increased dosage of a therapeutic being administered, increased dosing frequency, alternative dosing methods, or complementary treatment approaches to current therapeutic etc.)

Any control may be used as determined appropriate by attending medical personnel. In one embodiment, the control may comprise a pre-determined level of binding complexes designated as "normal" (i.e.: not indicating the presence of α-sheet components that indicate amyloid disease or amyloid-associated disease). In another embodiment, the control may be a sample from a subject or subjects known not to have an amyloid disease or amyloid-associated disease. In other embodiments, the control may be a sample(s) from the same subject at one or more earlier time points; this embodiment is particularly useful for monitoring an amyloid disease or amyloid-associated disease, or monitoring efficacy of a treatment the subject is receiving for an amyloid disease or amyloid-associated disease.

EXAMPLES

Example 1: Improved Inhibition of Amyloid Fibril Formation with Alpha-Sheet Dimers We designed a series of peptides with unique sequences that all maintain a base α-sheet structure via templated, alternating L- and D-amino acids in the α-strands of the hairpin peptides. Each sequence was designed with a single cysteine residue (three letter code Cys and single letter code C), which acts as the site of directed dimerization via a disulfide bond through the oxidation of the thiol group (—SH) using DMSO at high pH (carbonate buffer, pH 9.6). Table 2 shows the sequences for 30 designed α-sheet monomer/dimer peptides and AP90 (our α-sheet peptide benchmark design). It should be noted that L amino acids are indicated with uppercase letters and D amino acids are indicated with lower-case letters (note that glycine is always indicated by 'G' as there is no differentiation for the L and D forms of this single hydrogen amino acid), and all sequences are indicated using the single letter codes. Additionally, X indicates the nonstandard amino acid Norleucine, Ac-indicates an acetylated N-terminus, and —NH2 indicates an amidated C-terminus.

TABLE 2

Sequences of α-sheet polypeptides

| Peptide Name (alias) | MW Monomer | MW Dimer | Sequence | SEQ ID NO: |
|---|---|---|---|---|
| AP090 | 2833.26 g/mol | na | Ac-RGEmNlSwMNEYSGWtMnLkMGR-NH2 | 31 |

TABLE 2-continued

Sequences of α-sheet polypeptides

| Peptide Name (alias) | MW Monomer | MW Dimer | Sequence | SEQ ID NO: |
|---|---|---|---|---|
| AP500 (AP195) | 2823.25 g/mol | 5646.50 g/mol | Ac-RGNwNeSkMNEYSGWmLmCtMGR-NH2 | 32 (1) |
| AP501 | 2899.34 g/mol | 5798.68 g/mol | Ac-RGNwNeSkMNEYYGWmLmCtMGR-NH2 | 33 (2) |
| AP502 | 2899.34 g/mol | 5798.68 g/mol | Ac-RGNwNeSkMneyygWmLmCtMGR-NH2 | 34 (3) |
| AP503 | 2899.34 g/mol | 5798.68 g/mol | Ac-RGNwNeSkMNEYYGWmLmTcMGR-NH2 | 35 (4) |
| AP504 | 2826.29 g/mol | 5652.58 g/mol | Ac-RGNcNeSkMNEYYGWmLmLtMGR-NH2 | 36 (5) |
| AP505 | 2898.40 g/mol | 5796.80 g/mol | Ac-RGNwCeSkMNEYYGWmLmLtMGR-NH2 | 37 (6) |
| AP506 | 2899.34 g/mol | 5798.68 g/mol | Ac-rgnWnEsKmneyygwMlMcTmgr-NH2 | 38 (7) |
| AP510 (AP193) | 3009.46 g/mol | 6018.92 g/mol | Ac-RGEmNyFwMNEYYGWtMnCkMGR-NH2 | 39 (8) |
| AP516 | 3009.46 g/mol | 6018.92 g/mol | Ac-rgeMnYfWmneyygwTmNcKmgr-NH2 | 40 (9) |
| AP520 (AP199) | 2823.25 g/mol | 5646.50 g/mol | Ac-RGEmNlSwMNEYSGWtMnCkMGR-NH2 | 41 (10) |
| AP521 | 2823.25 g/mol | 5646.50 g/mol | Ac-RGEcNLSWMNEYSGWtMnMkMGR-NH2 | 42 (11) |
| AP522 | 2899.35 g/mol | 5798.70 g/mol | Ac-RGEcNLSWMNEYYGWtMnMkMGR-NH2 | 43 (12) |
| AP523 | 2899.35 g/mol | 5798.70 g/mol | Ac-RGEcNlSwMneyyGWtMnMkMGR-NH2 | 44 (13) |
| AP524 | 2973.49 g/mol | 5946.98 g/mol | Ac-RCEmNlSwMneyyGWtMnMkMGR-NH2 | 45 (14) |
| AP525 | 2899.35 g/mol | 5798.70 g/mol | Ac-RGEmNlSwMneyyGWtMnMkCGR-NH2 | 46 (15) |
| AP526 | 2823.25 g/mol | 5646.50 g/mol | Ac-rGeMnLsWmneysGWTmNcKmGr-NH2 | 47 (24) |
| AP527 | 2899.35 g/mol | 5798.70 g/mol | Ac-rGeMnLsWmneyyGWTmNmKcGr-NH2 | 48 (25) |
| AP530 | 3009.46 g/mol | 6018.92 g/mol | Ac-RGEcNyFWMNEYYGWtMnMrMGK-NH2 | 49 (16) |
| AP531 | 2991.42 g/mol | 5982.84 g/mol | Ac-RGEcNyFWMNEYYGWtMnMrXGK-NH2 | 50 (17) |
| AP532 | 3008.51 g/mol | 6017.02 g/mol | Ac-RGEmCyFWMNEYYGWtMnMrXGK-NH2 | 51 (18) |
| AP533 | 2991.42 g/mol | 5982.84 g/mol | Ac-RGExNyFwMNEYYGWtMnMrCGK-NH2 XisNorleucine | 52 (19) |
| AP534 | 2991.42 g/mol | 5982.84 g/mol | Ac-RGExNyFwMNEYYGWtMnMcRGK-NH2 XisNorleucine | 53 (20) |
| AP535 | 3009.46 g/mol | 6018.92 g/mol | Ac-RGEyNcFWMNEYYGWtMnMrMGK-NH2 | 54 (21) |
| AP536 | 2991.42 g/mol | 5982.84 g/mol | Ac-RGElNyFwMNEYYGWtCnMrMGK-NH2 | 55 (22) |
| AP537 | 2959.44 g/mol | 5918.88 g/mol | Ac-RGElNyFwMNECYGWtMnMrMGK-NH2 | 56 (23) |
| AP550 | 2949.34 g/mol | 5898.68 g/mol | Ac-RGEmNyFwMNEYYGWtMnCkAGR-NH2 | 57 (26) |
| AP560 | 2889.22 g/mol | 2778.44 g/mol | Ac-RGEmNyFwMNEYYGWtAnCkAGR-NH2 | 58 (27) |
| AP570 | 2949.34 g/mol | 5898.68 g/mol | Ac-RGEmNyFwMNEYYGWtAnCkMGR-NH2 | 59 (28) |
| AP580 | 2959.35 g/mol | 5918.70 g/mol | Ac-RGEmNyFwMNEYYGWtLnCkVGR-NH2 | 60 (29) |

TABLE 2-continued

Sequences of α-sheet polypeptides

| Peptide Name (alias) | MW Monomer | MW Dimer | Sequence | SEQ ID NO: |
|---|---|---|---|---|
| AP590 | 2959.35 g/mol | 5918.70 g/mol | Ac-RGEmNyFwMNEYYGWtVnCkLGR-NH2 | 61 (30) |

The efficacy of peptide designs was investigated through the inhibition of fibril formation via ThT fluorescence assay. Peptides were co-incubated with 75 µM Aβ in PBS aggregation buffer and monitored for β-sheet formation via ThT fluorescence over time. In each case, Aβ alone (ie Aβ aggregating in PBS without any inhibitor) was run as the standard control and used for calculating % inhibition by the following equation:

$$\% \text{ inhibition} = 100 * \frac{\text{End Inhibitor value} - \text{Starting Abeta value}}{\text{End Abeta value} - \text{Starting Abeta value}}$$

Importantly, each value had its corresponding 'blank' subtracted from the raw data, ie: End Inhibitor value=Raw value at the end of the assay−value for peptide alone in PBS at the given concentration.

Figure 1:
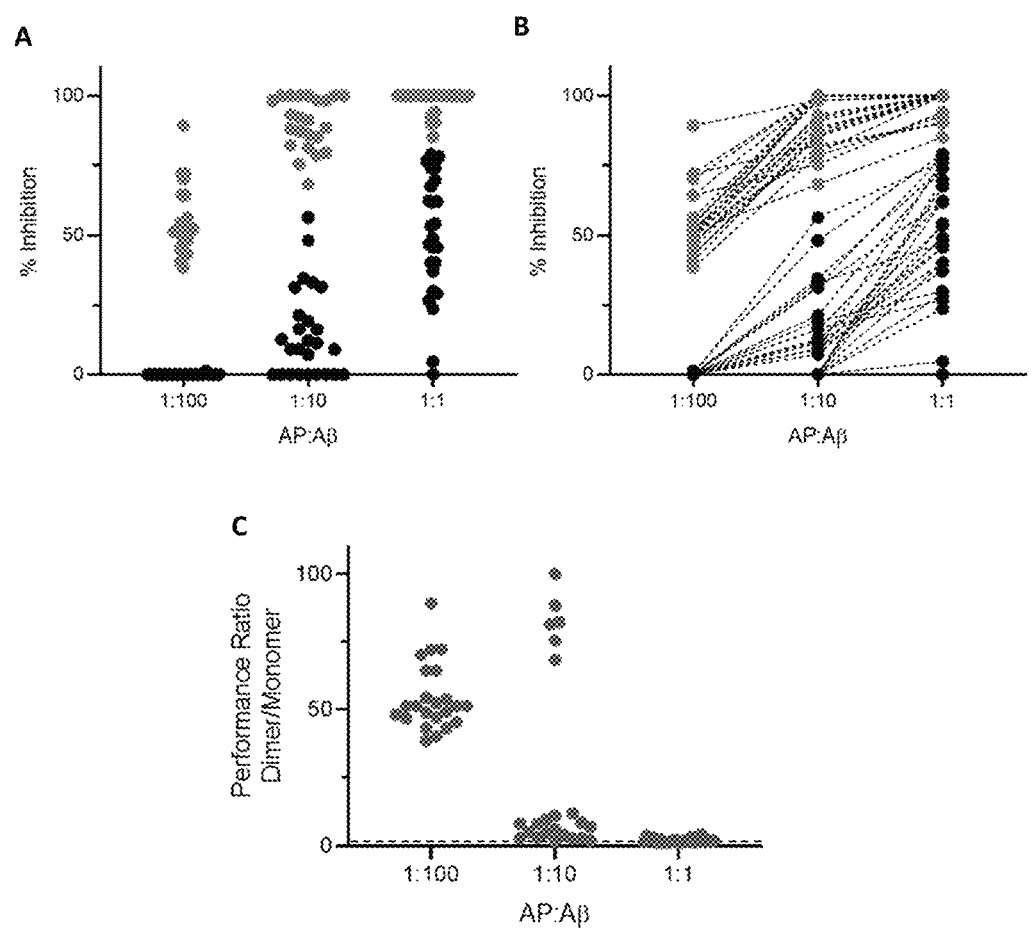
FIG. 1. Improved inhibition of dimers relative to monomers with respect to inhibition of fibril formation. (A) % inhibition with dimers. (B) Same as panel (A) but dashed lines connect individual designs. (C) Performance ratio, relative performance of dimers versus monomers as reflected in % inhibition dimers/% inhibition monomer (of the same design). As the ratio of the inhibitor drops, the monomer efficacy drops and the dimers outperform the monomers by a factor of 40-85×, significantly outperforming the expected 2× for a homo-dimer.

The 'blank' values never exceeded more than 2× starting Aβ value to ensure that overcorrection is not the source of efficacy in data processing—end Aβ value was on average 20× starting Aβ value. Peptide concentration was varied while Aβ concentration remained fixed to investigate the potency of the designs at equal- and sub-stoichiometric ratios of AP:Aβ (ratios investigated include 1:1, 1:10, and 1:100). Table 3 and FIG. 1 depict the performance of each unique peptide in their capacity to inhibit fibril formation via ThT assay—'m' following a sequence ID indicates it is the monomeric form and 'd' indicates it is the dimeric form. Dimeric forms of the α-sheet peptides are exceptionally potent, and far outpace their monomeric counterparts—all monomer forms showed ~0% inhibition at the 1:100 ratio, whereas the average dimer inhibition was 54.7%, the maximum was 89.2% and the minimum was 38.5%. FIG. 1c depicts this data as a 'performance ratio' calculated by dividing the % inhibition value for the dimer by the % inhibition value for the monomer and plotting that value—for cases where % inhibition for monomer (denominator) was 0 this ratio was calculated using a value of 1, so that the maximum performance ratio possible is 100. If dimeric peptides were simply 2× more efficient at inhibiting aggregation than their monomeric counterparts (due to having 2× the α-sheet 'faces' to bind) then this ratio would have a value of 2 for each ratio tested, indicated with the dashed horizontal black line in FIG. 1c.

TABLE 3

Results for % inhibition of fibril formation for peptide designs expressed as a molar ratio of AP design:Aβ42, moving from 1:1 to excess Aβ

| Design | 1:1 | SD | 1:10 | SD | 1:100 | SD |
|---|---|---|---|---|---|---|
| P1 (rc control) | 0 | 2.4 | 0 | 4.1 | | |
| P411 (β-hairpin control) | 4.6 | 2.2 | 0 | 3 | | |
| AP90 | 69.7 | 3.2 | 0 | 1.3 | | |
| AP500m | 76.6 | 3.5 | 9 | 4.6 | 0 | 0.3 |
| AP500d | 100 | 1.2 | 100 | 0.9 | 72.2 | 0.9 |
| AP501m | 29.2 | 4.1 | 0 | 2.4 | 0 | 0.7 |
| AP501d | 90 | 4.4 | 81.4 | 3.9 | 48.2 | 2.5 |
| AP502m | 23.8 | 1.6 | 0 | 1.8 | 0 | 1.1 |
| AP502d | 100 | 0.7 | 88.4 | 8.4 | 47.1 | 1.8 |
| AP503m | 61.8 | 7.3 | 16.2 | 1.7 | 0 | 1.3 |
| AP503d | 100 | 1.2 | 100 | 1.8 | 70.1 | 2.3 |
| AP504m | 30 | 1.3 | 19.2 | 1.7 | 0 | 0.8 |
| AP504d | 100 | 0.6 | 100 | 3 | 64.3 | 1.2 |
| AP505m | 26.8 | 1.5 | 16.4 | 2.8 | 0 | 0.7 |
| AP505d | 100 | 0.3 | 79.5 | 4.1 | 51.4 | 1.3 |
| AP506m | 67.6 | 2 | 0 | 1.4 | 0 | 1.1 |
| AP506d | 100 | 0.8 | 100 | 4.4 | 49.1 | 1 |
| AP510m | 79.1 | 5.4 | 48.2 | 4.4 | 1.2 | 1.1 |
| AP510d | 100 | 3.5 | 100 | 2.3 | 56.3 | 0.8 |
| AP516m | 76.6 | 9.5 | 56.4 | 5.7 | 0 | 0.5 |
| AP516d | 100 | 3.2 | 98.2 | 1.3 | 51.3 | 1.2 |
| AP520m | 47 | 2.8 | 33.1 | 1.9 | 0 | 1.4 |
| AP520d | 100 | 1 | 91.2 | 2.1 | 45.3 | 0.9 |
| AP521m | 74 | 3.1 | 34.6 | 2.2 | 0 | 1.1 |
| AP521d | 100 | 1.8 | 100 | 3.9 | 54.3 | 2.2 |
| AP522m | 45.7 | 5.8 | 12.6 | 1.6 | 0 | 1.1 |
| AP522d | 100.0 | 2.1 | 88.1 | 0.3 | 52.4 | 0.5 |
| AP523m | 49 | 5.8 | 9 | 1.5 | 0 | 2.2 |
| AP523d | 100 | 3.2 | 87.3 | 3.1 | 40.3 | 1.3 |
| AP524m | 45.8 | 1.2 | 7.2 | 2.3 | 0 | 0.6 |
| AP524d | 100.0 | 0.9 | 86.1 | 1.1 | 43.1 | 2.2 |
| AP525m | 53.5 | 1.3 | 12.1 | 1.4 | 0 | 1.2 |
| AP525d | 99.7 | 0.8 | 98.3 | 1.2 | 89.2 | 1.0 |
| AP526m | 63.2 | 1.1 | 12.4 | 1 | 0 | 0.5 |
| AP526d | 100.0 | 1 | 88.6 | 1.3 | 62.4 | 1.6 |
| AP527m | 54.2 | 1.1 | 14.3 | 1.2 | 0 | 1.9 |
| AP527d | 100 | 0.9 | 96.2 | 1.1 | 86.4 | 1.5 |
| AP530m | 78.2 | 2.5 | 31.6 | 2.2 | 0 | 1.4 |
| AP530d | 100 | 1.2 | 93.2 | 1.1 | 48.8 | 0.9 |
| AP531m | 37.2 | 1.1 | 9.1 | 1.6 | 0 | 1.1 |
| AP531d | 92.6 | 1.5 | 78.6 | 2.4 | 38.5 | 1.4 |
| AP532m | 62.1 | 2.1 | 0 | 0.8 | 0 | 1.3 |
| AP532d | 94.2 | 2.2 | 75.4 | 3.2 | 64.3 | 1.1 |
| AP533m | 40.3 | 1.2 | 0 | 1.4 | 0 | 2.1 |
| AP533d | 85.2 | 3.1 | 68.2 | 1.5 | 51.4 | 1.0 |
| AP534m | 40.2 | 4.4 | 11.2 | 1.6 | 0 | 2.2 |
| AP534d | 100 | 0.6 | 92.2 | 2.1 | 51.3 | 2 |
| AP535m | 62.3 | 0.9 | 31.3 | 0.7 | 0 | 0.4 |
| AP535d | 100 | 1.2 | 98.2 | 1.4 | 53.7 | 1.4 |
| AP536m | 74.1 | 3.3 | 21.4 | 2.4 | 0 | 0.9 |
| AP536d | 100.0 | 1.0 | 85.2 | 2.3 | 43.1 | 1.6 |
| AP537m | 54.2 | 2.8 | 0 | 0.9 | 0 | 1.2 |
| AP537d | 90.2 | 2.2 | 82.3 | 3.1 | 72 | 1.1 |
| AP540m | 67.4 | 1.2 | | | | |

(m = monomer, d = dimer)

Additional Methods of Dimerization

Dimerization methods other than disulfide binding can be used to generate the dimers of the disclosure, and may provide benefits such as improving stability, particularly in a reducing environment such as inside cells for therapeutics for diseases with intracellular toxic oligomers.

For example, Bis(maleimido)ethane (BMOE) and 1,1'-(2,2'-oxybis(ethane-2,1-diyl))bis(1H-pyrrole-2,5-dione) (MalPEG1) were used to link two monomers via their Cys residues.

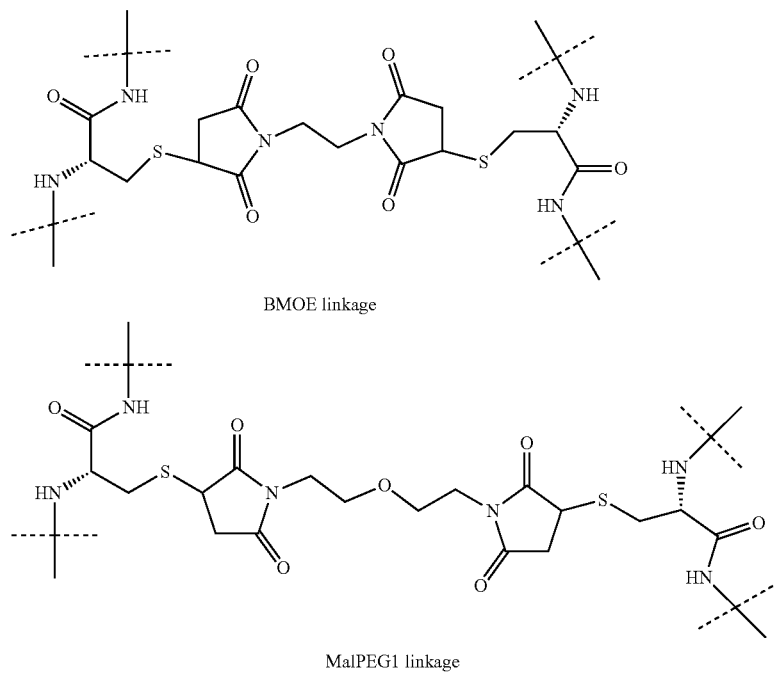

BMOE linkage

MalPEG1 linkage

Inhibition of Abeta aggregation was assessed in our standard ThT assay and the results can be compared to those in the table comparing different peptides in their monomeric and dimeric forms with 10-fold excess of Abeta.

TABLE 4

Comparison of monomer and dimeric alpha-sheet designs with different dimerization linkers

| Peptide | | % Inhibition 1:10 (AP peptide:Abeta42) |
|---|---|---|
| AP527m | | 14% |
| AP527d | (S-S) | 96% |
| AP527d | (BMOE) | 80% |
| AP527d | (MalPEG1) | 75% |

(m = monomer, d = dimer)

As with the disulfide-bonded form, the dimers with the longer linkers are providing much more than a 2× response. These linkages help target intracellular amyloid diseases, such as Huntington's disease.

Amyloid Inhibition in Other Mammalian and Bacterial Amyloid Systems

These improved α-sheet designs are not limited to AD, they show improved inhibition in a variety of amyloid systems by virtue of targeting the common alpha-sheet structure formed by amyloidogenic peptides and proteins during amyloidogenesis independent of sequence and starting structure. As an example, inhibition of amyloid formation by islet amyloid polypeptide (IAPP), type 2 diabetes, is also more effective for dimeric α-sheet peptides (Table 5). Independent of sequence, the dimers outperform the monomers by greater than a 2× effect, which is particularly evident when the IAPP is in excess.

TABLE 5

Inhibition of IAPP with monomeric and dimeric designs. Notice the large increase in inhibition with dimerization particularly as the amount of AP peptide relative to IAPP drops.

| | Ratio AP:IAPP design (% inhibition) | | |
|---|---|---|---|
| Peptide | 1:1 | 4:1 | 10:1 |
| AP90m | 40 | 42 | 65 |
| AP5m | 9 | 10 | 85 |
| AP193d | 99 | 98 | 99 |
| AP493d | 99 | 97 | 100 | m = monomer,
d = dimer

Figure 2:
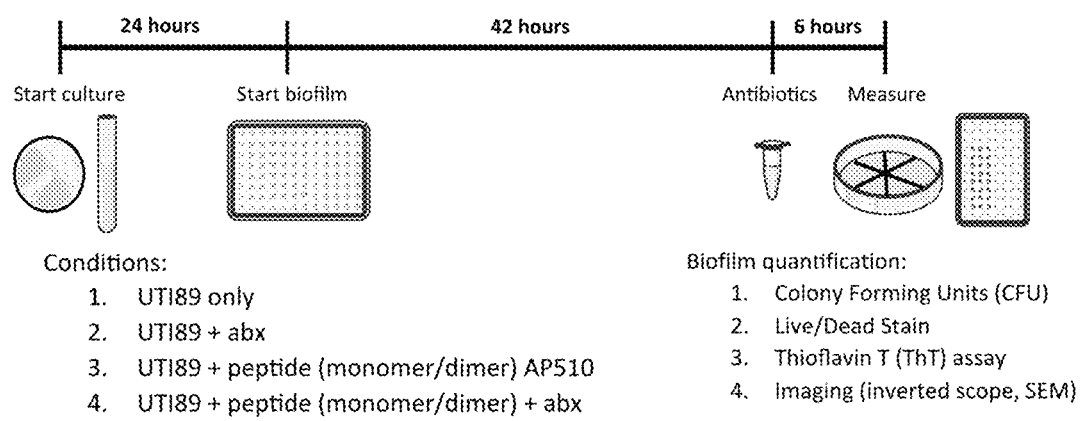
FIG. 2. Protocol to test inhibition of biofilm amyloid formation in live E. coli. Amyloid formation is assessed through a ThT assay like that used with Abeta and IAPP above. In addition, inhibition of amyloid disrupts the biofilm, leading to an increase in planktonic free-floating bacteria cells, which are then susceptible to antibiotics.

In addition, to mammalian amyloid proteins, the improved inhibition of the dimeric designs is also observed in bacterial amyloid systems. As an example, results using a clinical isolate of *E. coli* from a patient with a persistent urinary tract infection are presented. The experimental approach is illustrated in FIG. 2. UTI89 is a uropathogenic *E. coli* strain that uses the amyloid fibril structure to form a robust biofilm in vivo that resists major disruption from antibiotic treatment. If the biofilm architecture can be disrupted, antibiotics should be more effective. The α-sheet-mediated amyloid formation in mammalian systems also apply to bacterial amyloid used to stabilize protective biofilms in both gram negative and positive bacteria.

Figure 3:
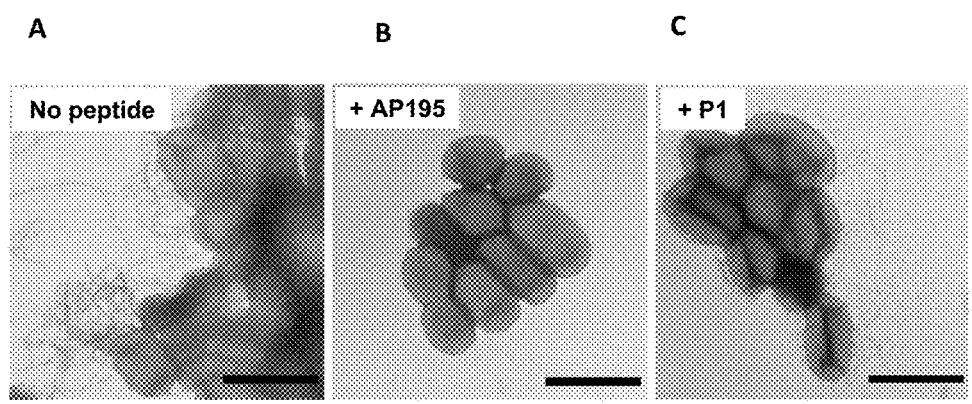
FIG. 3. TEM images reveal extensive curli amyloid fibril formation in (A) peptide-free biofilms and biofilms grown in the presence of (C) P1, but not those grown in the presence of (B) AP195 dimer (Scale bars=2 μm). P1 and AP195 were added at equimolar concentrations. AP195 is an α-sheet peptide and P1 is a random coil control.

FIG. 3 illustrates the amyloid formation in the live *E. coli* without treatment and the inhibition of fibril formation in the presence of the AP195 dimer. The random coil peptide control (P1) had no effect.

Figure 4:
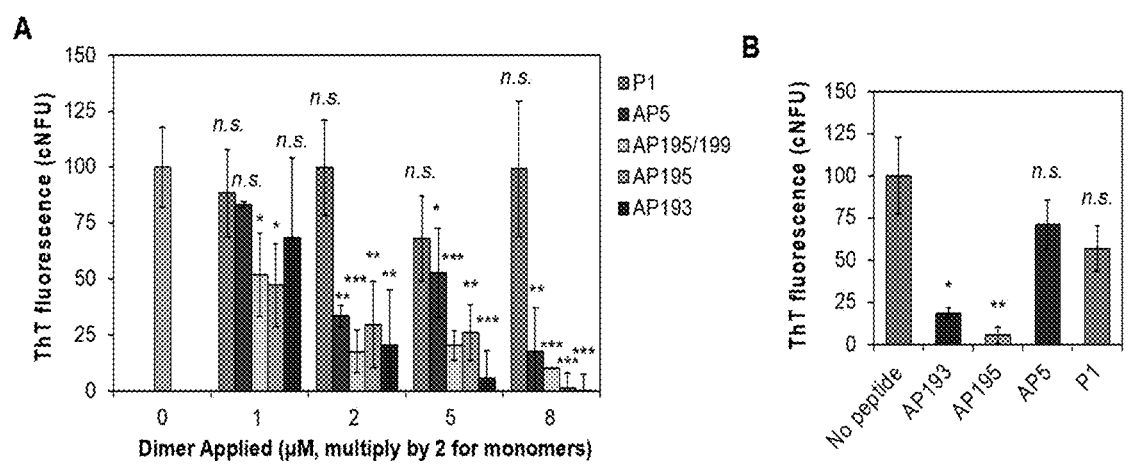
FIG. 4. Inhibition of amyloid formation by alpha-sheet designs in live E. coli clinical isolates. (A) The dimeric designs AP193, AP195, AP195/199, and AP5 monomer caused a dose-dependent reduction in amyloid content in UTI89 WT biofilms, as measured by ThT fluorescence. The concentrations are provided for the dimers, but the P1 and AP5 monomers were double that concentration to provide the same number of monomer units for comparison of the designs (ex. where it says 5 μM applied AP5, it was actually 10 μM). cNFU=corrected, normalized fluorescence units, where normalized signals were corrected by the nonspecific ThT fluorescence of E. coli UTI89 ΔcsgA biofilms. (B) Synthetic α-sheet peptides AP193 and AP195 decreased the ThT fluorescence of E. coli GERB319 biofilms, a clinical UTI isolate with resistance to gentamicin and ciprofloxacin (the dimeric peptides were added at 8 μM and AP5 and P1 were 16 μM to provide the same monomer equivalents). The unstructured control peptide P1 had no effect when applied at the same concentration. For panels (C) and (D), error bars represent the standard deviation from the mean of at least three replicates, and p-values are indicated as follows: * indicates $p<0.05$,  indicates $p<0.01$, * indicates $p<0.001$, and n.s. indicates $p≥0.05$.

Varying doses of different synthetic α-sheet peptides (AP193, AP195, AP195/199 dimers, or AP5 monomer) or an unstructured control peptide (P1) were added to replicate cultures at the time of inoculation. AP5 is a 23-residue, monomeric α-sheet hairpin. AP195 and AP193 are homodimers consisting of two identical α-sheet hairpins, and AP195/199 is a heterodimer consisting of one AP195 monomer and one AP199 monomer. After 48 hours of growth, the biofilms were rinsed, homogenized, and stained with the amyloid dye Thioflavin T (ThT), which fluoresces upon binding β-sheet fibrils and serves as a reporter of amyloid fibril content. ThT also binds nonspecifically to the bacterial cell surface, so biofilms of a UTI89 ΔcsgA knockout strain were grown in parallel to provide an estimate of nonspecific ThT fluorescence. This non-specific binding signal was subtracted from UTI89 WT signals to produce the corrected fluorescence values (cNFU) shown in FIG. 4. The homodimers and heterodimer were much more potent than the AP5 monomer and the P1 random coil control had no effect (FIG. 4A).

To investigate the applicability of synthetic α-sheet peptides beyond the UTI89 system, we obtained E. coli isolates from pediatric patients who had presented with antibiotic-resistant urinary tract infections. PCR confirmed the presence of the csgA gene in all isolates, but only those that exhibited curliated, "rdar" colony morphotypes on YESCA+ Congo Red agar were selected for further characterization. As in the UTI89 WT system, AP193 and AP195 caused a significant decrease in ThT fluorescence of the gentamicin/ciprofloxacin-resistant strain GERB319 (FIG. 4B), while the random coil control peptide and the AP5 monomer had no effect at twice the concentration.

Figure 5:
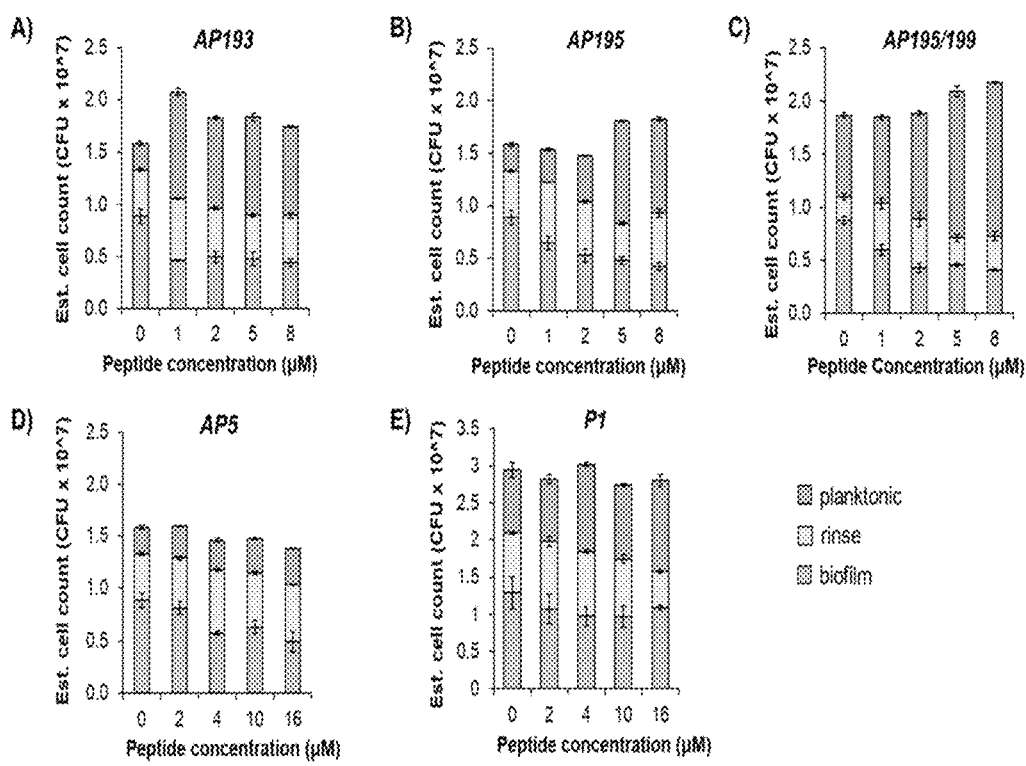
FIG. 5. Treatment of E. coli with dimeric APs shifts more cells into the planktonic state than monomer and greatly reduces the bacterial content in the biofilm. (A) AP193d, (B) AP195d, (C) AP195/199 heterodimer, (D) AP5 monomer, (E) P1. When free floating and planktonic, the bacteria are susceptible to antibiotics and the host immune system. Estimation of bacterial cell counts in biofilm ThT assays. Cells were collected and homogenized during each phase of the assay (planktonic, rinse, biofilm) and the number of cells was estimated according to the optical density of samples at 600 nm. Peptides did not affect growth; instead, they shifted bacteria from the biofilm-associated state to the planktonic state. Error bars indicate the standard deviation from the mean of three replicates.
Figure 6:
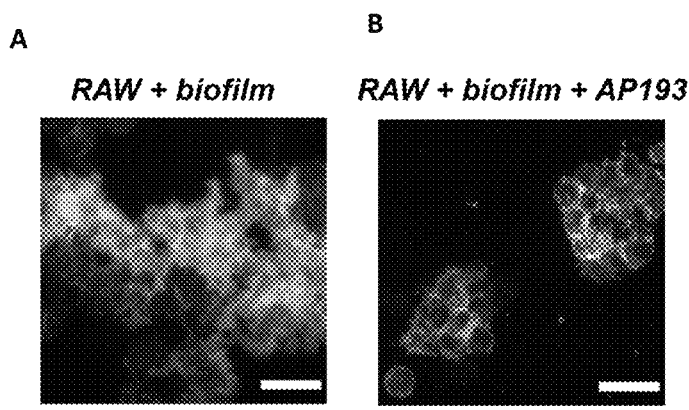
FIG. 6. (A) Fluorescence microscopy (scale bars=30 m) images after 1 h coincubation of E. coli UTI89 SLC-719 (GFP) with RAW 264.7 macrophages (Alexa Fluor 647). (B) Phagocytosis increased in biofilms cultivated in the presence of 8 μM AP193d. Improved phagocytosis in the presence of AP193 dimer was attributed to improved biofilm solubility and increased availability of individual bacteria.

The effect of inhibiting amyloid fibril formation destabilized the biofilms, such that there was an increase in free, planktonic bacteria. The effect was much more pronounced for the dimers even at half the dose of monomer (compare the top grey bar in each plot of FIG. 5). This shift in the cells resulted in a larger number of unprotected, planktonic bacteria, which were more susceptible to antibiotics and immune clearance. For example, the resistant UTI89 strain became 13,000-fold more susceptible to gentamycin with co-administration of AP designs. Similarly, the bacteria became more susceptible to phagocytosis by macrophages, as shown in FIG. 6.

Materials and Methods

Peptides were synthesized using a CEM Liberty Blue™ microwave peptide synthesizer with Fmoc-based DIC/Oxyma chemistry according to standard methods. Peptides were all purified on a Shimadzu Preparatory HPLC system according to standard methods. Peptides were verified for molecular weight using a Bruker Ion Trap™ ESI-MS system (either Bruker Esquire or Bruker amaZon™ Speed was utilized), sequences verified using MS/MS, and structure verified via secondary structure validation on a Jasco™ Circular Dichroism spectrometer (either J-720 or J-1500 system was utilized).

Dimeric peptides were formed using the purified monomeric peptide by first dissolving ~5 mg of pure monomer peptide in 1 mL of DMSO, adding 19 mL of pH 9.6 carbonate buffer, mixing with stirring for 2h at 37 C followed by stirring overnight 16h at room temperature. The dimer was then purified from non-dimerized monomer via HPLC and validated under the same methods used for the monomeric forms.

Aβ aggregation and fibril formation, as well as inhibition experiments with α-sheet peptides, were monitored via ThT fluorescence according to the procedure, as follows. Prepare 6 mM NaOH (aq) and 22 μM ThT solutions. Remove Aβ42 film(s) from −80° C. Equilibrate to RT 5 min on benchtop. Add enough volume of 6 mM NaOH (aq) to the Aβ42 film for a 0.75 mg/mL solution. Sonicate the 0.75 mg/mL mixture for 5 min in a bath sonicator to dissolve the Aβ42. After sonication, tap the tube containing the solution with your finger to mix. If it is observed that the peptide has not dissolved (i.e. particulate remains), continue sonicating in 5 min increments, checking after each for dissolution. Once Aβ42 is dissolved, filter the 0.75 mg/mL solution through a 0.22 μm cellulose acetate centrifuge filter to remove insoluble material. Centrifuge the sample for 2-3 min at low RPM (4.3×g) to pass all solution through the filter. Perform UV/Vis spectroscopy on the filtered Aβ42 solution to determine the exact Aβ42 concentration with extinction coefficient at 280 nm of 1490 $M^{-1}$ $cm^{-1}$.

Incubate Aβ42 stock solution for 4 hr in the 25 C incubator for NaOH treatment. After this incubation, the stock can be stored at 4° C. for up to one week for use in future sample preparations. Determine the total volume of inhibitor solutions that will need to be made in the dye-containing aggregation solvent. Prepare a slight excess of all inhibitor solutions by diluting small aliquots of stock solutions (10-20 mg/mL) to the desired concentration(s) with dye-containing aggregation solvent/buffer (PBS). After the initial dilution, determine the exact concentrations of all peptide inhibitors using UV/Vis spectroscopy, and make further dilutions/additions as needed. Determine the volume of Aβ42 stock solution (Vstock) needed to prepare a single sample. This will depend on: the stock concentration (cstock), the desired final concentration (cfinal, and the well volumes for the fluorescence plate that will be used. The final sample volume (Vfinal) must be less than the total volume of the well, but greater than the minimum volume required to coat the bottom surface of the well. Generally, for 96-well plates use 150 μL, and for 384-well plates use 60 μL. Use the following equation: Vstock=(Vfinal×cfinal)/(cstock). Once the Aβ42 has had full NaOH treatment, prepare the final samples by pipetting 3× Vstock aliquots into a lo-bind tube, and diluting them to 3× Vfinal with the appropriate dye-containing solvent (either aggregation solvent/buffer or aggregation solvent/buffer containing inhibitor). Mix up and down 4 times without changing the setting on the pipette. Seal the plate with film and move it to the plate reader to perform regular ThT fluorescence assays using an excitation wavelength of 438 nm and emission wavelength of 485 nm. IAPP aggregation and inhibition were evaluated using the same general protocols with some minor modifications.

Methods for BMOE Dimerization of AP Designs

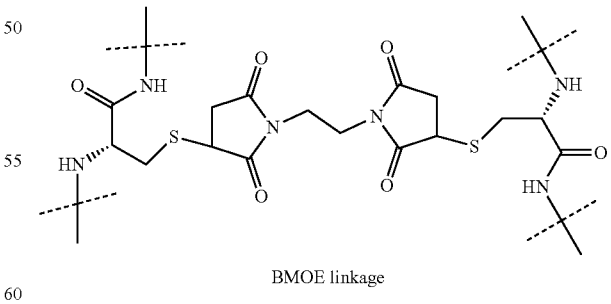

BMOE linkage

A stock solution of 6 mM (1.3 mg/mL) Bis(maleimido)ethane (BMOE; Thermo Fisher Scientific) in N,N-Dimethylformamide (DMF; Millipore Sigma) was prepared in a 2 mL Eppendorf tube. The BMOE was weighed (2.0 mg) and transferred to the 2 mL Eppendorf tube, 1.5 mL DMF added with a micropipette, and the tube repeatedly inverted until complete dissolution was achieved. A stock solution of 0.1 M, pH 8 Tris Buffer was prepared in a 50 mL conical tube: 0.444 g of Trizma HCl (Sigma Aldrich) and 0.265 g of Trizma base (Sigma Aldrich) were added to the 50 mL tube and dissolved in 50 mL Milli-Q DI H$_2$O. The pH was verified with a pH probe (Mettler Toledo) and double checked with pH paper (Fisher Scientific). In a 20 mL glass scintillation vial with a stir bar, a 1.3 mM (3.9 mg/mL) solution of AP527 was prepared in 50% DMF, 50% stock Tris Buffer using 6.2 mg of peptide and 1.6 mL of solution. AP527 concentration was checked with a NanoDrop™ 2000c Spectrometer (Thermo Fisher Scientific) using an extinction coefficient of 13,940 M$^{-1}$ cm$^{-1}$ at 280 nm. Using a micro pipette, an appropriate amount of the BMOE in DMF stock solution was added to the peptide solution to achieve ~0.5 mol. Eq. ratio of BMOE with respect to AP527. The solution was mixed at 1000 rpm at RT for ~16 hours, at which point reaction completion was verified using ultra high-performance liquid chromatography mass spectrometry (LCMS). A small amount (exact weight not critical) of Tris(2-carboxyethyl)phosphine (Sigma Aldrich) was added to the scintillation vial and the solution mixed at 1000 rpm at RT for one hour to degrade any unwanted, disulfide linked dimer side products. The solution was then diluted 3-fold with MilliQ DI H$_2$O, frozen in a −80 C freezer and lyophilized. The crude dimer was purified by Reverse phase-HPLC (Waters XSelect™ CSH C18 OBD Prep Column). Purified dimer was confirmed by LCMS, lyophilized, and stored at −80 C.

Methods for MalPEG1 Dimerization of AP Designs (Thermo Fisher Scientific) using an extinction coefficient of 13,940 M$^{-1}$ cm$^{-1}$ at 280 nm. Using a micro pipette, an appropriate amount of the MalPEG1 in DMF stock solution was added to the peptide solution to achieve ~0.5 mol. Eq. ratio of MalPEG1 with respect to AP527. The solution was mixed at 1000 rpm at RT for ~16 hours, at which point reaction completion was verified using ultra high-performance liquid chromatography mass spectrometry (LCMS). A small amount (exact weight not critical) of Tris(2-carboxyethyl)phosphine (Sigma Aldrich) was added to the scintillation vial and the solution mixed at 1000 rpm at RT for one hour to degrade any unwanted, disulfide linked dimer side products. The solution was then diluted 3-fold with Milli-Q DI H$_2$O, frozen in a −80 C freezer and lyophilized. The crude dimer was purified by Reverse phase-HPLC (Waters XSelect™ CSH C18 OBD Prep Column). Purified dimer was confirmed by LCMS, lyophilized, and stored at −80 C.

Biofilm Culturing and Assays

Overnight cultures were grown in LB medium for ~18 h. Bacteria were collected by centrifugation at 8000×g for 3 min, resuspended in YESCA broth (53)+4% v/v DMSO, and diluted to an optical density of 0.1 at 600 nm. Peptide stocks were dissolved in water and concentrations were determined by Nanodrop™ (Thermo Scientific; Waltham, MA). 20 µL of peptide stock and/or sterile ddH2O was added to each well of a sterile 48 well plate such that the final peptide concentration was 0, 2, 4, 10, or 16 µM (0, 1, 2, 5, or 8 µM for dimeric peptides), then 180 µL of diluted bacteria culture was added on top. Plates were covered, sealed in plastic

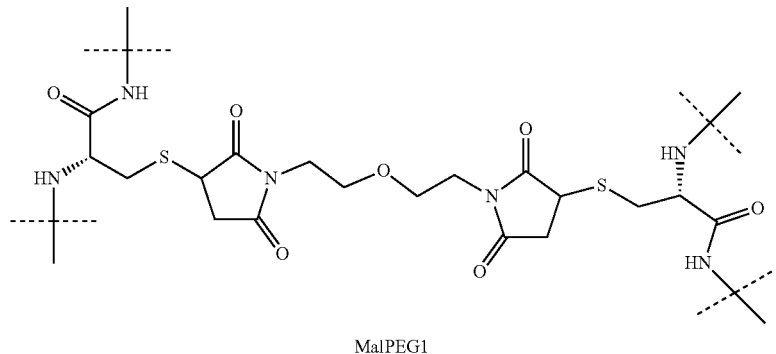

MalPEG1

A stock solution of 36 mM (9.6 mg/mL) 1,1'-(2,2'-oxybis (ethane-2,1-dioyl))bis(1H-pyrrole-2,5-dione) (MalPEG1; Abosyn) in N,N-Dimethylformamide (DMF; Millipore Sigma) was prepared in a 2 mL Eppendorf tube. The MalPEG1 was weighed (4.8 mg) and transferred to the 2 mL Eppendorf tube and 0.5 mL DMF added with a micropipette. The solution was vortexed at 3000 rpm (FisherBrand) for ~1 minute, and then repeatedly inverted until complete dissolution was achieved. A stock solution of 0.1 M, pH 8 Tris Buffer was prepared in a 50 mL conical tube: 0.444 g of Trizma HCl (Sigma Aldrich) and 0.265 g of Trizma base (Sigma Aldrich) were added to the 50 mL tube and dissolved in 50 mL Milli-Q DI H$_2$O. The pH was verified with a pH probe (Mettler Toledo) and double checked with pH paper (Fisher Scientific). In a 20 mL glass scintillation vial with a stir bar, a 0.79 mM (2.3 mg/mL) solution of AP527 was prepared in 50% DMF, 50% stock Tris Buffer using 9.5 mg of peptide and 4.14 mL of solution. AP527 concentration was checked with a NanoDrop™ 2000c Spectrometer bags, and incubated at 26° C. for 48 h. After growth, planktonic cells and medium were removed and biofilms were rinsed once with 250 µL PBS. Planktonic cells were spun down and resuspended in PBS, and the optical density of both planktonic and rinse samples was determined at 600 nm to estimate cell densities. The PBS solution was removed and biofilms were resuspended in 250 µL PBS+20 µM ThT. Biofilms were homogenized by vigorous pipetting (30× per well), 3 min sonication, and 1 min on a plate shaker. 100 µL of each biofilm suspension was then transferred to a black-walled, clear-bottom 96 well plate for measurements in a plate reader (PerkinElmer; Waltham, MA). ThT fluorescence was measured at 438/495 nm as a proxy for amyloid formation, and biofilm absorbance was measured at 600 nm to estimate bacterial cell density. For UTI89 WT, biofilm ThT fluorescence values were normalized to the average value of peptide-free controls, and then the average fluorescence value of UTI89 ΔcsgA samples was subtracted to account for nonspecific binding. In the case of antibiotic susceptibility tests, biofilms were cultivated in the same manner, but 100 µL YESCA or 100 µL YESCA supplemented with 900 µg/mL Gm was added to wells 6 h before the end of incubation. After incubation, planktonic cells and medium were removed and biofilms were rinsed once in sterile PBS. Biofilms were then resuspended in sterile PBS, homogenized by ultrasonication for 5 s on ice, and then diluted in tenfold increments for CFU plate counts with the drop plate method.

To assess susceptibility of the bacteria to immune cells, biofilms of green fluorescent *E. coli* UTI89 SLC-719 were grown in YESCA broth+4% DMSO for 48 h in 48 well polystyrene plates at 26° C. Planktonic cells and medium were removed and biofilms were washed once with sterile PBS. RAW 264.7 macrophage cells were grown in complete medium (DMEM+10% fetal bovine serum+1× penicillin/streptomycin) to passage 12±2, stained with CellTrace™ Red (Thermo Fisher; Waltham, MA), and resuspended in FACS buffer (PBS+5% FBS). For coincubation, 250 µL of stained macrophage suspension was applied on top of each biofilm at a MOI of 1:100 (macrophage:bacteria). Planktonic bacteria and macrophages were coincubated separately at the same ratio. Coincubation proceeded for 1 h at 37° C. prior to detachment of cells and biofilm by gentle scraping.

Discussion

The new class of dimeric α-sheet designs described here provide a significant improvement over the monomeric counterparts across different amyloid systems both mammalian and bacterial, as well as being applicable to different applications due to their improved binding.

REFERENCES

1. Alzheimer's Association. (2019) *Alzheimer's disease facts and figures*. [Ebook]. Chicago.
2. Masters, C. L. et al. (2015) Alzheimer's disease. *Nat. Rev. Disease Primers* 1, 15056.
3. Chiti, F., and Dobson, C. M. (2006) Protein misfolding, functional amyloid, and human disease. *Annu. Rev. Biochem.* 75, 333-366.
4. Braak, H., and Braak, E. (1991) Neuropathological staging of Alzheimer-related changes. *Acta Neuro.* 82, 239-259.
5. Giuffrida, M. L., et al. (2010) The monomer state of 0-amyloid: Where the Alzheimer's disease protein meets physiology. *Rev. Neurosci.* 21, 83-93.
6. Whitson, J. S., Selkoe, D. J., and Cotman, C. W. (1989) Amyloid R protein enhances the survival of hippocampal neurons in vitro. *Science* 243, 1488-1490.
7. Morley, J. E., et al. (2010) A physiological role for amyloid-β protein: Enhancement of learning and memory. *J. Alz. Dis.* 19, 441-449.
8. Bishop, G. M., and Robinson, S. R. (2004) Physiological roles of amyloid-β and implications for its removal in Alzheimer's disease. *Drugs & Aging* 21, 621-630.
9. Hiltunen, M., van Groen, T., and Jolkkonen, J. (2009) Functional roles of amyloid-beta protein precursor and amyloid-beta peptides: Evidence from experimental studies. *J. Alz. Dis.* 18, 401-412.
10. Koudinov, A. R., and Berezov, T. T. (2004) Alzheimer's amyloid-β (Aβ) is an essential synaptic protein, not neurotoxic junk. *Acta Neurobiol. Exp.* 64, 71-79.
11. Jaunmuktane, Z., et al. (2015) Evidence for human transmission of amyloid-β pathology and cerebral amyloid angiopathy. *Nature* 525, 247-250.
12. Selkoe, D. J. (2001) Alzheimer's disease: Genes, proteins, and therapy. *Physiol. Rev.* 81, 741-766.
13. Mullan, M., et al. (1992) A pathogenic mutation for probable Alzheimer's disease in the APP gene at the N-terminus of beta-amyloid. *Nat. Genet.* 1, 345-347.
14. Masters, C. L., et al. (1985) Amyloid plaque core protein in Alzheimer disease and Down syndrome. *Proc. Natl. Acad. Sci. USA* 82, 4245-4249.
15. Glenner, G. G., Wong, C. W., Quaranta, V., and Eanes, E. D. (1984) The amyloid deposits in Alzheimer's disease: Their nature and pathogenesis. *Appl. Pathol.* 2, 357-369.
16. McLean, C. A., et al. (1999) Soluble pool of Abeta amyloid as a determinant of severity of neurodegeneration in Alzheimer's disease. *Ann. Neurol.* 46, 860-866.
17. Haass, C., and Selkoe, D. J. (2007) Soluble protein oligomers in neurodegeneration: Lessons from the Alzheimer's amyloid β-peptide. *Nat. Rev. Mol. Cell Biol.* 8, 101-112.
18. Lambert, M. P., et al. (2001) Vaccination with soluble Abeta oligomers generates toxicity-neutralizing antibodies. *J. Neurochem.* 79, 595-605.
19. Wang, J., Dickson, D. W., Trojanowski, J. Q., and Lee, V. M. (1999) The levels of soluble versus insoluble brain Abeta distinguish Alzheimer's disease from normal and pathologic aging. *Exp. Neurol.* 158, 328-337.
20. Yang, T., Li, S., Xu, H., Walsh, D. M., and Selkoe, D. J. (2017) Large soluble oligomers of amyloid β-protein from Alzheimer brain are far less neuroactive than the smaller oligomers to which they dissociate. *J. Neurosci.* 37, 152-163.
21. Lambert, M. P., et al. (1998) Diffusible, nonfibrillar ligands derived from Abeta1-42 are potent central nervous system neurotoxins. *Proc. Natl. Acad. Sci. USA* 95, 6448-6453.
22. Ahmed, M., et al. (2010) Structural conversion of neurotoxic amyloid-β(1-42) oligomers to fibrils. *Nat. Struct. Mol. Biol.* 17, 561-567.
23. Hardy, J. A., and Higgins, G. A. (1992) Alzheimer's disease: the amyloid cascade hypothesis. *Science* 256, 184-185.
24. Sakono, M., and Zako, T. (2010) Amyloid oligomers: Formation and toxicity of Abeta oligomers. *FEBS J.* 277, 1348-1358.
25. Zahs, K. R., and Ashe, K. H. (2013) β-Amyloid oligomers in aging and Alzheimer's disease. *Front. Aging Neurosci.* 5, 28.
26. Hsia, Y., et al. (1999) Plaque-independent disruption of neural circuits in Alzheimer's disease mouse models. *Proc. Natl. Acad. Sci. USA* 96, 3228-3233.
27. Tomiyama, T., et al. (2008) A new amyloid beta variant favoring oligomerization in Alzheimer's-type dementia. *Ann. Neurol.* 63, 377-387.
28. Jack Jr, C. R., et al. (2013) Tracking pathophysiological processes in Alzheimer's disease: An updated hypothetical model of dynamic biomarkers. *Neurology* 12, 207-216.
29. Li, S., and Selkoe, D. J. (2020) A mechanistic hypothesis for the impairment of synaptic plasticity by soluble Abeta oligomers from Alzheimer's brain. *J. Neurochem.* 154, 583-597.
30. Ashe, K. H. (2020) The biogenesis and biology of amyloid p oligomers in the brain. *Alz. Demen.* 16, 1561-1567.
31. Mucke, L., et al. (2000) High-level neuronal expression of Abeta(1-42) in wild-type human amyloid protein precursor transgenic mice: Synaptotoxicity without plaque formation. *J. Neurosci.* 20, 4050-4058.

32. Hsia, A. Y., et al. (1999) Plaque-independent disruption of neural circuits in Alzheimer's disease mouse models. *Proc. Natl. Acad. Sci. USA* 96, 3228-3233.

33. Leuzy, A., Heurling, K., Ashton, N. J., Scholl, M., and Zimmer, E. R. (2018) In vivo detection of Alzheimer's disease. *Yale J. of Biol. and Med.* 91, 291-300.

34. Counts, S. E., Ikonomovic, M. D., Mercado, N., Vega, I. E., and Mufson, E. J. (2017) Biomarkers for the early detection and progression of Alzheimer's Disease. *Neurother.* 14, 35-53.

35. Price, J. L., and Morris, J. C. (1999) Tangles and plaques in nondemented aging and "preclinical" Alzheimer's disease. *Ann. Neurol.* 45, 358-368.

36. Herukka, S. K., et al. (2017) Recommendations for cerebrospinal fluid Alzheimer's disease biomarkers in the diagnostic evaluation of mild cognitive impairment. *Alz. & Dem.* 13, 285-295.

37. Olsson, B., et al. (2016) CSF and blood biomarkers for the diagnosis of Alzheimer's disease: A systematic review and meta-analysis. *Lancet Neurol.* 15, 673-684.

38. Diniz, B. S., Pinto Junior, J. A., and Forlenza, O. V. (2008) Do CSF total tau, phosphorylated tau, and beta-amyloid 42 help to predict progression of mild cognitive impairment to Alzheimer's disease? A systematic review and meta-analysis of the literature. *World J. Biol. Psychiatry* 9, 172-182.

39. Ferreira, L., Ferreira Santos-Galduroz, R., Ferri, C. P., and Fernandes Galduroz, J. C. (2014) Rate of cognitive decline in relation to sex after 60 years-of-age: A systematic review. *Geratr. Gerontol. Int.* 14, 23-31.

40. Ferreira, D., et al. (2014) Improving CSF biomarkers' performance for predicting progression from mild cognitive impairment to Alzheimer's disease by considering different confounding factors: A metaanalysis. *Front. Aging Neurosci.* 6, 287.

41. Van Rossum, I. A., Vos, S., Handels, R., and Visser, P. J. (2010) Biomarkers as predictors for conversion from mild cognitive impairment to Alzheimer-type dementia: Implications for trial design. *J. Alz. Dis.* 20, 881-891.

42. Ritchie, C., et al. (2014) Plasma and cerebrospinal fluid amyloid beta for the diagnosis of Alzheimer's disease dementia and other dementias in people with mild cognitive impairment (MCI). *Cochrane Database Syst. Rev.* 6, 8782.

43. Noel-Storr, A. H., et al. (2013) Systematic review of the body of evidence for the use of biomarkers in the diagnosis of dementia. *Alz. Dement.* 9, 96-105.

44. Hu, Y., Su, B., Zheng, H., and Kim, J. R. (2012) A peptide probe for detection of various beta-amyloid oligomers. *Mol. Biosyst.* 8, 2741-2752.

45. Sun, L., et al. (2018) A hydrogel biosensor for high selective and sensitive detection of amyloid-beta oligomers. *Int. J. of Nanomed.* 13, 843-856.

46. Laske, C., et al. (2015) Innovative diagnostic tools for early detection of Alzheimer's disease. *Alz. & Dement.* 11, 561-578.

47. Swati, S., et al. (2019) In vivo assessment of retinal biomarkers by hyperspectral imaging: Early detection of Alzheimer's disease. *ACS Chem. Neurosci.* 10, 4492-4501.

48. Forlenza, O. V., et al. (2015) Cerebrospinal fluid biomarkers in Alzheimer's disease: Diagnostic accuracy and prediction of dementia. Alz. & Dem.: Diagnosis, *Assessment & Dis. Monitoring* 1, 455-463.

49. Nabers, A., Hafermann, H., Wiltfang, J., and Gerwert, K. (2019) Abeta and tau structure-based biomarkers for a blood- and CSF-based two-step recruitment strategy to identify patients with dementia due to Alzheimer's disease. *Alz. & Dem.: Diagnosis, Assessment & Dis. Monitoring,* 11, 257-263.

50. Palmqvist, S., et al. (2020) Discriminative accuracy of plasma phospho-tau217 for Alzheimer disease vs other neurodegenerative disorders. *J. Am. Med. Assoc.* 324, 772-781.

51. Barthelemy, N. R, Horie, K., Sato, C., and Bateman, R. J. (2020) Blood plasma phosphortylated-tau isoforms track CNS change in Alzheimer's disease. *J. Exp. Med.* 217, 861.

52. Toledo, J. B., Xia, S. X., Trojanowski, J. Q., and Shaw, L. M. (2013) Longitudinal change in CSF Tau and Abeta biomarkers for up to 48 months in ADNI. *Acta Neuropathol.* 126, 659-670.

53. Buchhave, P., Minthon, L., Zetterberg, H., Wallin, A. K., Blennow, K., and Hansson, O. (2012) Cerebrospinal fluid levels of beta-amyloid 1-42, but not of tau, are fully changed already 5 to 10 years before the onset of Alzheimer dementia. *Arch. Gen. Pschiatry* 69, 98-106.

54. DeFelice, F. G., et al. (2008) Alzheimer's disease-type neuronal tau hyperphosphorylation induced by Abeta oligomers. *Neurobio. Aging,* 29, 1334-1347.

55. Amar, F., et al. (2017) Amyloid-beta oligomer A$\beta$*56 induces specific alterations of tau phosphorylation and neuronal signaling. *Sci. Signal.* 10, eaal2021.

56. Zempel, H., Thies, E., Mandelkow, E., and Mandelkow, E. M. (2010) Abeta oligomers cause localized Ca2+ elevation, missorting of endogenous tau into dendrites, tau phosphorylation, and destruction of microtubules and spines. *J. Neurosci.* 30, 11938-11950.

57. Thijssen, E. H. et al. (2020) Diagnostic value of plasma phosphorylated tau181 in Alzheimer's disease and frontotemporal lobar degeneration. *Nature Med.* 26, 387-397.

58. Janelidze, S., et al. (2020) Cerebrospinal fluid p-tau217 performs better than p-tau181 as a biomarker of Alzheimer's disease. *Nature Commun.* 11, 1683.

59. Musiek, E. S., and Holtzman, D. M. (2015) Three dimensions of the amyloid hypothesis: time, space and 'wingmen'. *Nature Neurosci.* 18, 800-806.

60. Busche, M. A., and Hyman, B. T. (2020) Synergy between amyloid-Ώ and tau in Alzheimer's disease. *Nature Neurosci.* 23, 1183-1193.

61. Miller, Y., Ma, B., and Nussinov, R. (2010) Polymorphism in Alzheimer Abeta amyloid organization reflects conformation selection in a rugged energy landscape. *Chem. Rev.* 110, 4820-4838.

62. Ono, K., Condron, M. M., and Teplow, D. B. (2009) Structure-neurotoxicity relationships of amyloid beta-protein oligomers. *Proc. Natl. Acad. Sci. USA,* 106, 14745-14750.

63. Lesne, S., Koh, M. T., Kotilinek, L., Kayed, R., Glabe, C. G., Yang, A., Gallagher, M. and Ashe, K. H. (2006) A specific amyloid-beta protein assembly in the brain impairs memory. *Nature* 440, 352-357.

64. Townsend, M., Shankar, G. M., Mehta, T., Walsh, D. M., and Selkoe, D. J. (2006) Effects of secreted oligomers of amyloid beta-protein on hippocampal synaptic plasticity: A potent role for trimers. *J. Physiol.* 572, 477-492.

65. Shankar, G. M., et al. (2008) Amyloid-beta protein dimers isolated directly from Alzheimer's brains impair synaptic plasticity and memory. *Nat. Med.* 14, 837-842.

66. Quist, A., et al. (2005) Amyloid ion channels: A common structural link for protein-misfolding disease. *Proc. Natl. Acad. Sci. USA* 102, 10427-10432.

67. Walsh, D. M., et al. (2002) Naturally secreted oligomers of amyloid beta protein potently inhibit hippocampal long-term potentiation in vivo. *Nature* 416, 535-539.
68. Wang, H. W., et al. (2002) Soluble oligomers of beta amyloid (1-42) inhibit long-term potentiation but not long-term depression in rat dentate gyrus. *Brain Res.* 924, 133-140.
69. Ehrnhoefer, D. E., et al. (2008) EGCG redirects amyloidogenic polypeptides into unstructured, off-pathway oligomers. *Nat. Struct. Mol. Biol.* 15, 558-566.
70. Ladiwala, R. A., Dordick, J. S., and Tessier, P. M. (2011) Aromatic small molecules remodel toxic soluble oligomers of amyloid beta through three independent pathways. *J. Biol. Chem.* 286, 3209-3218.
71. Glabe, C. G. (2008) Structural classification of toxic amyloid oligomers. *J. Biol. Chem.* 283, 29639-29643.
72. Roychaudhuri, R., Yang, M., Hoshi, M. M., and Teplow, D. B. (2009) Amyloid beta-protein assembly and Alzheimer disease. *J. Biol. Chem.* 284, 4749-4753.
73. Pujol-Pina, R., et al. (2015) SDS-PAGE analysis of Aβ oligomers is disserving research into Alzheimer's disease: Appealing for ESI-IM-MS. *Sci. Rep.* 5, 14809.
74. Kinoshita, A., Fukumoto, H., Shah, T., Whelan, C. M., Irizarry, M. C., and Hyman, B. T. (2003) Demonstration by FRET of BACE interaction with the amyloid precursor protein at the cell surface and in early endosomes. *J. Cell Sci.* 116, 3339-3346.
75. De Strooper, B. (2010) Proteases and proteolysis in Alzheimer disease: a multifactorial view on the disease process. *Physiol. Rev.* 90, 465-494.
76. Kumar, S., et al. (2011) Extracellular phosphorylation of the amyloid beta-peptide promotes formation of toxic aggregates during the pathogenesis of Alzheimer's disease. *EMBO J.* 30, 2255-2265.
77. Jarrett, J. T., Berger, E. P., and Lansbury, P. T. (1993) The carboxy terminus of the beta amyloid protein is critical for the seeding of amyloid formation: Implications for the pathogenesis of Alzheimer's disease. *Biochemistry* 32, 4693-4697.
78. Portelius, E., et al. (2010) Distinct cerebrospinal fluid amyloid beta peptide signatures in sporadic and PSEN1 A431E-associated familial Alzheimer's disease. *Mol. Neurodegener.* 5, 2.
79. Lee, J., Culyba, E. K., Powers, E. T., and Kelly, J. W. (2011) Amyloid-beta forms fibrils by nucleated conformational conversion of oligomers. *Nat. Chem. Biol.* 7, 602-609.
80. Bernstein, S. L., et al. (2009) Amyloid-beta protein oligomerization and the importance of tetramers and dodecamers in the aetiology of Alzheimer's disease. *Nat. Chem.* 1, 326-331.
81. Economou, N. J., et al. (2016) Amyloid beta-protein assembly and Alzheimer's disease: Dodecamers of Aβ42, but not of Aβ40, seed fibril formation. *J. Am. Chem. Soc* 138, 1772-1775.
82. Kayed R, et al. (2003) Common structure of soluble amyloid oligomers implies common mechanism of pathogenesis. Science 300:486-489.
83. Tycko R (2004) Progress towards a molecular-level structural understanding of amyloid fibrils. Curr Opin Struct Biol 14:96-103.
84. Kirschner D A, Abraham C, Selkoe D J (1986) X-ray diffraction from intraneuronal paired helical filaments and extraneuronal amyloid fibers in Alzheimer disease indicates cross-β conformation. Proc Natl Acad Sci USA 83:503-507.
85. Lührs T, et al. (2005) 3D structure of Alzheimer's amyloid-β (1-42) fibrils. Proc Natl Acad Sci USA 102: 17342-17347.
86. Balbach J J, et al. (2002) Supramolecular structure in full-length Alzheimer's β-amyloid fibrils: Evidence for a parallel β-sheet organization from solid-state nuclear magnetic resonance. Biophys J 83:1205-1216.
87. Armen R S, DeMarco M L, Alonso D O, Daggett V (2004) Pauling and Corey's α-pleated sheet structure may define the prefibrillar amyloidogenic intermediate in amyloid disease. Proc Natl Acad Sci USA 101:11622-11627.
88. Armen R S, Alonso D O, Daggett V (2004) Anatomy of an amyloidogenic intermediate: Conversion of β-sheet to α-sheet structure in transthyretin at acidic pH. Structure 12: 1847-1863.
89. Daggett V (2006) α-sheet: The toxic conformer in amyloid diseases? Acc Chem Res 39: 594-602.
90. Maris N L, Shea D, Bleem A, Bryers J D, Daggett V (2018) Chemical and physical variability in structural isomers of an L/D α-sheet peptide designed to inhibit amyloidogenesis. Biochemistry 57:507-510.
91. Shea, D. et al. (2019) α-sheet secondary structure in amyloid b-peptide drives aggregation and toxicity in Alzheimer's disease. Proc Natl Acad Sci USA 116:8895-8900.

Example 2. AP Surface Coatings Inhibit Fibril Formation on Materials

Abstract

Biofilms remain a major threat to medical device viability, as these surface-associated bacteria can lead to implant rejection and recalcitrant infections. Engineered coatings for medical device materials must therefore employ chemistries that specifically target aspects of biofilm virulence. In this study, we demonstrate the preventative, anti-infective properties synthetic α-sheet peptides by grafting them to the surface of medically relevant materials. Polydopamine (PDA) coating served as a convenient conjugation strategy to display peptides on a variety of substrates, and the anti-fouling properties of the functional biomaterials were demonstrated using uropathogenic E. coli biofilms as a test organism.

Introduction

The development of modern medical technologies, such as anesthesia and antibiotic therapy, combined with specialized materials manufacturing, has enabled treatment of a wide variety of diseases and disorders via surgery. Unfortunately, the increase in invasive procedures in recent decades has been accompanied by a corresponding increase in healthcare associated infections, and the majority of these infections can be traced to biofilm formation on or in the surgical site.

Mature biofilm architectures result from the physico-chemical contributions of each of the three materials that comprise the extracellular matrix: hydrated polysaccharides, extracellular DNA, and proteins. A specific subset of matrix proteins, functional amyloid fibrils, are highly conserved among a variety of pathogens and serve as a structural scaffold within this complex biological material.

Figure 7:
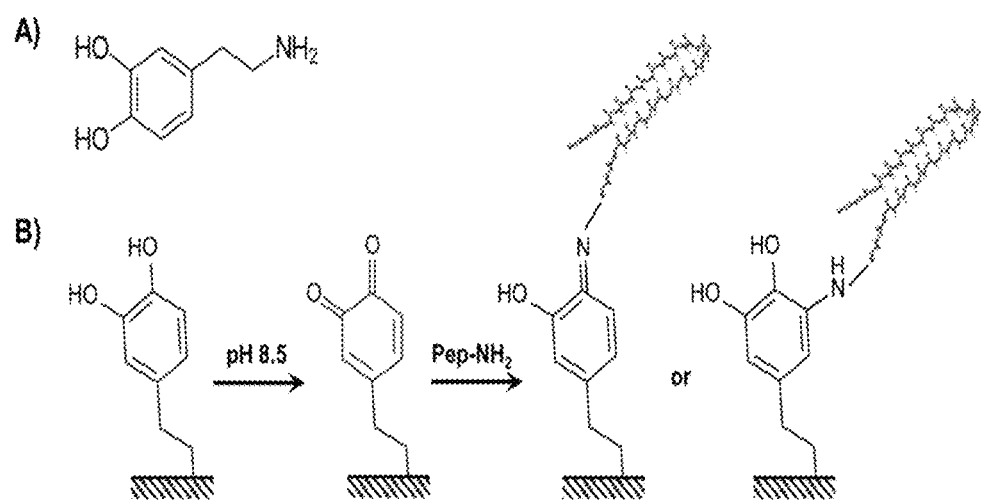
FIG. 7. Synthetic α-sheet peptides bind covalently to PDA-coated surfaces. (A) Dopamine displays both DOPA and lysine functional groups. (B) Reaction scheme to construct PGAPs. At slightly alkaline pH, dopamine undergoes self-polymerization to produce an adherent polydopamine (PDA) coating, accompanied by oxidation of the catechol groups to the quinone form. Synthetic α-sheet peptides contain amino groups (Pep-NH$_2$), which undergo Michael addition or Michael addition/Schiff base reaction to bind covalently to the PDA surface.

Dopamine (7A) polymerizes to form thin, uniform coatings of PDA on a wide variety of substrates. Once PDA is deposited on a surface, it displays multiple oxidized quinone forms of its catechol moiety, which can then undergo reactions with amines or thiols to form covalently grafted functional layers (FIG. 7B). Furthermore, PDA itself presents a hydrophilic, non-fouling surface that can impart wettability on even very hydrophobic materials.

In this study, PDA-grafted α-sheet peptides (PGAPs) are presented as a novel anti-biofilm approach that can be applied to a variety of surfaces. Through a simple and effective process, synthetic α-sheet peptides were linked to organic and inorganic material substrates, where they prohibited attachment of uropathogenic *E. coli* in multiple culture models by interfering with curli assembly in the biofilm matrix. PGAP materials also possess desirable qualities for medical implants: they are non-toxic to mammalian cells, and they maintain activity over time. To our knowledge, this is the first demonstration of anti-amyloid activity in a material coating, and the results presented here establish the utility of α-sheet peptides in preventing biofilm formation on a variety of material surfaces.

Results

PDA Enables Covalent Linkage of Synthetic α-sheet Peptides to Surfaces

Biofilms form on virtually every type of medical device implant, and several medically relevant materials itanium ($TiO_2$), an inorganic material used for orthopedic implants; polypropylene (PP), an organic material often used in synthetic sutures; and silicone, most commonly used in catheters, in addition to polyurethane and glass. Deposition of PDA occurs spontaneously in aqueous solutions at alkaline pH[33]. Submersion of clean substrates in a solution of dopamine HCl (2 mg/mL in 50 mM Tris, pH 8.5) for 24 h with shaking at 300 rpm was sufficient to fully coat the surface in a thin film of PDA. For peptide grafting, 125 μM synthetic α-sheet peptide solution (AP90 or AP193; P1 and BSA served as controls) was applied to PDA-coated substrates for 4 h at 25° C. and then moved to 4° C. overnight, for ~18 h total reaction time. Peptide solutions were removed and fully formed PGAPs (FIG. 7B) were rinsed thoroughly with sterile water prior to use.

Figure 8:
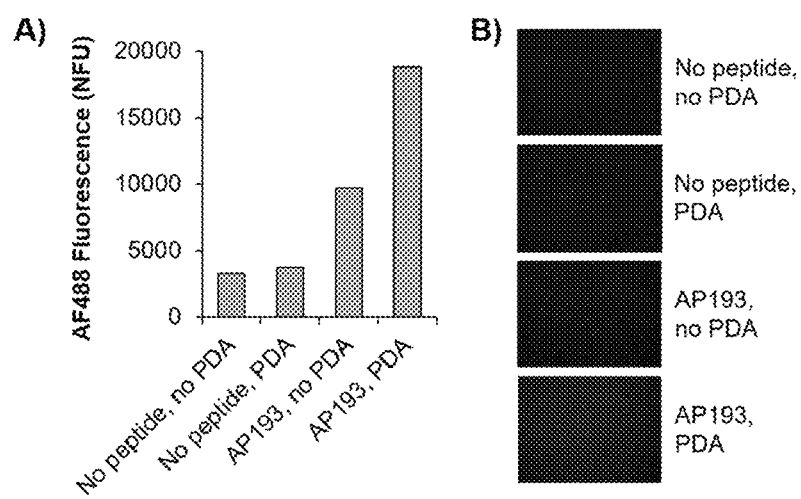
FIG. 8. PDA enhances attachment of dimeric AP193 to polypropylene substrates. Polypropylene microtiter plates were prepared according to the PGAP assembly protocol and then probed with Pac53 polyclonal antibody, which recognizes a portion of the AP193d sequence. Pac53 was conjugated to AlexaFluor® 488 (AF488), which enabled evaluation of AP193d binding by (A) fluorescence measurements and (B) fluorescence microscopy (200× magnification). Note that there is little coupling of monomeric AP193, as shown below in FIG. 13.

Successful grafting of peptides to the PDA surface was verified by two methods. First, a colorimetric assay (BCA assay; Thermo Fisher) estimated coupling efficiency and surface density. 96 well PP microtiter plates were coated with PDA and incubated with peptide as above, and then the concentration of peptide in solution after grafting was compared to the applied concentration to determine coupling efficiency. AP193 demonstrated higher coupling efficiency (68%) than AP90 at the same concentration (46%), possibly due to the presence of more hydrophobic side chains in the AP193 dimer sequence that promoted its physisorption to the surface. AP193d was therefore chosen as the α-sheet peptide for grafting in subsequent experiments. The surface coverage of AP193 after coupling was estimated as ~9 μmol/cm$^2$, based on the dimensions of the wells in the PP plate and the mass of peptide bound. Next, the accessibility of AP193 on PGAP surfaces (96 well PP plates) was determined by probing functionalized PGAPs with AlexaFluor®488-conjugated Pac53 antibody, which recognizes one strand of the AP193 hairpin. Immunofluorescence measurements in a plate reader and fluorescence microscopy revealed ample peptide attachment to the surface (FIG. 8A, B). Though AP193 exhibited some nonspecific adsorption to PP surfaces even in the absence of PDA, pre-coating with PDA substantially increased the amount of peptide bound (FIG. 8A). This was attributed to the fact that PDA enabled both nonspecific physical adsorption and specific covalent bonding between peptide amine groups and PDA quinones.

PGAP Materials Inhibit Bacterial Biofilm Formation

Figure 9:
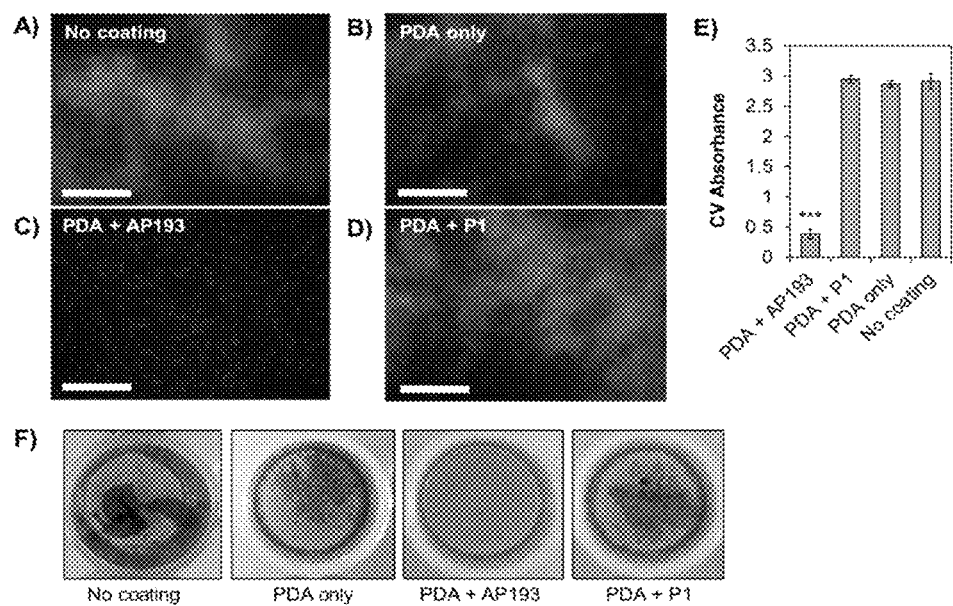
FIG. 9. PDA-grafted α-sheet peptides prevent formation of E. coli biofilms on polypropylene substrates. Polypropylene PDA-grafted α-sheet peptides (96 well microtiter plates) were inoculated with E. coli UTI89 SLC-719 and incubated for 48 h at 26° C. The resulting biofilms were visualized by (A-D) fluorescence microscopy and (α-F) Crystal Violet staining. Scale bars in (A-D) denote 60 m and error bars in (E) represent the standard deviation from the mean of three samples. ***$p<0.001$, two-tailed Student's t-test.
Figure 10:
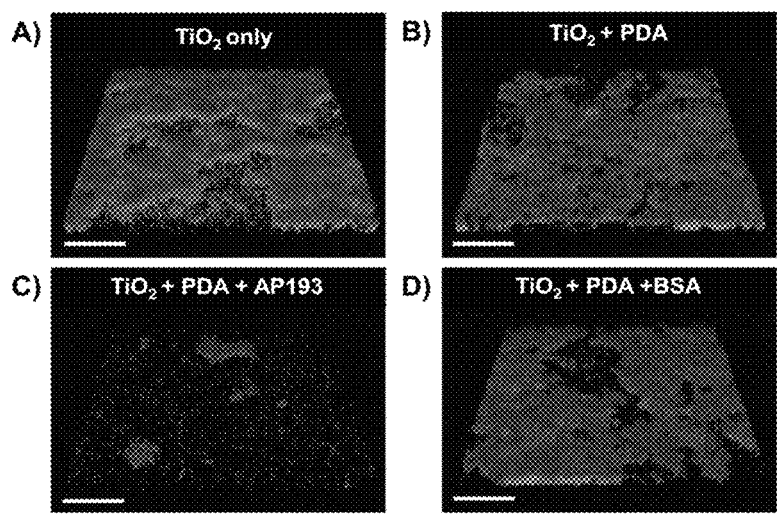
FIG. 10. PDA-grafted α-sheet peptides prevent formation of E. coli biofilms on titanium substrates. Titanium disks were functionalized with PDA and AP193d, inoculated with E. coli UTI89 SLC-719 and incubated for 48 h at 26° C. The surfaces were gently washed and imaged by confocal microscopy. Coatings with (C) AP193d caused substantial biofilm disruption compared to (A-B), (D) controls. Scale bars denote 55 m.

Good attachment and availability of PGAPs on PP surfaces did not necessarily ensure activity of the grafted peptides, so further tests were carried out to determine whether PGAPs could inhibit biofilm formation in a manner similar to synthetic α-sheet peptides in suspension. UPEC biofilms were cultivated on PGAP surfaces for 48 h under conditions known to illicit robust amyloid production in the EM (26° C., YESCA broth+4% DMSO), and then the degree of biofilm adherence was evaluated by several methods. First, fluorescent *E. coli* UTI89 (strain SLC-719)[41] were cultivated in 96 well PP plates functionalized with PDA/AP193, PDA/P1, PDA alone, or no coating, and the resulting biofilms were evaluated with fluorescence microscopy and crystal violet (CV) staining. As shown in FIG. 9A-D, AP193 PGAPs substantially reduced the fouling of PP surfaces, with very few bacteria adhered to the plate compared to PDA alone or PDA functionalized with the random coil control peptide, P1. These observations were confirmed by CV staining, which demonstrated significantly less biofilm adherence when AP193 was present in the functional coating (FIG. 9E) and very little fouling visible to the naked eye (FIG. 9F). Confocal microscopy revealed similar characteristics for PGAPs displayed on $TiO_2$; these materials also exhibited decreased biofilm coverage compared to PDA alone, PDA functionalized with BSA, or uncoated $TiO_2$ (FIG. 10).

Figure 11:
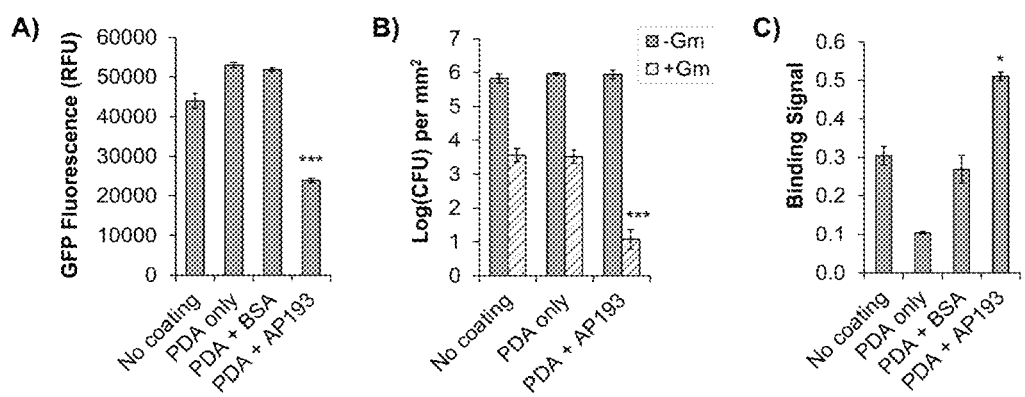
FIG. 11. Characterization of silicone PDA-grafted α-sheet peptides. A) Silicone pieces were functionalized with PGAPs (AP193d), inoculated with E. coli UTI89 SLC-719 and incubated for 48 h at 26° C. After a rinse step, pieces were ultrasonicated to remove adherent biofilms, and then the GFP fluorescence of biofilm suspensions was measured in a plate reader (A). Coatings with AP193d resulted in a significant decrease in the amount of adhered biofilm (*$p<0.0005$). (B) Colony forming unit (CFU) counts were determined for silicone-associated biofilms with (hashed bars) and without (solid bars) 300 μg/mL Gm challenge. The presence of AP193d on the surface resulted in approximately 100-fold fewer viable bacteria after Gm challenge compared to peptide-free controls. (*$p<0.0003$). (C) Spent silicone pieces were probed with Pac53 antibody in an ELISA-like assay. These materials still displayed accessible—and presumably, active-AP193d on the surface (*$p<0.02$). All p values were generated by a two-tailed Student's t-test for significance, and error bars indicate the standard deviation from the mean.

Healthcare-associated *E. coli* infections typically manifest in the urinary tract, which involves biofilm formation on the surface of silicone catheters. Therefore, silicone tubing was implemented as a clinically relevant substrate for evaluation of the PGAP approach and its effect on biofilm development. PDA-coated silicone pieces were submerged in cultures of fluorescent *E. coli* UTI89 SLC-719 for 48 h (curli inducing conditions as described above), which encased the silicone in a biofilm. Each piece was then carefully rinsed to remove loosely attached cells, transferred to a tube of sterile PBS, and sonicated for 1 min to fully detach the adhered biofilm. Fluorescence measurements in a plate reader determined the bacterial density of each biofilm suspension, and biofilms formed on AP193 PGAP silicone were significantly less dense than those on PDA controls or silicone alone (FIG. 11A). Furthermore, PGAP silicone materials increased biofilms' susceptibility to antibiotics. In this case, the same culture conditions were used as in the bacterial density assay, but Gm (300 μg/mL) was added to half of the samples 6 h before the end of incubation. Antibiotic killing of bacteria increased significantly when biofilms were grown on PGAP silicone as opposed to silicone with PDA alone or no coating (FIG. 11B).

As a test of long-term functionality, PGAP silicone was probed by immunoassay to determine the accessibility of AP193 after a biofilm had already developed on the material surface. PGAP silicone pieces from the biofilm density assay (FIG. 11A) were virtually free of adhered bacteria after the ultrasonication step, but pieces were vortexed for an additional 30 s in fresh PBS to ensure complete detachment. These "spent" materials were then transferred to microcentrifuge tubes, where they were probed with Pac53 primary antibody and anti-IgG-TRP secondary antibody in an ELISA-like manner. Absorbance measurements of the quenched reaction solutions revealed significant AP193 remaining on the surface in PGAP materials compared to controls (FIG. 11C). The retention of accessible—and presumably, active—α-sheet peptides on the PGAP surface even after the development and removal of a mature biofilm indicates the potential for long-term viability of these materials.

Figure 12:
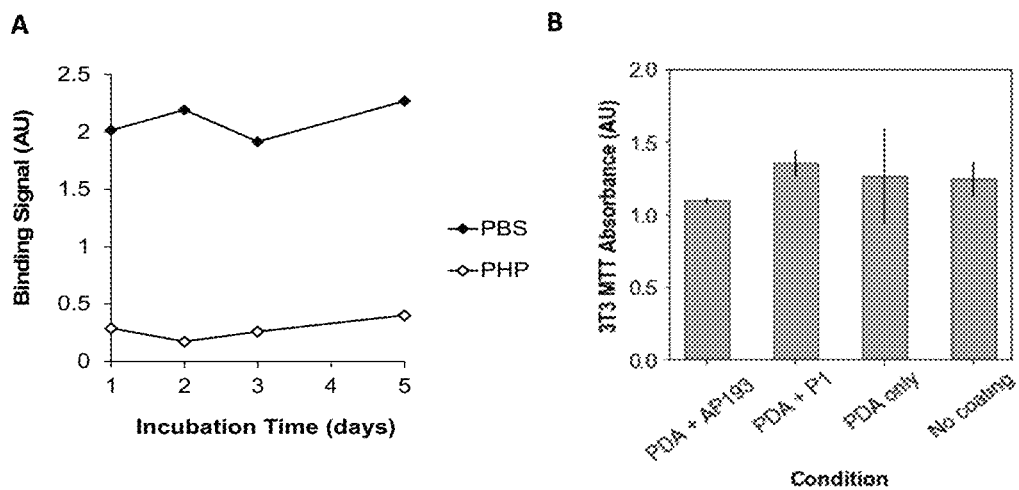
FIG. 12. PDA-grafted α-sheet peptide coatings retain functionality over time and do not affect cell viability. (A) Polypropylene plates with AP193 were incubated in PBS (black diamonds) or pooled human plasma (white diamonds) at 37° C. for up to 5 days, and the presence of α-sheet peptide on the surface was quantified by probing with Pac53. (B) Mouse 3T3 fibroblasts were grown on 96 well polystyrene tissue culture plates with the indicated coatings for 24 h, and then cell viability was determined by MTT assay. Absorbance readings indicated no significant difference between samples. Error bars indicate standard deviation from the mean of three replicates.

To further assess the stability of AP193 in PGAP materials, several wells of a PP plate were prepared with PDA and peptide, and then the materials were incubated in either saline (PBS) or pooled human plasma (PUP; 50% v/v in PBS) solution at 37° C. Solutions were withdrawn and replaced every 24 h up to five days, and wells were probed with the Pac53 antibody at the end of incubation to quantify the amount of accessible α-sheet peptide on the surface. Binding signals between AP193 and Pac53 did not decrease over time, regardless of whether the PGAP material was incubated in PBS or PHP (FIG. 12A). The magnitude of the binding signal was substantially lower for PGAPs incubated in PUP compared to PBS, suggesting nonspecific shielding of surface-bound AP193 by proteins in the plasma solution. Nevertheless, α-sheet peptides on the surface of PGAPs continued to display functional binding moieties throughout the course of incubation, indicating their potential for long-term use as implant materials. Indeed, even after incubation of PGAPs for five months in PBS at 4° C., AP193 was easily detectable by Pac53. Finally, the colorimetric MTT (3-(4,5-dimethylthiazol-2-yl)-2,5-diphenyltetrazolium bromide) cell viability assay was applied to determine the compatibility of PGAPs with mouse embryonic fibroblast (3T3) cells. Polystyrene tissue culture plates were coated with PDA as previously and then AP193 and P1 were grafted to the surface. 3T3 cells were applied at a fixed dilution to each prepared well in triplicate and allowed to proliferate for 24 h at 37° C. prior to application of MTT, cell lysis, and colorimetric measurement. PGAP coatings did not significantly affect the viability of 3T3 cells compared to controls (FIG. 12B), indicating good compatibility between the functional materials and potential patient hosts.

Discussion

The results presented here demonstrate the efficacy of grafted synthetic α-sheet peptides on medical materials indicating their adaptability to a variety of surface chemistries, including silicone catheters, titanium implants, and polypropylene devices. PGAP materials depleted the curli content in the matrix of uropathogenic E. coli biofilms, leading to a strong anti-fouling effect. Biofilms grown on PGAP surfaces showed poor adhesion and soluble phenotypes, and the PDA coating approach afforded anti-amyloid functionality with specificity for the material surface. In addition to their potency, PGAP coatings show potential for multiple improvements over dispersed or systemic administration of synthetic α-sheet peptides. First, the covalent linkage of synthetic α-sheet peptides to PDA stabilizes the surface and prevents clearance of the functional molecule. Second, restriction of PGAP functionality specifically to the material surface reduces the amount of peptide required to achieve a therapeutic effect. Finally, prolonged stability of AP193 peptides following biofilm challenge on silicone PGAPs indicate that these materials will maintain functionality long after their initial implantation.

Materials and Methods

Generation of PGAPs

Before coating with PDA, all materials were cleaned thoroughly according to previously established protocols[43]. Briefly, titanium disks (medical grade, 1" diameter; Sigma) were cleaned by sonication for 5 min each in acetone, ethanol, and water, and then rinsed thoroughly in distilled water. Silicone tubing was cut by scalpel into ~2 mm×2 mm pieces and then washed in 70% ethanol for 10 min. 96 well PP plates (Grenier Bio-one; Monroe, NC) were already sterile and not subjected to further cleaning. To initiate the coating process, 2 mg/mL dopamine HCl (Sigma) was dissolved in 10 mM Tris HCl, pH 8.5, and applied to substrates for 24 h with shaking at 300 rpm. For titanium and silicone, materials were submerged in a petri dish containing dopamine solution, while 96 well plates were coated by filling each well with 165 µL dopamine solution. Incubation lead to polymerization of dopamine, as evidenced by dark coloring of the solutions and deposition of a thin, brown PDA film on all surfaces. Substrates were then rinsed five times with distilled water, air dried, and dried to completion in a vacuum chamber at 30° C. for 1 h. Control substrates without PDA were also generated according to the same protocol but with incubation in Tris buffer instead of dopamine solution.

All peptides were synthesized and purified according to previously reported protocols[24], and lyophilized peptides were resuspended in appropriate buffer immediately before use. AP193 dimerization took place in solution using a previously established protocol[44]. Briefly, 0.25 mg of lyophilized AP193 monomer was dissolved in 4 µL DMSO and then diluted in ~300 µL 50 mM sodium carbonate buffer (pH 9.6) to bring the concentration of peptide to 250 µM (monomer concentration). AP193 peptide solution was incubated at 37° C. for 2 hours, which allowed complete oxidation of disulfide bonds as evidenced by a lack of absorption at 412 nm by Ellman's reagent (Thermo Fisher). AP90 does not contain disulfide bonds and was therefore resuspended to a concentration of 250 µM in 50 mM potassium phosphate, pH 8.5. Similarly, BSA was diluted from purified 2 mg/mL stock (Thermo Fisher) to 0.3 mg/mL in potassium phosphate buffer. Solutions of peptide (or BSA, where indicated) were applied to clean, PDA-coated substrates for 4 h at 25° C. and then continued to react overnight at 4° C. for approximately 18 h total reaction time. In the case of 96 well PP plates, 50 µL of peptide solution was aliquoted into each well to initiate coupling. For titanium disks, 20 µL spots of peptide solution were pipetted onto specific regions of the disk and incubation was carried out in a humidified chamber to prevent evaporation. Prepared silicone pieces were submerged in sterile 1.5 mL Eppendorf tubes with 80 µL peptide solution. Peptide solutions were removed, and substrates were washed three times with sterile water. Peptide concentrations (grafting and washes) were compared to the applied concentration using the Pierce BCA Protein Assay Kit (Thermo Fisher) using a simple metric for coupling efficiency:

$$E = 1 - \left(\frac{\text{concentration removed}}{\text{concentration applied}}\right). \quad (1)$$

Peptide Stability Assessment

An anti-AP193 polyclonal antibody (Pac53, from rabbit) was used to verify successful peptide grafting and to determine the stability of PGAPs. For grafting verification, PGAPs on 96 well PP plates were blocked with 3% w/v BSA in PBS-T (PBS+0.05% v/v Tween-20) for 1 h at room temperature with shaking, and then 100 µL Pac53 solution (1:10,000 in PBS-T+3% BSA) was applied for 1 h at room temperature with shaking. After three washes, a secondary antibody to rabbit IgG with an AlexaFluor™ 488 label (Abcam; Cambridge, UK) was applied for 45 min at room temperature with shaking prior to binding evaluation by fluorescence microscopy and plate reader measurement. For stability tests, PGAPs on 96 well PP plates were filled with 100 µL PBS or 100 µL pooled human plasma (50% in PBS; Sigma), covered, and incubated at 37° C. without shaking. Every 24 h, PBS and plasma were withdrawn and replaced, for a total of 5 days' incubation. A sandwich ELISA was performed with Pac53 and anti-rabbit IgG secondary antibody (Abcam) to estimate the amount of peptide released from the surface during incubation. Known AP193 concentrations (determined by NanoDrop™) served as standards in the same plate, and colorimetric quantification was performed using 1-Step Ultra™ TMB ELISA Substrate Solution (ThermoFisher) and 2 M $H_2SO_4$ quenching, followed by absorbance measurements in a plate reader (Perkin Elmer).

For "spent" PGAP silicone pieces, the same antibodies and reagents were used as above. Briefly, spent silicone pieces were vortexed for 30 s in fresh PBS to ensure complete bacterial detachment. They were then transferred to 1.5 mL microcentrifuge tubes, where they were blocked with 200 µL BSA solution overnight (3% w/v in PBS-T), probed 2 h at room temperature with 200 µL Pac53 polyclonal antibody (1:10,000 in PBS-T+3% w/v BSA), washed three times in 500 µL PBS-T with vortexing, probed 2 h at room temperature with 200 L secondary antibody to rabbit IgG (Santa Cruz Biotechnology), washed three times in 500 µL PBS-T with vortexing, and then developed for 2 h with 200 µL 1-Step Ultra™ TMB ELISA Substrate Solution (ThermoFisher). 50 µL of each sample was transferred in duplicate to a microtiter plate and reactions were quenched with 50 µL 2 M $H_2SO_4$ prior to absorbance measurements in a plate reader (PerkinElmer).

Biofilm Challenge Assays

E. coli UTI89 SLC-719 was prepared in YESCA broth+ 4% DMSO[45]. PP plates were inoculated with 120 µL per well of diluted culture, titanium disks were placed in petri dishes and submerged in 5 mL diluted culture, and silicone pieces were placed in wells of a 48 well polystyrene plate and submerged in 400 µL of diluted culture. All biofilms were grown without shaking for 48 h at 26° C. After growth, planktonic cells and media were removed and biofilms were rinsed once with PBS. PP plates were fixed with 4% paraformaldehyde and imaged on a Zeiss Axio™ Observer (Carl Zeiss AG) inverted fluorescent microscope, while $TiO_2$ disks were mounted on glass slides with an oiled coverslilp and imaged on a Zeiss LSM 510 confocal laser scanning microscope. For CV assays, 120 µL crystal violet stain solution was applied to each well for 1 h prior to removal, rinsing with PBS, and drying overnight. Dried, CV-stained biofilms were resuspended in 120 µL 30% acetic acid and absorbance measurements at 550 nm served as a crude measure of biofilm biomass. For silicone adherence assays, biofilm-covered silicone pieces were transferred to 1.5 Eppendorf tubes containing 300 µL of sterile PBS and ultrasonicated on ice for 1 min to detach adhered bacteria. Biofilm suspensions were then aliquoted into a black 96 well plate and fluorescence at 488 nm (GFP) served as an estimate of the number of adhered cells. For antibiotic challenge in the silicone adherence assays, biofilm-covered silicone pieces were transferred to wells containing fresh YESCA medium with or without 300 µg/mL Gm during the final 6 h of incubation. Pieces were then rinsed once in 200 µL sterile PBS to remove loosely adhered bacteria, media, and antibiotics, and then pieces were ultrasonicated as above to detach adhered bacteria. Biofilm suspensions were serially diluted in sterile PBS and enumerated on agar plates according to the drop plate method[46]. The number of colonies was back-calculated to determine the total number of bacteria on each silicone piece, and then these counts were normalized according to the surface area of the silicone piece ($CFU/mm^2$).

Cytotoxicity Assessment

Compatibility of PGAPs with mammalian cells was assessed with the colorimetric MTT assay. Mouse fibroblasts (NIH/3T3 cells; ATCC; Manassas, VA) were cultured in complete medium (DMEM+10% fetal bovine serum+1× penicillin/streptomycin) to 70% confluency and then cells were detached by trypsin and counted by hemacytometer. Meanwhile, sterile 96 well polystyrene tissue culture plates were coated with PDA and functionalized with AP193 or BSA as described above. After thorough washing of the prepared plate with sterile water, 150 µL of 3T3 suspension in fresh complete medium ($5×10^4$ cells/mL) was applied to each well, with at least three wells prepared per condition. Serial dilutions ranging from $1×10^6$ to $1×10^3$ cells/mL were also added in triplicate to the same plate to provide a standard curve and determine the linear range of the assay. After 24 h of growth at 37° C., 37.5 µL MTT solution (3-(4,5-dimethylthiazol-2-yl)-2,5-diphenyltetrazolium bromide; 5 mg/mL in PBS; Sigma) was added to each well and the plate was incubated a further 4 h. Cells were then lysed with a chaotropic buffer (20% SDS, 50% DMF, 1% acetic acid, 0.2% HCl) and incubated overnight to release intracellular oxidoreductase enzymes. These enzymes convert MTT from a yellow color to a dark purple color, which was measured by absorbance on a plate reader at 570 nm; higher absorbance indicated greater cell viability.

REFERENCES

1. Percival, S. L., Suleman, L., Vuotto, C. & Donelli, G. Healthcare-associated infections, medical devices and biofilms: risk, tolerance and control. *J. Med. Microbiol.* 64, 323-334 (2015).
2. Bryers, J. D. Medical Biofilms. *Biotechnol. Bioeng.* 100, 1-18 (2008).
3. Zeng, G., Ogaki, R. & Meyer, R. L. Non-proteinaceous bacterial adhesins challenge the antifouling properties of polymer brush coatings. *Acta Biomater.* 24, 64-73 (2015).
4. Falde, E. J., Yohe, S. T., Colson, Y. L. & Grinstaff, M. W. Superhydrophobic materials for biomedical applications. *Biomaterials* 104, 87-103 (2016).
5. May, R. M. et al. An engineered micropattern to reduce bacterial colonization, platelet adhesion and fibrin sheath formation for improved biocompatibility of central venous catheters. *Clin. Transl. Med.* 4, (2015).
6. Gilabert-Porres, J. et al. Design of a Nanostructured Active Surface against Gram-Positive and Gram-Negative Bacteria through Plasma Activation and in Situ Silver Reduction. *ACS Appl. Mater. Interfaces* 8, 64-73 (2016).
7. Koo, H., Allan, R. N., Howlin, R. P., Stoodley, P. & Hall-Stoodley, L. Targeting microbial biofilms: current and prospective therapeutic strategies. *Nat. Rev. Microbiol.* 15, 740-755 (2017).
8. Khatoon, Z., McTiernan, C. D., Suuronen, E. J., Mah, T.-F. & Alarcon, E. I. Bacterial biofilm formation on implantable devices and approaches to its treatment and prevention. *Heliyon* 4, e01067 (2018).
9. Campoccia, D., Montanaro, L., Speziale, P. & Arciola, C. R. Antibiotic-loaded biomaterials and the risks for the spread of antibiotic resistance following their prophylactic and therapeutic clinical use. *Biomaterials* 31, 6363-6377 (2010).
10. Gruenheid, S. & Moual, H. Resistance to antimicrobial peptides in Gram-negative bacteria. *FEMS Microbiol. Lett.* 330, 81-89 (2012).
11. Banerjee, I., Pangule, R. C. & Kane, R. S. Antifouling Coatings: Recent Developments in the Design of Surfaces 12. Qin, H. et al. In vitro and in vivo anti-biofilm effects of silver nanoparticles immobilized on titanium. *Biomaterials* 35, 9114-9125 (2014).

13. Forier, K. et al. Lipid and polymer nanoparticles for drug delivery to bacterial biofilms. *J. Controlled Release* 190, 607-623 (2014).

14. Silver, S., Phung, L. T. & Silver, G. Silver as biocides in burn and wound dressings and bacterial resistance to silver compounds. *J. Ind. Microbiol. Biotechnol.* 33, 627-634 (2006).

15. Flores-Mireles, A. L., Pinkner, J. S., Caparon, M. G. & Hultgren, S. J. EbpA vaccine antibodies block binding of *Enterococcus faecalis* to fibrinogen to prevent catheter-associated bladder infection in mice. *Sci. Transl. Med* 6, 254ra127-254ra127 (2014).

16. Lu, T. K. & Collins, J. J. Dispersing biofilms with engineered enzymatic bacteriophage. *Proc. Natl. Acad Sci.* 104, 11197-11202 (2007).

17. Taglialegna, A., Lasa, I. & Valle, J. Amyloid Structures as Biofilm Matrix Scaffolds. *J. Bacteriol.* 198, 2579-2588 (2016).

18. Bleem, A. & Daggett, V. Structural and functional diversity among amyloid proteins: Agents of disease, building blocks of biology, and implications for molecular engineering. *Biotechnol. Bioeng.* 114, 7-20 (2017).

19. DePas, W. H. & Chapman, M. R. Microbial manipulation of the amyloid fold. *Res. Microbiol.* 163, 592-606 (2012).

20. Armen, R. S., Bernard, B. M., Day, R., Alonso, D. O. V. & Daggett, V. Characterization of a possible amyloidogenic precursor in glutamine-repeat neurodegenerative diseases. *Proc. Natl. Acad Sci. U.S.A.* 102, 13433-13438 (2005).

21. Armen, R. S., DeMarco, M. L., Alonso, D. O. V. & Daggett, V. Pauling and Corey's α-pleated sheet structure may define the prefibrillar amyloidogenic intermediate in amyloid disease. *Proc. Natl. Acad. Sci.* 101, 11622-11627 (2004).

22. Armen, R. S., Alonso, D. O. V. & Daggett, V. Anatomy of an Amyloidogenic Intermediate: Conversion of β-Sheet to α-Sheet Structure in Transthyretin at Acidic pH. *Structure* 12, 1847-1863 (2004).

23. Steward, R. E., Armen, R. S. & Daggett, V. Different disease-causing mutations in transthyretin trigger the same conformational conversion. *Protein Eng. Des. Sel.* 21, 187-195 (2008).

24. Hopping, G. et al. Designed α-sheet peptides inhibit amyloid formation by targeting toxic oligomers. *eLife* 3, e01681 (2014).

25. Shea, D. et al. α-Sheet secondary structure in amyloid β-peptide drives aggregation and toxicity in Alzheimer's disease. *Proc. Natl. Acad. Sci.* 201820585 (2019). doi:10.1073/pnas.1820585116

26. Bleem, A., Francisco, R., Bryers, J. D. & Daggett, V. Designed α-sheet peptides suppress amyloid formation in *Staphylococcus aureus* biofilms. *Npj Biofilms Microbiomes* 3, (2017).

27. Paranjapye, N. & Daggett, V. De Novo Designed α-Sheet Peptides Inhibit Functional Amyloid Formation of *Streptococcus mutans* Biofilms. *J. Mol. Biol.* 430, 3764-3773 (2018).

28. Kellock, J., Hopping, G., Caughey, B. & Daggett, V. Peptides Composed of Alternating L- and D-Amino Acids Inhibit Amyloidogenesis in Three Distinct Amyloid Systems Independent of Sequence. *J. Mol. Biol.* 428, 2317-2328 (2016).

29. Sato, A. K., Viswanathan, M., Kent, R. B. & Wood, C. R. Therapeutic peptides: technological advances driving peptides into development. *Curr. Opin. Biotechnol.* 17, 638-642 (2006).

30. Mcgregor, D. Discovering and improving novel peptide therapeutics. *Curr. Opin. Pharmacol.* 8, 616-619 (2008).

31. Goddard, J. M. & Hotchkiss, J. H. Polymer surface modification for the attachment of bioactive compounds. *Prog. Polym. Sci.* 32, 698-725 (2007).

32. Waite, J. H. & Qin, X. Polyphosphoprotein from the Adhesive Pads of *Mytilus edulis*†. *Biochemistry* 40, 2887-2893 (2001).

33. Lee, H., Dellatore, S. M., Miller, W. M. & Messersmith, P. B. Mussel-Inspired Surface Chemistry for Multifunctional Coatings. *Science* 318, 426-430 (2007).

34. Orishchin, N. et al. Rapid Deposition of Uniform Polydopamine Coatings on Nanoparticle Surfaces with Controllable Thickness. *Langmuir* 33, 6046-6053 (2017).

35. Kang, S. M. et al. One-Step Modification of Superhydrophobic Surfaces by a Mussel-Inspired Polymer Coating. *Angew. Chem. Int. Ed.* 49, 9401-9404 (2010).

36. Ding, Y. H., Floren, M. & Tan, W. Mussel-inspired polydopamine for biosurface functionalization. *Biosurface Biotribology* 2, 121-136 (2016).

37. Lee, Y. B. et al. Polydopamine-mediated immobilization of multiple bioactive molecules for the development of functional vascular graft materials. *Biomaterials* 33, 8343-8352 (2012).

38. Xu, L. Q., Yang, W. J., Neoh, K.-G., Kang, E.-T. & Fu, G. D. Dopamine-Induced Reduction and Functionalization of Graphene Oxide Nanosheets. *Macromolecules* 43, 8336-8339 (2010).

39. Lim, K. et al. Development of a catheter functionalized by a polydopamine peptide coating with antimicrobial and antibiofilm properties. *Acta Biomater.* 15, 127-138 (2015).

40. Yang, K. et al. Polydopamine-mediated surface modification of scaffold materials for human neural stem cell engineering. *Biomaterials* 33, 6952-6964 (2012).

41. Eshaghi, M., Mehershahi, K. & Chen, S. Brighter Fluorescent Derivatives of UTI89 Utilizing a Monomeric vGFP. *Pathogens* 5, 3 (2016).

42. Asker, D., Awad, T. S., Baker, P., Howell, P. L. & Hatton, B. D. Non-eluting, surface-bound enzymes disrupt surface attachment of bacteria by continuous biofilm polysaccharide degradation. *Biomaterials* 167, 168-176 (2018).

43. Jiang, L. et al. Surface characteristics of mussel-inspired polydopamine coating on titanium substrates. *J. Wuhan Univ. Technol.-Mater Sci Ed* 29, 197-200 (2014).

44. Tam, J. P., Wu, C. R., Liu, W. & Zhang, J. W. Disulfide bond formation in peptides by dimethyl sulfoxide. Scope and applications. *J. Am. Chem. Soc.* 113, 6657-6662 (1991).

45. Lim, J. Y., May, J. M. & Cegelski, L. Dimethyl sulfoxide and ethanol elicit increased amyloid biogenesis and amyloid-integrated biofilm formation in *Escherichia coli*. *Appl. Environ. Microbiol.* 78, 3369-3378 (2012).

46. Herigstad, B., Hamilton, M. & Heersink, J. How to optimize the drop plate method for enumerating bacteria. *J. Microbiol. Methods* 44, 121-129 (2001).

Example 3. SOBA: A Soluble Oligomer Binding Assay Targeting a Biomarker Linked to Early Molecular Pathophysiology Introduction Alzheimer's disease (AD) is one of over 50 amyloid diseases and is now the sixth leading cause of death in the United States, affecting over 5.8 million Americans and projected to cost upwards of $1.1 trillion in paid and unpaid care by 2050. AD is characterized by the aggregation of the amyloid beta (AD) peptide into a heterogeneous and dynamic distribution of low molecular weight (LMW) oligomers that progress into high molecular weight (HMW), beta-sheet rich protofibrils, eventually resulting in the formation of the characteristic cross-β pleated sheet fibrils that coat neurons and are the pathological hallmarks for amyloid diseases. Recent studies suggest that the LMW soluble oligomers are the main toxic agents in AD and that are strongly correlated with disease progression, while plaque burden is not. Interestingly, disease symptoms do not begin to present until the late stages of Ab aggregation when plaques have already deposited and the primary damage to the neurons has taken place. Current tests are only capable of diagnosing AD in the late stages of disease when protofibrils and fibrils dominate, which is too late to intervene and effectively treat the disease. In fact, several drug candidates targeting late-stage Abeta aggregates have not been successful in large, multicenter clinical trials. In the case of an early diagnosis scenario in the mild cognitive impairment (MCI) stage, upwards of $7.9 trillion could be saved in medical and long-term care alone.

We focus on the earliest structural changes that take place in a variety of amyloid systems involving the alpha-sheet secondary structure, which we believe is the key component involved in the aggregation and toxicity of the LMW oligomers in the early stages of disease. By focusing on the early misfolding that take place at a molecular level, we designed stable alpha-sheet peptides that inhibit aggregation, mitigate toxicity, capture toxic oligomers in vivo, and act as diagnostic agents that detect the alpha-sheet-containing toxic species pre-symptomatically in AD patients. Our diagnostic test is termed the Soluble Oligomer Binding Assay (SOBA), which is an ELISA-like assay wherein an alpha-sheet peptide is covalently linked to the plate and used as the capture agent rather than an antibody. We describe a novel technique that uses polydopamine (PDA) deposition to functionalize a 96-well polystyrene plate for peptide linkage for use in presymptomatic and symptomatic AD diagnosis. Additionally, we describe an alpha-sheet-based PET tracer for secondary diagnostic verification which could be used as a measure of improvement in the case of a future therapeutic intervention.

Results

SOBA is an ELISA-like assay that measures alpha-sheet content in both synthetic Abeta preparations as well as animal or patient-derived samples using a standard sandwich ELISA protocol with an alpha-sheet peptide used as the capture agent. In this regard, SOBA is a direct reporter of alpha-sheet structure in applied samples by binding to the toxic species through complementarity. Using PDA as a surface coating molecule to covalently link the alpha-sheet peptide to the plate—in place of the proprietary linking mechanism of the Nunc Immobilizer™ Amino plate—increased the uptake rate of alpha-sheet peptide from 21 mg/ml to 196 mg/ml total peptide bound (FIG. 13A). The increased density of the capture peptide resulted in improved sensitivity from 10 nM to 1 nM (FIG. 13B,C). Using chemiluminescence instead of TMB colorimetric detection in the absence of the PDA coating decreased the detection from 10 nM to 100 fM (FIG. 13D). Combining the PDA coating and the chemiluminescence, led to a further decrease to 1 fM—100 aM detection (FIG. 13E,F). Thus, the addition of the PDA coating with covalent attachment of dimeric alpha-sheet capture peptides and chemiluminescent development greatly surpassed the sensitivity of previous methods, with the lowest limit of detection at blank. Importantly, the specificity is maintained throughout all protocols as monomeric and protofibrillar forms of Abeta42 applied at 100 μM resulted in essentially a null signal on par with background (<10,000 SOBA signal is below the limit of detection signal cutoff of 21,943) compared with the toxic oligomer applied at 100 μM resulting in a SOBA signal of ~700,000 (FIG. 13E).

After establishing the performance of the SOBA assay using dimeric AP capture agents covalently linked to the plate via a polymer coating to increase display of the capture agents in CSF, plasma and PBS spiked with Abeta42 toxic oligomers (results in FIG. 13 are spiked plasma), patient samples were tested. In particular, the levels of the toxic oligomers are very low in blood, and they cannot be detected without the combination of the PDA coating and the dimeric capture agents.

We tested 379 cross-sectional and longitudinal human plasma samples from 310 individuals classified based on a comprehensive clinical evaluation: noncognitively impaired controls (CO, n=221), mild cognitive impairment AD-type (MCI, n=45), and moderate to severe AD (n=102), and Other non-AD cognitive impairment (non-AD CI, n=11). Of the CO cases, 11 were 'converters' who progressed to MCI: 8 to MCI (AD-type) (n=10, including 2 longitudinal samples) and 3 to non-AD CI in follow-up clinical visits. The 379 samples were considered independent for aggregate analyses.

The CO, MCI and AD groups had similar mean ages and nearly equal distribution by sex. There was a bimodal distribution of SOBA values in the CO group: (1) negative CO cases and (2) individuals with significant SOBA scores who later converted to MCI, which we refer to as preclinical AD, or PC-AD (FIG. 14A). SOBA provided good discrimination between the CO and MCI and AD participants, with a cutoff value of 28,207, as determined through a Receiver Operator Characteristic analysis. Values above this cutoff were considered SOBA positive and values below, SOBA negative (FIG. 14A). This cutoff discriminating SOBA positive and negative samples corresponded is similar to the detection limit in plasma spiked with Aβ42 oligomers (FIG. 13E,F).

The agreement between SOBA and the clinical diagnoses for the MCI and AD samples (n=147) was excellent with only one discrepancy. In this case, the clinical diagnosis was AD, but the plasma SOBA value was low (12,323±3503). We cannot definitively determine whether SOBA or the clinical diagnosis is incorrect; neuropathological results are not available. There are 13 samples from the CO group that tested positive, 12/13 were confirmed to progress to MCI in later years. There was a high correlation between detection of toxic oligomers in the plasma (and CSF) and being on the AD continuum, with robust discrimination between controls and MCI and AD cases, as well as individuals pre-symptomatically incubating the disease. The robust discrimination obtained with SOBA due to the high specificity for the toxic oligomers. For comparison, the total Abeta42 concentration was also measured in the CSF for these individuals; CSF usually provides superior results compared with blood and the [Abeta42] is the most widely used biomarker for confirmation of MCI and AD. As illustrated in FIG. 14B, Abeta42 levels heavily overlap for the CO, MCI and AD cases and it is not possible to discriminate CO from MCI/AD. Thus, SOBA is not tracking with the total Abeta42 in the sample and by virtue of the improvements developed here, SOBA is able to selectively detect the alpha-sheet containing toxic oligomers in blood, which was not possible using prior methods. For comparison, SOBA in blood provides 99% sensitivity and 99% specificity, and note that non-AD dementia cases are SOBA-negative, while Abeta42 in CSF provides 67%/65% sensitivity and specificity.

We also developed a version of SOBA (Next-Gen) using another capture peptide (AP530) to show that it is based on structure, not sequence, and along with using a single antibody containing the horse radish peroxidase reporter protein and a blocker in the washing steps. Critically, the PDA coating and dimeric-peptide coating were retained, but the test itself is faster and involves less steps. Tests with this version of SOBA (FIG. 14C) provided comparable results to those in FIG. 14A, but they also extend to a new cohort, fresher samples and increased ethnic diversity in the donors (samples 2-3 years old). Here again the sensitivity and specificity are excellent (the values of the signals are slightly lower, as the new version results in less nonspecific signal associated with the second antibody in the original ELISA-like assay). In addition, as these samples are newer, they made use of improved techniques for detection of Abeta42 in CSF. As can be seen in FIG. 14D, the overlap between the controls and AD patients remains and it is not possible to discriminate between these two groups using this widely used AD biomarker.

The SOBA assay is not limited to detection of the amyloid beta toxic oligomers associated with Alzheimer's disease. It has also been tested on CSF and plasma from patients diagnosed with Parkinson's disease (PD). In this case the two-antibody PDA/dimer version of the assay was employed, but the Abeta antibody was replaced by and alpha-synuclein antibody, as toxic oligomers of alpha-synuclein are associated with PD and Lewy Body dementia (LBD). The CSF samples from the PD patients provided very strong signals (diluted 1:10 in PBS) (FIG. 14E). CSF samples from CO and AD subjects from the plasma study described above were evaluated and they were SOBA negative. While the AD samples were negative for the alpha-synuclein antibody, they were positive for AD, both CSF and plasma, using the Abeta antibody. Also interesting was that several of subjects in the control group were diagnosed with PD and/or LBD up to 16 years later when autopsies were performed. After seeing the autopsy findings, we tested their banked CSF when they were cognitively unimpaired and they were SOBA-positive. These results demonstrate that SOBA can discriminate PD and LBD from controls and AD cases as well as pre-symptomatically detect the toxic oligomers.

We have also designed alpha-sheet peptides with radiotracers to track toxic soluble oligomers via PET imaging. Our alpha-sheet peptides are small and very soluble (>50 mg/ml) and are readily transported across the blood brain barrier. They are not aggregation-prone and are non-toxic to animals. With this in mind, we are developing a detection diagnostic using $^{18}$F-modified alpha-sheet peptides for PET scanning in vivo. Compared with other amyloid PET-tracers that specifically recognize amyloid plaques (florbetaben for example), our alpha-sheet PET-tracer target the toxic, soluble oligomer in the brain.

FIG. 15 shows a WT control mouse on the left and a transgenic presymptomatic AD mouse on the right. While the delivery, dosing and timing of the injection and the imaging are not optimized, tracer can be seen in the animal on the right and it appears to be in the olfactory bulb. Another study recently identified olfactory abnormalities in another AD transgenice mouse line associated with Abeta oligomers and odor detection affecting the peripheral olfactory sensory neurons of mice.

Discussion

Diagnostics for Amyloid Diseases

Focusing on the disease areas addressed with SOBA above, AD presents a difficult pathway for the future of treatment since the presentation of symptoms is often decades after the biological damage has taken place. This means that for intervention to be efficacious, it should take place decades before the individual or their doctor has any indication that the disease may be present. Thus, the most important factor in AD treatment is early detection. Diagnostic tests for AD have been proposed and investigated for decades, with little or no success in terms of prognostic capacity. Most tests are predictive solely in that they indicate that fibrils or high molecular weight aggregates have already formed. While plaques can sometimes be seen earlier than the presentation of symptoms, it is still far too late in the disease process to intervene successfully since the low molecular weight aggregates are responsible for toxicity and have had years to do damage. Furthermore, cognitively normal individuals can have plaques without any symptoms. Other uses for a robust assay that can detect the early toxic species include their use in preclinical animal studies (as is done for the dimeric inhibitors described above), their use to monitor the effect of treatment in humans, and as a clinical endpoint in trials.

Parkinson's disease is very similar. It cannot be accurately diagnosed in its early stages and instead is caught when symptoms become more severe. In this case, however, there are some treatments that could be employed with early detection; however, a truly disease-modifying treatment is still desired, and for that early diagnostics are critical. The two applications of the SOBA technology highlight how early, presymptomatic detection are possible and robust, noninvasive diagnosis even in the later stages would be preferable to the more costly, more subjective assessments and more invasive biomarkers (CSF, PET imaging) employed now, particularly as they report on later stages of the disease when amyloid fibrils and plaques are present. Consequently, we have also designed alpha-sheet designs with radiotracers to track toxic soluble oligomers, which precede plaque formation, via PET imaging.

Materials and Methods

Synthesis of Alpha-Sheet Peptide

The AP193 capture peptide (Ac-RGEmNyFwMNTh-EYYGWtMnCkMIGR-NH2) (SEQ ID NO:8) for SOBA was produced on Rink amide resin with Fmoc chemistry using manual standard solid phase peptide synthesis and HBTU/DIEA chemistry as well as via microwave peptide synthesis using a Liberty Blue peptide synthesizer (CEM) and Oxyma/DIC chemistry. The resin-bound peptide was cleaved and side chains deprotected with TFA/TIPS/DODT/H2O (92.5:2.5:2.5:2.5) and precipitated with cold ether. Crude peptide was purified by reverse phase high-performance liquid chromatography (HPLC, Shimadzu) to >98% purity (Phenomenex Jupiter 5 µm C18 300 Å LC preparative column 250×21.2 mm). The mass and sequence of the purified peptide was confirmed by mass spectrometry (MS) on a Bruker Esquire Ion Trap electrospray mass spectrometer. The α-sheet structure of the peptide was confirmed by circular dichroism (CD, Jasco J720). The peptide was lyophilized and stored at −80° C.

Preparation of Synthetic Aβ42 Oligomer Standards

Aβ42 (residues 1-42, also referred to as Aβ) was obtained from the ERI Amyloid Laboratory, LLC (Oxford, CT). We followed the procedures of Shea et al. (2019), and they are described below. Aβ was deseeded and aliquoted using hexafluoroisopropanol (HFIP, Sigma-Aldrich, St. Louis, MO, USA). The aliquots were sonicated at 1 mg/ml in HFIP in a bath sonicator for 5 min, followed by 25 min on ice, another round of 5 min sonication, followed by a final round of 25 min on ice. The resulting solution was then blown under a gentle stream of $N_2$ gas and dried using a SpeedVacT™ concentrator (Savant ISSI10, ThermoFisher Scientific) for 2 h on the low (no temperature) setting, which resulted in a monomerized Aβ film that was stored at −20 or −80° C.

Aβ stock for aggregation assays and synthetic toxic oligomers was prepared by allowing a film aliquot to equilibrate at room temperature (RT) for 5 min. The film was then dissolved to 0.75 mg/mL with filtered 6 mM NaOH (pH 11.6, Sigma-Aldrich), flicked to ensure the film was dissolved, followed by sonication for 5 min. This solution was transferred to a 0.22 μm Costar cellulose acetate centrifuge filter (Sigra-Aldrich) using a glass pipette and centrifuged at 7,000 rpm (~4000×g) for 2 min. This solution was then transferred, using a glass pipette, to an Eppendorf microcentrifuge tube (Sigma-Aldrich); the peptide concentration was measured using a NanoDrop™ 2000 Spectrometer (ThermoFisher Scientific) at 280 nm using an extinction coefficient of 1490 $M^{-1}$ $cm^{-1}$. The resulting stock solution was allowed to rest at 25° C. for four hours, after which it was used immediately or stored at 4° C. until needed (no longer than 1 week). Stock Aβ was diluted to 75 μM using pH 7.4 phosphate-buffered saline (PBS) (10 mM phosphate, 130 mM NaCl, and 2.7 mM KCl; Sigma-Aldrich) immediately before preincubation for 24 h at 25° C. to yield the toxic oligomers during the lag phase of aggregation, as described previously (13). Samples were placed and stored on ice after incubation, The samples were diluted to 25 μM immediately before CD was performed to ensure that an α-sheet spectrum was obtained, which is characterized by a flat, null spectrum. A flat spectrum is obtained because alpha-sheet structure is comprised of amino acids alternating between local $α_L$ and $α_R$ chirality, which lead to cancellation of the signal by CD. Furthermore, previous studies characterizing these oligomers by size exclusion chromatography (SEC) showed that the toxic oligomers generated with this protocol are a mix of hexamers and dodecamers, although we note that SEC is a low-resolution method and these assignments are not definitive, for example they could be pentamers instead of hexamers. SEC was performed to confirm that the oligomer standards contained the low molecular weight species and were devoid of higher molecular weight β-sheet protofibrils. Monomer and protofibril samples were also prepared and applied to SOBA to confirm specificity of the binding to the α-sheet oligomers. The monomers were prepared in NaOH to prevent aggregation and the protofibrils were obtained from longer incubations of Aβ42, 120 hr. SEC and CD confirmed that the monomer sample was indeed monomeric and contained disordered/random coil structure. Likewise, the protofibril samples were β-sheet and formed higher molecular weight nontoxic aggregates.

Soluble Oligomer Binding Assay (SOBA)

Design of SOBA for Detection of Toxic Oligomers in Plasma

Previous assays used a pre-functionalized Nunc Immobilizer™ plate for lysine linkage of molecules and a developing reagent for colorimetric readout. Given the low concentrations of Aβ42 in plasma, and the fact that toxic oligomers are just a fraction of this, we sought to amplify the signal by: (A) using a chemiluminescent developing reagent rather than a colorimetric TMB reagent, and (B) developing a coating for polystyrene plates to increase display of our capture peptides, which further increased the signal and yielded a drop in the LOQ to attomolar-femtomolar (aM-fM, 10-18-10-5 molar). As a result, the LOQ for SOBA (ag/mL-fg/mL) is over 3 orders of magnitude ($10^3$) more sensitive than most ELISA assays using antibody-capture agents (pg/mL-ng/mL). This sensitivity was critical given the low amounts of alpha-sheet toxic oligomers in plasma.

The polydopamine surface coating increases the amount of covalently bound capture peptide dramatically, increasing the uptake from 21 μg/ml on the Nunc plates to 196 μg/mL with the PDA (FIG. 13A). Additionally, PDA functionalization increased the signal for 1 nM applied Aβ42 oligomers in PBS from background levels to 10× background using the TMB colorimetric protocol (FIG. 13B,C). Introduction of the chemiluminescent reagent alone, without PDA functionalization, lowered the LOD to 100 fM (in PBS) while maintaining statistical significance (FIG. 13D). The combination of using chemiluminescence and the increased display of our AP193 capture peptide through the PDA coating decreased the LOD to aM, greatly surpassing that of the 'original' TMB protocol by 9-orders of magnitude (in PBS and CSF) (FIG. 13). To determine performance in plasma, Aβ42 oligomer-spiked samples of commercial pooled human plasma (Innovative Research, Novi, MI) were assessed. Statistically significant signals (relative to blanks) were observed to 1 fM in plasma (FIG. 13E). Importantly, the specificity was maintained throughout all protocols; monomeric and protofibrillar Aβ42 applied at even a high concentration of 100 μM resulted in a signal on par with background, as illustrated for spiked plasma (FIG. 13E). FIG. 13F shows a log-log plot of SOBA values versus the concentration of Aβ42 oligomer and the LOD is 1 fM (~4.51 fg/ml), which corresponds to a SOBA signal of 21,943. For comparison, the LOD of toxic oligomer spiked CSF is lower, 0.1 fM (or 100 aM). The detailed steps in the development and use of SOBA are presented below.

Synthetic Aβ TMB (Colorimetric) Protocol—Calibrations

Stock Aβ (described above) was diluted and preincubated in PBS at 75 μM for each experiment. We used our AP193 α-sheet design as the capture agent for all SOBA experiments, AP193 was first dissolved with DMSO (Sigma-Aldrich) to 36 mM, then diluted to 36 μM with $CO_3^{2-}$ buffer (pH 9.6) and incubated in a 37° C. water bath incubator for 2 h to dimerize the peptide, which provides much better capture and significantly boosts the signals. 100 μL of AP193 was plated per well for all positive control wells in a Nunc Immobilizer™ Amino 96-well plate (Corning, Corning, NY, USA), Control blank wells were prepared at the same time following all steps except the attachment of AP193 which was replaced by blank carbonate buffer. The AP193 was coupled to the surface with shaking at room temperature (RT) for 2 hr. The wells were then aspirated and washed with 300 μL PBS-T (0.01% Tween-20 by volume, Sigma-Aldrich) five times. 150 μL of 10 mM ethanolamine (Sigma-Aldrich) was then plated per well and used to quench unreacted sites on the surface by shaking at RT for 2 h. The wells were then aspirated and washed with 300 µL PBS-T five times. Pre-incubated Aβ (75 µM) was then serially diluted (starting with the highest concentration and subsequently diluted to the next highest concentration in the same tube) in PBS, CSF, or plasma to the relevant working concentrations for calibration, and 100 µL was applied per well and incubated for 1 h at 25° C. without shaking. The wells were then aspirated and washed with 300 µL PBS three times. A 0.2 µg/ml dilution of the primary 6E110 anti-Aβ antibody (BioLegend, San Diego, CA, USA) was prepared in 3% BSA in TBS-T (50 mM tris, 100 mM NaCl, 0.01% Tween-20 by volume, pH 7.6) and 100 µL of this solution was plated per well and incubated with shaking at RT for 1 h. The wells were then aspirated and washed with 300 µL PBS three times. 100 µL of a 0.08 µg/ml dilution of the secondary goat anti-mouse HRP-conjugated antibody (Pierce Biotechnology, Waltham, MA, USA) in 3% BSA in TBS-T was plated per well and incubated with shaking at RT for 45 min while covered in foil to avoid bleaching of the HRP. The wells were then aspirated and washed with 300 µL PBS three times. 100 µL of room temperature tetramethylbenzidine (TMB, ThermoFisher Scientific) was plated per well, and incubated with shaking at RT for 15 min while covered in foil. The reaction was quenched with 100 µL of 2 M $H_2SO_4$ (Sigma-Aldrich) and the absorbance measured at 450 nm on a multimode plate reader (PerkinElmer).

Chemiluminescent Protocol—Calibrations

All steps in this protocol were the same as the TMB protocol, up to the point of adding the primary antibody. in this case, 0.1 µg/ml dilution (instead of 0.2 µg/m) of the primary 6E10 anti-Aβ antibody was prepared in 3% BSA in TBS-T and 100 µL of this solution was plated per well and incubated with shaking at RT for 1 h. The wells were then aspirated and washed with 300 µL PBS three times. 100 µL of a 0.04 µg/ml dilution of the secondary goat anti-mouse HRP-conjugated antibody (Santa Cruz Biotechnology) in 3% BSA in TBS-T was applied per well and incubated with shaking at RT for 45 minutes while covered in foil to avoid bleaching of the HRP. The wells were then aspirated and washed with 300 µL PBS six times. 115 µL of room temperature SuperSignal™ ELISA Femto Maximum Sensitivity Substrate (Thermofisher) was plated per well and incubated in a PerkinElmer multimode plate reader with shaking for 30 s before reading the luminescence with a 1 s integration time. SOBA values in the plots using chemiluminescence are raw, uncorrected luminescence readings.

Polydopamine+Chemiluminescent Protocol Calibrations

Dopamine HCl (Sigma Aldrich) was dissolved in 10 mM Tris-HCl (pH 8.5) to 5 mg/ml and immediately plated at 150 µL per well in a 96-well polystyrene plate (Thermofisher). Dopamine HCl rapidly polymerized to form polydopamine (PDA) at this pH and formed a thin film coating on the walls of the plate. This solution was incubated at RT with shaking overnight for 20 h. The following morning, AP193 was dissolved with DMSO (Sigma-Aldrich) to 36 mM, then diluted to 36 µM with $CO_3^{2-}$ buffer (pH 9.6) and incubated in a 37° C. water bath incubator for 2 h to dimerize the peptide to boost the signals. The wells of the plate with polydopanine coating were then aspirated and washed with 300 µL DI $H_2O$ five times with aggressive washing to dislodge any residual polydopamine and dried at 37° C. for 1h. Then 100 µL of AP193 was plated per well for all positive control wells in the PDA-coated polystyrene plate and coupled with shaking at RT for 2 h. The wells were then aspirated and washed with 300 µL PBS-T (0.01% Tween-20 by volume, Sigma-Aldrich) five times. 150 µL of 10 mM ethanolamine (Sigma-Aldrich) was then plated per well and used to quench unreacted sites on the surface by shaking at RT for 2 h. The wells were then aspirated and washed with 300 µL PBS-T five times. The remainder of the protocol conformed to the chemiluminescent calibration protocol stated above, maintaining the 0.1 mg/ml 6E10 primary antibody concentration and the 0.04 mg/ml IgG secondary concentration.

Processing of Plasma Samples with SOBA

All human plasma samples presented here used the PDA chemiluminescent protocol. After establishing the conditions above, the PDA coated plate was prepared per the protocol provided in the Polydopanine+chemiluminescent protocol–calibrations section. After plate preparation, the CO and AD plasma samples (pre-aliquoted into 115 µL samples to avoid repeated freeze-thaw cycles) were thawed for 5 min at 37° C. during the ethanolamine reaction step. After thawing, all samples were centrifuged at 3200×g for 15 min at 4° C. for platelet removal. 100 µL of each plasma sample was plated per well and the plate was incubated at 25° C. for 1h without shaking. The wells were then aspirated and washed with 300 µL PBS three times. Lastly, the protocol for chemiluminescence was employed. Raw luminescence values are reported for samples evaluated in triplicate. In every case the samples were evaluated on two different days (a single well one day and duplicates on another, or vice versa) to ensure that the results were reproducible. Also, most samples were tested over the span of several months to test the stability of the signals. Commercially sourced pooled plasma or single-donor pediatric plasma was included on every plate as a negative control.

Alzheimer's Disease Plasma Samples Evaluated by SOBA 379 plasma and matched CSF samples from 310 study participants were obtained from the Behavioral Neurosciences Group (BNG) Sample and Data Repository [formerly University of Washington Alzheimer's Disease Research Center (UW ADRC) biobank] through a Material Transfer Agreement between the VA Puget Sound Healthcare System and its investigator Dr. Elaine Peskind and the University of Washington to Dr. Valerie Daggett.

Parkinson's Disease CSF Samples Evaluated by SOBA

CSF and blood samples were obtained from participants undergoing implantation of Deep Brain Stimulation (DBS) electrodes for Parkinson's Disease at the University of Washington Medical Center.

SOBA Protocol for PD CSF Test

The CSF SOBA-PD protocol was performed using the same methods as the plasma SOBA-AD protocol with the following changes: CSF was thawed for 5 min at 37 C and diluted 1:10 with PBS (i.e. 30 µl of CSF was diluted with 270 µl of PBS to a final volume of 300 µl for triplicate measurements) prior to plating. We used the 4B12 anti-α-synuclein antibody clone (Biolegend 807801) at 0.025 µg/ml as the primary antibody, and the BP-HRP m-IgGκ antibody (Santa Cruz Biotechnology sc-516102) at 0.01 µg/ml as the secondary antibody.

Next-Generation SOBA

Another faster version of SOBA with lower variability providing lower coefficients of variation was also developed that makes use of different capture peptides, blocking agents, and a single 6E10 anti-Abeta antibody containing the horse radish peroxidase, obviating the need for a secondary antibody. Results of this version of SOBA are presented using commercial plasma samples.

$^{18}$F-Alpha-Sheet Peptide Tracer for Detection of Toxic Oligomers In Vivo

We linked an $^{18}$F-benzoate to a primary amine on an Aβ peptide. Radiolabeling was verified and purification was carried out using HPLC. If there is sufficient yield in radiolabeling with this method we will move forward, otherwise we will consider click-chemistry-based radiolabeling or other labeling protocols.

Mice were obtained from Charles River Laboratory. We used transgenic mice with the Swedish mutation (Tg2576), which we have employed in other studies with our compounds. These mice exhibit behavioral deficits and biochemical hallmarks of AD during aging, including: marked inflammatory changes; hyperphosphorylated Tau aggregates; neuronal loss; amyloid plaques and insoluble Abeta deposits and plaques that are detectable at 13 months of age; and inferior performances in learning and memory tests. Charles River has developed a timeline for studies in these mice, indicating that 5 months is a good time to begin to administer treatment. However, this is based on the fact that Tg2576 mice display significantly reduced contextual memory and increased errors in lab tests at this point. Thus, we would like to test our tracer with mice starting at 3 months of age, as well as 5 months. Starting at 3 months will give us insights into the early stages of the disease, before symptoms present and insoluble plaques are formed, just as total Abeta begins to increase (indicating oligomerization and decreased clearing in the brain). Based on these findings we tested mice with transgenic mice early in AD progression compared with wild type (WT) cases, at 3 month- and 5 months of age. The tests involved injection of the $^{18}$F-labeled alpha-sheet peptide into both WT and Tg2576 mice, with PET scans to verify the presence/absence of localization of our tracer. We observed localization of the tracer in the brain of the transgenic mice.

REFERENCES

1. Son, G., Yoo, S-J, et al, Moon, C., "Region-specific amyloid-beta accumulation in the olfactory system influences olfactory sensory neuronal dysfunction in 5×FAD mice. *Alz. Res. & Therapy*, 13, 4, 2021.

Example 4. Aβ Peptide Dendrimers for Improved Inhibition of Amyloidogenesis

Introduction

As described in Example 1, dimers were designed and tested with the objective of improving the inhibitory properties of the alpha-sheet peptides. Here the objective is to move beyond dimers to dendrimers. Dendrimers built around a poly-lysine core scaffold were developed to create multi-valent alpha-sheet-hairpin peptides. These dendrimers allow multiple hairpin peptides to be attached to a single carrier core. The poly-lysine scaffolding is produced with simultaneous deprotections of primary amine protecting groups in order to create a branched peptide rather than a single linear peptide. Examples of dendrimers comprised of four AP5 monomeric peptides covalently attached to a poly-lysine core are described.

Results

The AP5 dendrimer contains four AP5 monomeric hairpins covalently linked to the lysine residues as shown schematically in FIG. 16. This allows for 8 alpha-sheet binding strands/surfaces.

The AP5 dendrimer was tested for binding of Abeta42 oligomers in the TMB SOBA assay without PDA coating (FIG. 17). The effect is >4-fold at low concentration when the avidity becomes more important. For example, at 2.5 nM the ratio of the Dendrimer and Dimer signals is 5.8. By preforming the same evaluation of the binding of Abeta42 oligomers but in this case using chemiluminescence and the PDA coating, the signals are much, much higher than with the AP510 dimer, and they are still highly significant at 1 fM (FIG. 18).

Materials and Methods

Peptide Synthesis

Standard manual Fmoc peptide synthesis was used to produce an AP5-MAPS peptide[1], with Ninhydrin tests used to confirm proper coupling between each amino acid. Each coupling was carried out in 4-fold molar excess with respect to the available primary amines on the previous residue. The core lysine residues have two available primary amines. Therefore, after adding the first lysine of the dendrimer, both the primary N-terminal amine and the R-group amine must be reacted, so a 4-fold excess with respect to the available amine groups on the first lysine was used, which is an 8-fold molar excess with respect to the resin, which has only one available amine to react. After adding the second lysine to the synthesis, we react with a 16-fold M excess with respect to the resin for all subsequent couplings to synthesize the AP5 sequence onto the poly-lysine core. To simultaneously deprotect the N-terminus and R-group of the core lysine amino acids before addition of the next amino acid of the sequence, an Fmoc-Lys(Fmoc) amino acid was used for the dendrimer core. This allows both Fmoc protecting groups to be removed with the piperidine base.

SOBA

The methods provided above in Example 3 were used for the preparation of the Abeta42 standards and the preparation of the SOBA plates and the assay protocols.

REFERENCES

1. K. Sadler and J. P. Tam, "Peptide dendrimers: Applications and synthesis," *Rev. Mol. Biotechnol.*, vol. 90, no. 3-4, pp. 195-229, 2002.

We claim:

1. An α-sheet polypeptide multimer, comprising:
   two monomeric α-sheet polypeptides that are covalently linked,
   wherein each monomeric α-sheet polypeptide comprises the amino acid sequence of rGeMnLsWmneyyGwTmNmKcGr (SEQ ID NO:25) or its reverse chiral counterpart,
   wherein residues in lower-case are D amino acids, residues in upper case are L amino acids, and G residues are achiral.

2. The α-sheet polypeptide multimer of claim 1, wherein the two monomeric α-sheet polypeptides are covalently linked by 1 or more of the following:
   (a) disulfide bonds;
   (b) other covalent bonding between cysteine residues present in two monomers;
   (c) thioether bridges between two monomers;
   (d) covalent bonding between tyrosine residues present in two monomers;
   (e) 1,2,3-triazole bridges between two monomers;
   (f) amide bonds between two monomers;
   (g) covalent bonding between histidine residues present in two monomers;
   (h) conjugation to a core structure that covalently links multiple monomeric α-sheet polypeptides, including but not limited to poly-lysine, poly-ornithine, polyethylene glycol (PEG), Poly(amidoamine) (PAMAM), other polymers, and nanoparticle core structures;
   (i) covalent bonding between norbrorene moieties present in two monomers;
   (j) covalent bonding between a maleimide motif present in one monomer and the sulfur atom on a cysteine residue another monomer;
   (k) covalent linkage of two monomers by a linking moiety including but not limited to Bis(maleimido)ethane (BMOE); 1,1'-(2,2'-oxybis(ethane-2,1-dioyl))bis(1H-pyrrole-2,5-dione) (MalPEG1);

Beta-Alanine

6-Aminohexanoic acid

12-Aminododecanoic acid

8-Aminooctanoic acid 8-amino-3-6-dioxaoctanoic-acid

3. A pharmaceutical composition, comprising:
   (a) the α-sheet polypeptide multimer of claim 1; and
   (b) a pharmaceutically acceptable carrier.

4. A composition, comprising:
(a) a polymer coating on a surface; and
(b) α-sheet polypeptides covalently linked to the polymer coating, wherein the α-sheet polypeptides comprise the α-sheet polypeptide multimer of claim 1.

5. The composition of claim 4, wherein the polymer comprises a catecholamine polymer.

6. The composition of claim 4, wherein the polymer comprises polydopamine, poly-L-DOPA, polyepinephrine, polynoradrenaline, and any synthetic product which contains a di-hydroxyl phenol and a branched chain of any length that terminates with a primary amine, and combinations thereof.

7. The composition of claim 4, wherein the polymer comprises polydopamine (PDA).

8. The α-sheet polypeptide multimer of claim 1, wherein the two monomeric α-sheet polypeptides are covalently linked via a disulfide bond.

9. The α-sheet polypeptide multimer of claim 1, wherein the two monomeric α-sheet polypeptides are covalently linked via Bis(maleimido)ethane (BMOE).

10. The α-sheet polypeptide multimer of claim 1, wherein the two monomeric α-sheet polypeptides are covalently linked via 1,1'-(2,2'-oxybis(ethane-2,1-dioyl))bis(1H-pyrrole-2,5-dione) (MalPEG1).

11. The α-sheet polypeptide multimer of claim 1, wherein each monomeric α-sheet polypeptide comprises the amino acid sequence: rGeMnLsWmneyyGwTmNmKcGr (SEQ ID NO:25), wherein residues in lower-case are D amino acids, residues in upper case are L amino acids, and G residues are achiral.

12. The α-sheet polypeptide multimer of claim 11, wherein the two monomeric α-sheet polypeptides are covalently linked via a disulfide bond.

13. The α-sheet polypeptide multimer of claim 12, wherein the N-terminus of the polypeptide is acetylated.

14. The α-sheet polypeptide multimer of claim 13, wherein the C-terminus of the polypeptide is amidated.

15. A medical device comprising the α-sheet polypeptide multimer of claim 1, coated on a surface of the medical device.

16. An α-sheet polypeptide comprising the amino acid sequence of
rGeMnLsWmneyyGwTmNmKcGr (SEQ ID NO:25) or its reverse chiral counterpart,
wherein residues in lower-case are D amino acids, residues in upper case are L amino acids, and G residues are achiral.

17. A composition, comprising:
(a) a polymer coating on a surface; and
(b) α-sheet polypeptides covalently linked to the polymer coating, wherein the α-sheet polypeptides comprise the α-sheet polypeptide of claim 16.

18. The composition of claim 17, wherein the polymer comprises a catecholamine polymer.

19. The composition of claim 17, wherein the polymer comprises polydopamine, poly-L-DOPA, polyepinephrine, polynoradrenaline, and any synthetic product which contains a di-hydroxyl phenol and a branched chain of any length that terminates with a primary amine, and combinations thereof.

20. The composition of claim 17, wherein the polymer comprises polydopamine (PDA).

21. The α-sheet polypeptide of claim 16, comprising the amino acid sequence: rGeMnLsWmneyyGwTmNmKcGr (SEQ ID NO:25), wherein residues in lower-case are D amino acids, residues in upper case are L amino acids, and G residues are achiral.

22. The α-sheet polypeptide of claim 21, wherein the N-terminus of the polypeptide is acetylated.

23. The α-sheet polypeptide of claim 22, wherein the C-terminus of the polypeptide is amidated.

24. A pharmaceutical composition, comprising:
(a) the α-sheet polypeptide of claim 16; and
(b) a pharmaceutically acceptable carrier.

25. A medical device comprising the α-sheet polypeptide of claim 16, coated on a surface of the medical device.

* * * * *